(12) United States Patent
Jiang et al.

(10) Patent No.: US 10,941,039 B2
(45) Date of Patent: Mar. 9, 2021

(54) DIHYDROGEN TETRAMETAPHOSPHATE, ITS DERIVATIVES, AND PREPARATION THEREOF

(71) Applicant: MASSACHUSETTS INSTITUTE OF TECHNOLOGY, Cambridge, MA (US)

(72) Inventors: Yanfeng Jiang, Arlington, MA (US); Khetpakorn Chakarawet, Cambridge, MA (US); Julia Stauber, Cambridge, MA (US); Christopher Colin Cummins, Dorchester, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 17 days.

(21) Appl. No.: 16/024,865

(22) Filed: Jul. 1, 2018

(65) Prior Publication Data

US 2018/0354797 A1    Dec. 13, 2018

Related U.S. Application Data

(62) Division of application No. 15/312,658, filed as application No. PCT/US2015/034461 on Jun. 5, 2015, now Pat. No. 10,017,388.

(Continued)

(51) Int. Cl.
    *C01B 25/44*     (2006.01)
    *C07C 43/225*    (2006.01)
    (Continued)

(52) U.S. Cl.
    CPC .......... *C01B 25/44* (2013.01); *C07C 43/225* (2013.01); *C07F 9/1415* (2013.01); *C07H 19/16* (2013.01); *C07J 9/00* (2013.01); *C09D 5/00* (2013.01)

(58) Field of Classification Search
    IPC ............... C01B 25/44; C07C 43/225; C07F 9/1415; C07H 19/16; C07J 9/00; C09D 5/00
    See application file for complete search history.

(56) References Cited

U.S. PATENT DOCUMENTS 2,618,651 A * 11/1952 Page ............... C07C 67/08
                                              560/98
2,774,672 A * 12/1956 Griffith .............. C11D 7/16
                                              426/563

(Continued)

FOREIGN PATENT DOCUMENTS

JP    05-306317    11/1993

OTHER PUBLICATIONS

Facile Synthesis of Mononuclear early transition-metal complexes of K3 cyclo-tetramethaphosphate ([P4O12]4-) and cyclo-trimethaphosphate ([P3O9]3-). Cesar Manna et al. Dalton Trans, 2014, 43, 1509-1518 (Year: 2014).*

(Continued)

*Primary Examiner* — Colin W. Slifka
*Assistant Examiner* — Colette B Nguyen
(74) *Attorney, Agent, or Firm* — Honigman LLP

(57) ABSTRACT

Dihydrogen metaphosphate can be synthesized via protonation, and can react with a dehydrating agent to afford tetrametaphosphate anhydride. A monohydrogen tetrametaphosphate organic ester can be derived from the anhydride. A metal tetrametaphosphate complex can be prepared using a metal salt and a dihydrogen tetrametaphosphate.

8 Claims, 75 Drawing Sheets

Related U.S. Application Data

(60) Provisional application No. 62/009,004, filed on Jun. 6, 2014.

(51) Int. Cl.
*C07F 9/141* (2006.01)
*C07H 19/16* (2006.01)
*C07J 9/00* (2006.01)
*C09D 5/00* (2006.01)

(56) References Cited

U.S. PATENT DOCUMENTS

| | | | | |
|---|---|---|---|---|
| 3,895,095 A | * | 7/1975 | Kobylinski | B01D 53/9418 423/305 |
| 4,247,526 A | * | 1/1981 | Jarvis | A61K 8/24 423/266 |
| 4,292,202 A | * | 9/1981 | Vartuli | B01J 23/002 502/209 |
| 4,336,148 A | * | 6/1982 | Wirth | C09K 3/16 44/316 |
| 4,404,408 A | * | 9/1983 | Wirth | C07C 43/13 568/680 |
| 6,077,962 A | * | 6/2000 | Prakash | C07C 229/24 549/253 |
| 2011/0111288 A1 | * | 5/2011 | Nishida | C01B 25/455 429/199 |

OTHER PUBLICATIONS

Synthesis and Characterization of Cyclotetraphosphato Complexes of Rh(I), Ir(1), Ru(II), and Pd(II). (Year: 2016).*

Facile Synthesis of Mononuclear early transition-metal complexes of K3 cyclo-tetramethaphosphate ([P4O12]4-) and cyclotrimethaphosphate ([P3O9]3-). Cesar Manna et al. Dalton Trans, 2014, 43, 1509-1518.

Synthesis and Characterization of Cyclotetraphosphato Complexes of Rh(I), Ir(I), Ru(II), and Pd(II).

International Search Report dated Sep. 8, 2015, issued in International Application No. PCT/US2015/034461.

The Written Opinion of the International Searching Authority dated Sep. 8, 2015, issued in International Application No. PCT/US2015/034461.

Kamimura, Set al. Synthesis and Characterization of Cyclotetraphosphato Complexes of Rh(I), Ir(I), Ru(II), and Pd(II). Inorganic Chemistry. 2004. Col. 43, No. 2, pp. 399-401.

Jiang, Yet al. Dihydrogen tetrametaphosphate, [P4O12H2]2-: syntheses, solubilization in organic media, preparation of its anhydride P4O11I2- and acidic methyl ester, and conversion to tetrametaphosphate metal complexes via protonolysis. J. Am. Chem. Soc. Aug. 7, 2014 vol. 136. pp. 11894-11897.

Griffith, E.J. New sodium phosphates. J. Am. Chem. Soc., Aug. 22, 1956. vol. 78. No. pp. 3867-3870.

\* cited by examiner

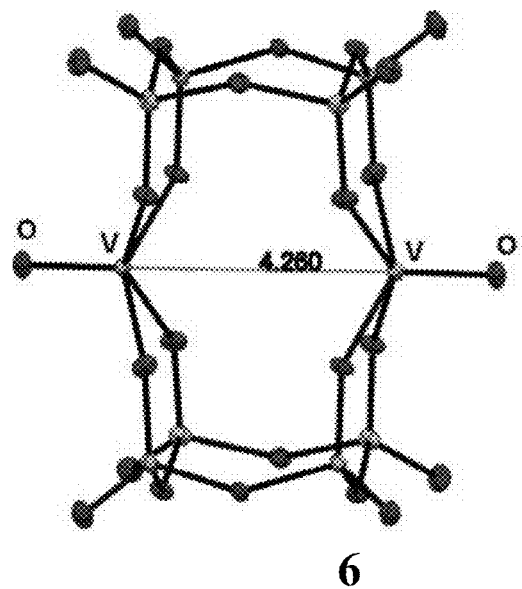
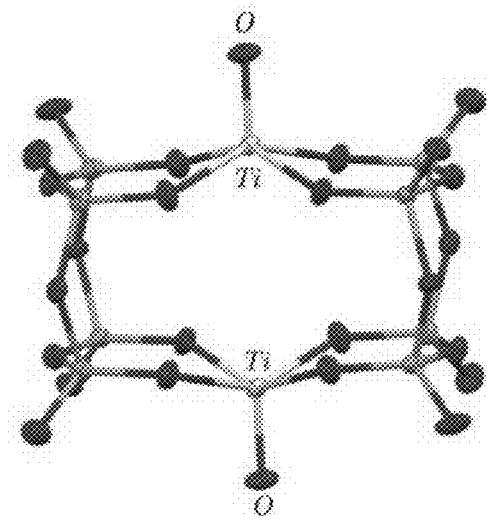
FIG. 33
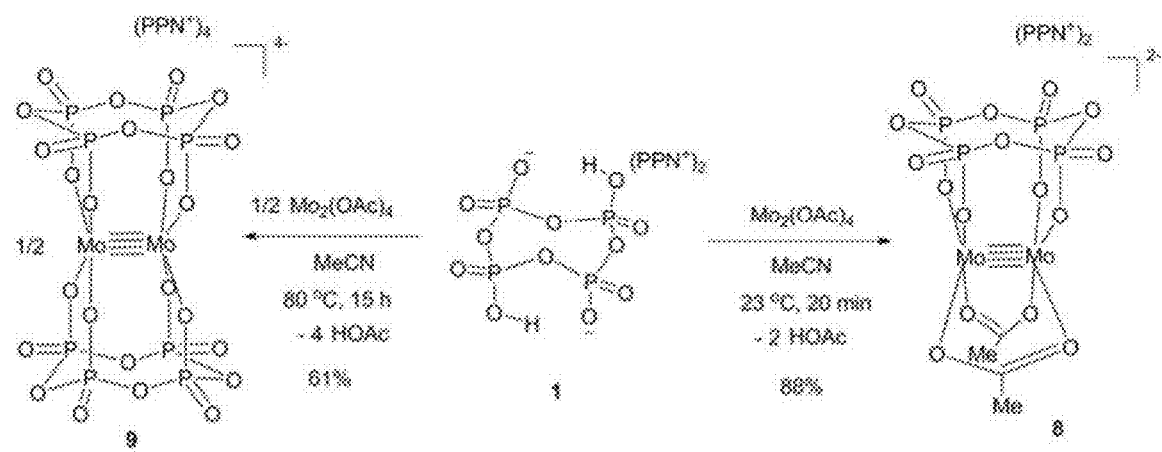
FIG. 34

DIHYDROGEN TETRAMETAPHOSPHATE, ITS DERIVATIVES, AND PREPARATION THEREOF

CLAIM OF PRIORITY

This application is a divisional application of U.S. application Ser. No. 15/312,658, filed on Nov. 20, 2016, now Pat. No. 10,017,388, which claims the benefit under 35 USC 371 International Application No.: PCT/US2015/034461, filed Jun. 5, 2015, which claims the benefit of prior U.S. Provisional Application No. 62/009,004 filed on Jun. 6, 2014, each of which is incorporated by reference in its entirety.

GOVERNMENT SPONSORSHIP

This invention was made with Government support under Grant Nos. CHE-1362118 and CHE-1305124 awarded by the National Science Foundation. The Government has certain rights in the invention.

FIELD OF THE INVENTION

The invention relates to metaphosphate and related complexes and methods of making.

BACKGROUND

A metaphosphate ion is an oxyanion that has the formula $PO_3^-$, the structure of which can be described as being made up of $PO_4$ structural units in which each unit shares two corners with another unit. Cyclo-tetrametaphosphate compounds can have a wide range of applications including use as pigments, catalysts, food additives, and fluorescent materials. Different methods can be used to prepare cyclo-tetrametaphosphate compounds.

SUMMARY

In one aspect, a method of isolating a dihydrogen metaphosphate can include protonating a metaphosphate salt with a reagent in an organic solvent.

In certain embodiments, the metaphosphate salt can include $[P_4O_{12}]^{4-}$ or $[P_3O_9]^{3-}$.

In certain embodiments, the reagent can include a trifluoroacetic anhydride, a trifluoromethanesulfonic anhydride, a trifluoromethanesulfonic acid, or a trifluoroacetic acid. The reagent can include a hydroiodic acid, a hydrobromic acid, a hydrochloric acid, a nitric acid, a perchloric acid, or a sulfuric acid. The organic solvent can include an acetone or an acetonitrile. The organic solvent can include a dichloromethane.

In another aspect, a method of preparing a tetrametaphosphate anhydride can include adding a reagent to a dihydrogen tetrametaphosphate.

In certain embodiments, the reagent can include a N,N'-dicyclohexylcarbodiimide (DCC), a N,N'-diisopropylcarbodiimide (DIC), a 1-Ethyl-3-(3-dimethylaminopropyl)carbodiimide (EDCI), a carbonyldiimidazole (CDI), a phosphoryl chloride ($POCl_3$), or a phosphorus trichloride ($PCl_3$), or a mixture thereof. The dihydrogen tetrametaphosphate can include $[P_4O_{12}H_2]^{2-}$.

In certain embodiments, the method can include isolating the tetrametaphosphate anhydride by removing a byproduct. The byproduct can include dicyclohexylurea.

In another aspect, a method of preparing a monohydrogen tetrametaphosphate organic ester can include adding a reagent to a tetrametaphosphate anhydride. The monohydrogen tetrametaphosphate organic ester can include a monohydrogen tetrametaphosphate methyl ester.

In certain embodiments, the reagent can include an alcohol, a nucleoside, an amino acid, or a steroid, or a mixture thereof. The alcohol can include methanol. The reagent can include an acetonitrile and a dichloromethane, or a mixture thereof.

In another aspect, a method of preparing a metal tetrametaphosphate complex can include adding a metal salt to a dihydrogen tetrametaphosphate in a solvent. The metal tetrametaphosphate complex can include a tin(II) tetrametaphosphate.

In certain embodiments, the metal tetrametaphosphate can include a binary dimeric chromium(II) tetrametaphosphate dimer. The metal tetrametaphosphate complex can include a vanadyl (IV) tetrametaphosphate dimer. The metal tetrametaphosphate complex can include a titanyl tetrametaphosphate dimer. The metal tetrametaphosphate complex can include a molybdenum tetrametaphosphate dimer.

In certain embodiments, the solvent can include an acetonitrile, a dichloromethane, or an acetone, or a mixture thereof.

In certain embodiments, the metal salt can include tin(II) hexamethyldisilazide.

The metal salt can include $Cr(HMDS)_2(THF)_2$.

In another aspect, a solution can include a dihydrogen tetrametaphosphate and an organic solvent. The solution can include water. The organic solvent can include acetone. The organic solvent can include acetonitrile. The organic solvent can include a dichloromethane.

In another aspect, a compound can include a tetrametaphosphate anhydride and a cation. The cation can include a $[PPN]^+$. The cation can include a $[R_4N]^+$, where R is nBu, sBu, iBu, nPr, iPr, Et, or Me. The cation can include a nitrogen-based cation. The cation can include a phosphorus-based cation. The cation can include an alkali or an alkali-earth metal cation. The cation can include an ionic liquid cation.

In another aspect, a method of phosphorylation can include contacting a tetrametaphosphate anhydride with an alcohol, a solid inorganic substrate or an organic polymer substrate having a hydroxyl group, a sterol, or a nucleoside.

In another aspect, a compound can include a monohydrogen tetrametaphosphate organic ester. The monohydrogen tetrametaphosphate organic ester can include a monohydrogen tetrametaphosphate methyl ester.

In another aspect, a compound can include a metal tetrametaphosphate complex.

The metal tetrametaphosphate complex can include a tin(II) tetrametaphosphate, a binary dimeric chromium(II) tetrametaphosphate dimer, a vanadyl (IV) tetrametaphosphate dimer, a titanyl tetrametaphosphate dimer, or a molybdenum tetrametaphosphate dimer.

Other aspects, embodiments, and features will be apparent from the following description, the drawings, and the claims.

BRIEF DESCRIPTION OF THE DRAWINGS

FIG. 33 shows solid-state molecular structure of $[(VO)_2(P_4O_{12})_2]^{2-}$ (6) and $[(OTi)_2(P_4O_{12})_2]^{2-}$ (7) with ellipsoids at the 50% probability level and [PPN]+ cations omitted for clarity.

FIG. 34 shows a synthetic route to the PPN salts of quadruple bonded binary molybdenum tetrametaphsophates 8 and 9.

DETAILED DESCRIPTION

Figure 1:
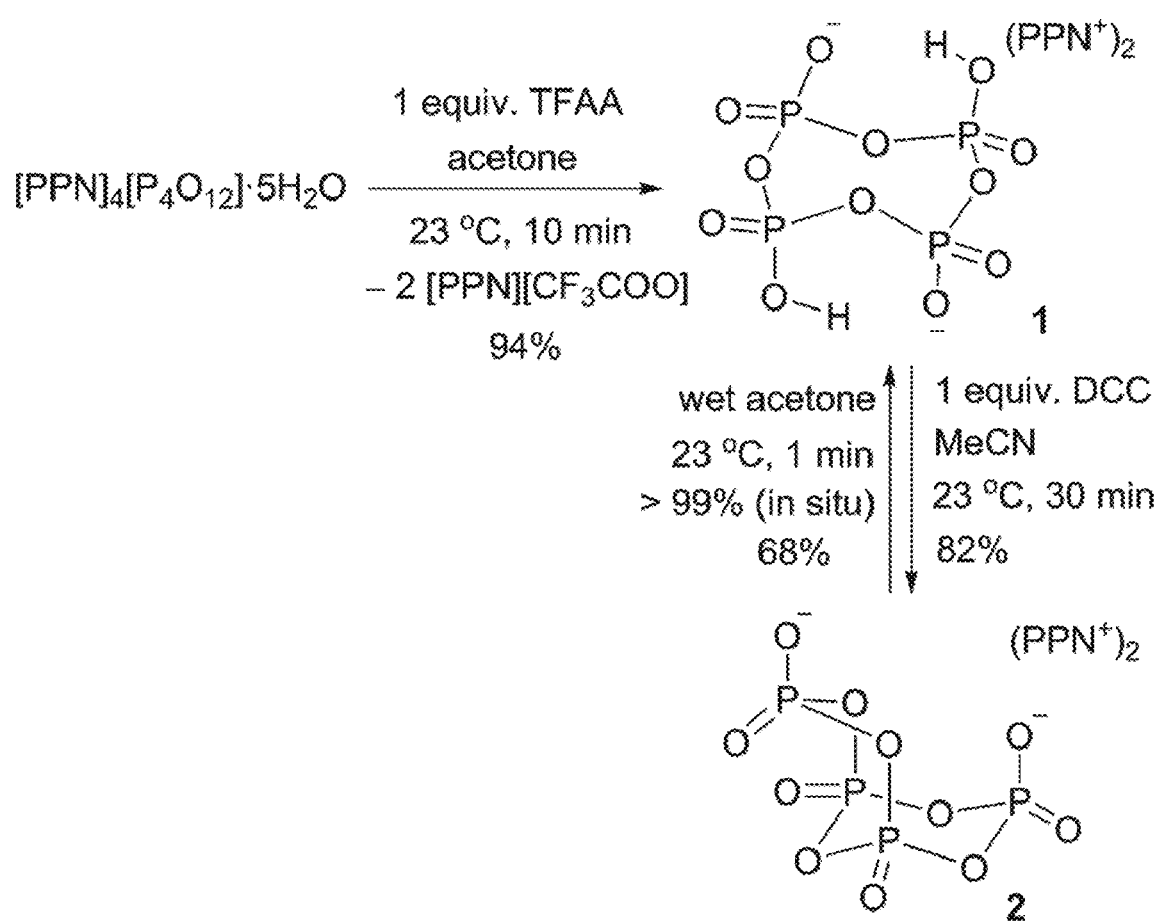
FIG. 1 shows synthetic route to dihydrogen tetrametaphosphate 1 and tetrametaphosphate anhydride 2.

Dihydrogen tetrametaphosphate [P$_4$O$_{12}$H$_2$]$^{2-}$ (1) can be synthesized and isolated (as its PPN salt) via a facile procedure in high yield, such as 93% yield. A pK$_a$ of 15.83±0.11 in acetonitrile can be determined. [P$_4$O$_{12}$H$_2$]$^{2-}$ can react with the dehydrating agent N,N'-dicyclohexylcarbodiimide to afford tetrametaphosphate anhydride [P$_4$O$_{11}$]$^{2-}$ (2) in high yield, such as 82% yield. From 2 a monohydrogen tetrametaphosphate ester [(P$_4$O$_{10}$)(OH)(OMe)]$^{2-}$ (3) with high yield, such as 96%, can be derived by addition of methanol illustrating that 2 can function as a reagent for chemical phosphorylation. Addition of water to 2 can regenerate 1 quantitatively. Deprotonation of 1 by metal amides in the +2 oxidation state can lead to monomeric tin(II) k$^4$ tetrametaphosphate [Sn(P$_4$O$_{12}$)]$^{2-}$ (4) with high yield, such as 78%, and binary dimeric chromium(II) k$^2$ derivative [Cr$_2$(P$_4$O$_{12}$)$_2$]$^{4-}$ (5) with high yield, such as 82%.

The study of cyclic phosphates was initially undertaken almost two centuries ago coinciding with the advent of modern chemistry. See, for example, Durif, A. *Solid State Sci.* 2005, 7, 760-766, which is incorporated by reference in its entirety. Despite drawing considerable interest, the field has progressed at a modest pace, a peculiar circumstance given the speculated importance of cyclic phosphates in prebiotic chemistry. See, for example, Glonek, T.; Kleps, R. A.; Myers, T. C. *Science* 1974, 185, 352-355, which is incorporated by reference in its entirety. Some applications in materials science and conventional coordination chemistry have been developed. See, for example, Trojan, M.; Sulcova, P. *Dyes Pigm.* 2000, 47, 291-294; Onoda, H.; Okumoto, K.; Nakahira, A.; Tanaka, I. *Materials* 2009, 2, 1-9; Besecker, C. J.; Day, V. W.; Klemperer, W. G. *Organometallics* 1985, 4, 564-570; Klemperer, W. G.; Main, D. J. *Inorg. Chem.* 1990, 29, 2355-2360; Day, V. W.; Klemperer, W. G.; Main, D. J. *Inorg. Chem.* 1990, 29, 2345-2355; Kamimura, S.; Kuwata, S.; Iwasaki, M.; Ishii, Y. *Inorg. Chem.* 2004, 43, 399-401; Kamimura, S.; Matsunaga, T.; Kuwata, S.; Iwasaki, M.; Ishii, Y. *Inorg. Chem.* 2004, 43, 6127-6129; Ikeda, Y.; Yamaguchi, T.; Kanao, K.; Kimura, K.; Kamimura, S.; Mutoh, Y.; Tanabe, Y.; Ishii, Y. *J. Am. Chem. Soc.* 2008, 130, 16856-16857; Montag, M.; Clough, C. R.; Mueller, P.; Cummins, C. C. *Chem. Commun.* 2011, 47, 662-664; Kanao, K.; Ikeda, Y.; Kimura, K; Kamimura, S.; Tanabe, Y.; Mutoh, Y.; Iwasaki, M.; Ishii, Y. *Organometallics* 2013, 32, 527-537; Manna, C. M.; Nassar, M. Y.; Tofan, D.; Chakarawet, K.; Cummins, C. C. *Dalton Trans.* 2014, 43, 1509-1518, each of which is incorporated by reference in its entirety. But little is known about the fundamental chemical properties and reactivity patterns of cyclic phosphates.

The expansion of cyclic phosphate chemistry can be realized by synthesizing an organic-media soluble acid form of tetrametaphosphate. A method can be used to synthesize high yielding dihydrogen tetrametaphosphate, which can be a powerful precursor to synthesize not only its corresponding anhydride and methyl ester, but also unconventional metal tetrametaphosphates. Tetrametaphosphate metal complexes can be synthesized via protonolysis.

Cyclic adenosine triphosphate can be decomposed to ATP upon contact with water. See, for example, Baddiley, J.; Michelson, A. M.; Todd, A. R. *Nature* 1948, 161, 761-762; Smith, M.; Khorana, H. G. *J. Am. Chem. Soc.* 1958, 80, 1141-1145, each of which is incorporated by reference in its entirety. The requirement of anhydrous media for the preparation of cyclic phosphate esters was universal not only in the synthesis of phosphate nucleosides, but also in previous attempts to access the acid forms of cyclic phosphates. See, for example, Sood, A.; Kumar, S.; Nampalli, S.; Nelson, J. R.; Macklin, J.; Fuller, C. W. *J. Am. Chem. Soc.* 2005, 127, 2394-2395. Han, Q.; Gaffney, B. L.; Jones, R. A. *Org. Lett.* 2006, 8, 2075-2077, each of which is incorporated by reference in its entirety. Under furnace conditions, the reaction of phosphoric acid with sodium dihydrogen phosphate can afford cyclic phosphate acids. See, for example, Griffith, E. J. *J. Am. Chem. Soc.* 1956, 76, 3867-3870, which is incorporated by reference in its entirety. However, an unrefined structure was reported and there was an ensuing debate on the composition of the obtained polycrystalline form. See, for example, Dornberger-Schiff, K. *Acta Crystallogr.* 1964, 17, 482-491; Gryder, J. W.; Donnay, G.;

Ondik, H. M. *Acta Crystallogr.* 1957, 10, 820-821; Jarchow, O. H. *Acta Crystallogr.* 1964, 17, 1253-1262, each of which is incorporated by reference in its entirety.

The only structurally characterized cyclic phosphate acids are a tetrakis(3,5-xylidinium) dihydrogen cyclohexaphosphate dihydrate and a sodium monohydrogen trimetaphosphate. See, for example, Marouani, H.; Rzaigui, M. *Acta Crystallogr. Sect. E: Struct. Rep. Online* 2010, 66, 0233; Averbuch-Pouchot, M. T.; Guitel, J. C.; Durif, A. *Acta. Cryst.* 1983, C39, 809-810, each of which is incorporated by reference in its entirety.

The latter one can be found among a mixture of strontium-sodium polyphosphates prepared at 300° C.

The acid forms of metaphosphate rings are rare. One reason can be due to their essentially strong acidity, as implicated by the titration of sodium tri- and tetrametaphosphate with nitric acid. See, for example, Watters, J. I.; Kalliney, S.; Machen, R. C. *J. Inorg. Nucl. Chem.* 1969, 31, 3817-3821, which is incorporated by reference in its entirety. Following the "anhydrous" principle, whether a lipophilic organic cation, such as [PPN]$^+$ ([PPN]$^+$=bis(triphenylphosphine)iminium), can enable the access of dihydrogen tetrametaphosphate in nonaqueous media by protonation of metaphosphate salts with a strong acid can be investigated. Treatment of [PPN]$_4$[P$_4$O$_{12}$].5H$_2$O with one equivalent of trifluoroacetic anhydride (TFAA) in acetone at 23° C. resulted in the formation of a single new cyclic phosphate species 1, which exhibits a singlet resonance at −25.6 ppm in its $^{31}$P{$^1$H} NMR spectrum. Upon addition of a dehydrating agent such as DCC (DCC=N,N'-dicyclohexylcarbodiimide) to the reaction mixture, the $^{31}$P{$^1$H} NMR spectrum displayed two triplet signals at −24.4 and −32.5 ppm in an A$_2$X$_2$ spin system, characteristic for the small ultraphosphate [P$_4$O$_{11}$]$^{2-}$ (2) (FIG. 1). See, for example, Glonek, T.; Myers, T. C; Han, P. Z.; Van Wazer, J. R. *J. Am. Chem. Soc.* 1970, 92, 7214-7216; Glonek, T.; Van Wazer, J. R.; Mudgett, M.; Myers, T. C. *Inorg. Chem.* 1972, 11, 567-570, each of which is incorporated by reference in its entirety. These results suggest that 1 is the dihydrogen tetrametaphosphate [P$_4$O$_{12}$H$_2$]$^{2-}$. Indeed, the PPN salt of 1 can be isolated as an analytically pure solid in 94% yield. The presence of acidic P—OH groups is evidenced by a broad singlet at 14.03 ppm in the $^1$H NMR spectrum recorded in CD$_3$CN at 23° C. However, in solution these terminal acidic hydrogens are not localized, as a general property for hydrogen bonded oxyacids. See, for example, Tolstoy, P. M.; Schah-Mohammedi, P.; Smirnov, S. N.; Gol-ubev, N. S.; Denisov, G. S.; Limbach, H.-H. *J Am. Chem. Soc.* 2004, 126, 5621-5634, which is incorporated by reference in its entirety. The fluxional behavior of 1 is reflected in its $^{31}$P{$^1$H} NMR spectrum which displays a single singlet resonance.

Preparation of Dihydrogen Tetrametaphosphate 1 and Tetrametaphosphate Anhydride 2

A method of isolating a dihydrogen tetrametaphosphate can include protonating a metaphosphate salt with a reagent, such as triflic anhydride, triflic acid, trifluoroacetic acid, or trifluoroacetic anhydride, in an organic solvent, such as acetonitrile, dichloromethane, acetone. A method of preparing a tetrametaphosphate anhydride comprising adding a reagent to a dihydrogen tetrametaphosphate. The reagent can include N,N'-dicyclohexylcarbodiimide (DCC), N,N'-diisopropylcarbodiimide (DIC), 1-Ethyl-3-(3-dimethylaminopropyl)carbodiimide (EDCI), carbonyldiimidazole (CDI), phosphoryl halide (POX$_3$, X=I, Br, Cl), or phosphorus trihalide (PX$_3$, X=I, Br, Cl), or a mixture thereof.

The synthesis of 1 is facile and the reaction can be carried out on gram scales under open air conditions using commercial solvents and reagents as received. Trifluoroacetic anhydride can react with H$_2$O from either the solvent or [PPN]$_4$[P$_4$O$_{12}$].5H$_2$O to in situ generate trifluoroacetic acid (TFA), which can then protonate [P$_4$O$_{12}$]$^{4-}$. Acetone can be a solvent as it delivers a simple purification process. The simplicity of the purification procedure in acetone can be attributed to the lower solubility of 1 relative to the byproduct [PPN][CF$_3$COO]. Strong Brønsted acids such as trifluoroacetic acid, triflic acid (TfOH) and triflic anhydride can also react with [P$_4$O$_{12}$]$^{4-}$ to afford 1 in good isolated yields. In comparison, no formation of 1 was observed when [P$_4$O$_{12}$]$^{4-}$ was treated with weak Brønsted acid such as acetic acid.

FIG. 1 shows a synthetic route to dihydrogen tetrametaphosphate 1 and tetrametaphosphate anhydride 2.

Figure 2:
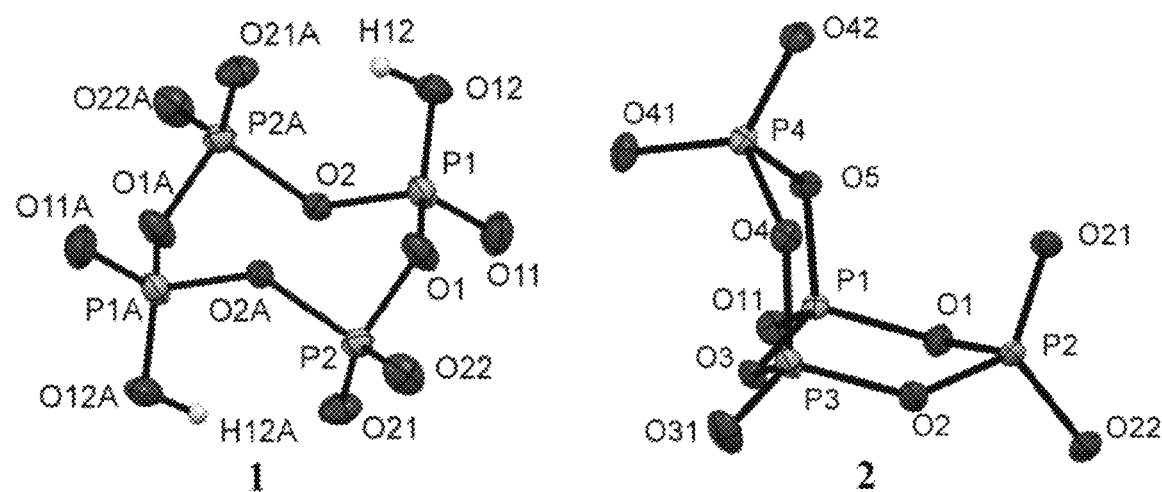
FIG. 2 shows solid-state molecular structures of $[P_4O_{12}H_2]^{2-}$ (1) and $[P_4O_{11}]^{2-}$ (2) with ellipsoids at the 50% probability level and $[PPN]^+$ cations omitted for clarity.

The solid-state structure of 1 can be established using single-crystal X-ray diffraction, and the resulting model in Ci symmetry is depicted in FIG. 2. The hydrogen atoms are calculated to be located at 1,5-positioned phosphates. One feature is the presence of intramolecular hydrogen bonds between the protons and neighboring P—O$^-$ bonds showing a short H O distance of 1.968 Å. Such strong hydrogen bonding interactions can contribute to the stability of 1 in both the solid state and in organic solvents. See, for example, Perrin, C. L.; Nielson, J. B. *Annu. Rev. Phys. Chem.* 1997, 48, 511-544, which is incorporated by reference in its entirety. The P—OH bond length of 1.5096(19) Å is intermediate between the long bridging P—O distances and the short external P—O distances.

A solution can include a dihydrogen tetrametaphosphate and an organic solvent such as acetonitrile, acetone, or dichloromethane. The solution can be a stable solution. The solution can further include water.

Dihydrogen tetrametaphosphate 1 is not stable in aqueous solution; deprotonation and decomposition to linear phosphates and phosphoric acid can be detected by $^{31}$P{$^1$H} and $^1$H NMR spectroscopy. However, 1 shows some stability toward H$_2$O in organic solvents such as acetonitrile and acetone, as no decomposition was detected after 48 h at 23° C. for an acetone solution of 1 containing 50 equivalents of H$_2$O. The dianionic character of 1 serves to inhibit nucleophilic attack at the phosphorus atoms. Such an anion stabilization effect is observed in the chemistry of general anionic phosphate diesters. See, for example, Westheimer, F. H. *Science* 1987, 235, 1173-1178. Bowler, M. W.; Cliff, M. J.; Waltho, J. P.; Blackburn, G. M. *New. J. Chem.* 2010, 34, 784-794, each of which is incorporated by reference in its entirety.

The instability of 1 in aqueous solution makes it impossible to measure its acidity in water. Nevertheless, the pK$_a$ of 1 in acetonitrile can be determined by UV-Vis spectrophotometric titration of [PPN]$_2$[P$_4$O$_{12}$H$_2$] coupled with 2,4-dinitrophenol (pK$_a$=16.66 in MeCN) as a chro-mophore. See, for example, Leito, I.; Kaljurand, I.; Koppel, I. A.; Yagupolskii, L. M.; Vlasov, V. M. *J. Org. Chem.* 1998, 63, 7868-7874. Leito, I.; Rodima, T.; Koppel, I. A.; Schwesinger, R.; Vlasov, V. M. *J. Org. Chem.* 1997, 62, 8479-8483, each of which is incorporated by reference in its entirety. A pK$_a$([P$_4$O$_{12}$H$_2$]$^2$) value of 15.83±0.11 in acetonitrile, corresponding to an intermediate acidity between that of trifluoroacetic acid (pK$_a$=12.65 in MeCN) and acetic acid (pK$_a$=23.51 in MeCN), is in agreement with the experimental observation that 1 can be prepared by protonation of [P$_4$O$_{12}$]$^{4-}$ with trifluoroacetic acid but not with acetic acid. See, for example, Eckert, F.; Leito, I.; Kaljurand, I.; Kuett, A.; Klamt, A.; Diedenhofen, M. *J. Comput. Chem.* 2009, 30, 799-810, which is incorporated by reference in its entirety.

The small ultraphosphate 2 can be isolated. This species has remained elusive since it was first observed in the condensation of orthophosphoric acid by molten DCC in tetramethylurea. It was also one important intermediate in the hydrolysis of $P_4O_{10}$. See, for example, Henry, W.; Nickless, G.; Pollard, F. *J. Inorg. Nucl. Chem.* 1967, 29, 2479-2480, which is incorporated by reference in its entirety. However, neither an isolation procedure nor structural characterization was available. See, for example, Glonek, T.; Van Wazer, J. R.; Kleps, R. A.; Myers, T. C. *Inorg. Chem.* 1974, 13, 2337-2345, which is incorporated by reference in its entirety. The reaction of 1 with a stoichiometric amount of DCC in acetonitrile led to the quantitative formation of 2 (as its PPN salt), which was isolated as an analytically pure solid in 82% yield after removing the byproduct dicyclohexylurea (DCU) that precipitated from the reaction mixture. Since ultraphosphate was originally defined as "an infinite cross-linked polymer," 2 can be better regarded as the anhydride of dihydrogen tetrametaphosphate. See, for example, Thilo, E. *Angew. Chem. Int. Ed.* 1965, 4, 1061-1071, which is incorporated by reference in its entirety.

The solid-state structure of 2 can be established via an X-ray diffraction study and is shown in FIG. 2. The two negatively charged terminal phosphates are bent away from each other probably due to electrostatic repulsion making the two six-membered rings of the bicyclic structure that share a P—O—P bridge adopt boat and chair conformations. The average P—O bond distance in the anhydride bridge is 1.609 Å, slightly longer than the average P—O bond distance in the other inner bridges of 1.563 Å. In the two six-membered rings, the anhydride P—O—P angle of 119.72(7°) is much larger than the average O—P—O angle of 98.38° observed for the terminal phosphorus atoms (P2 and P4).

FIG. 2 shows solid-state molecular structures of $[P_4O_{12}H_2]^{2-}$ (1) and $[P_4O_{11}]^{2-}$ (2) with ellipsoids at the 50% probability level and $[PPN]^+$ cations omitted for clarity. Representative interatomic distances [Å] and angles [°] in 1: P1-O11 1.485(2), P1-O12 1.5096(19), P1-O1 1.610(2), P1-O2 1.576(4), P2-O21 1.459(2), P2-O22 1.483(3), P2-O1 1.6178(19); O11-P1-O12 117.91(15), O21-P2-O22 122.0(2). Representative interatomic distances [Å] and angles [°] in 2: P1-O3 1.6075(12), P3-O3 1.6115(12), P1-O1 1.5621(13), P1-O5 1.5617(12), P3-O2 1.5647(13), P3-O4 1.5651(13), P2-O1 1.6711(14), P2-O2 1.6663(14), P4-O4 1.6686(13), P4-O5 1.6634(12); P1-O3-P3 119.72(7), O5-P4-O4 98.07(6), O2-P2-O1 98.68(6).

Preparation of Monohydrogen Tetrametaphosphate Methyl Ester 3

A method of preparing a monohydrogen tetrametaphosphate organic ester can include adding a reagent, such as an alcohols (ROH), a nucleoside (2-deoxyadenosine, adenosine, and so on), an amino acid (such as an Fmoc-serine), or a steroid (such as a cholesterol) to a tetrametaphosphate anhydride. The monohydrogen tetrametaphosphate organic ester can include a monohydrogen tetrametaphosphate methyl ester.

Treatment of 2 with $H_2O$-containing acetone (<0.5 w/w %) at 23° C. regenerates 1 in quantitative in situ yield and in a 68% isolated yield. The reaction likely occurs through nucleophilic attack of $H_2O$ on the phosphoanhydridic P—O—P bridge. In a similar manner, the P—O—P bridge of 2 can also be cleaved by other hydroxy nucleophiles such as methanol, yielding an acidic tetrametaphosphate methyl ester. The reaction of 2 with 50 equivalents of methanol at 23° C. afforded within 30 min the quantitative formation of methanolysis product $[(P_4O_{10})(OH)(OMe)]^{2-}$ (3). The $^{31}P\{^1H\}$ NMR spectrum of 3 revealed a triplet at −24.6 ppm for the methoxyl bonded phosphorus and multiplet signals from −25.3 to −26.4 ppm for the other three phosphorus atoms due to the fast migration of the proton. Collecting the $^{31}P\{^1H\}$ NMR spectrum of 3 at −30° C. resolved the multiplet signal into two triplets at −26.2 and 27.2 ppm in a 1:2 ratio corresponding to the P—OH and P—O⁻ moieties, respectively. In the $^1H$ NMR spectrum, a broad signal at 13.2 ppm is assigned to the hydroxyl group, and a doublet at 3.78 ppm ($^3J_{hp}$=12 Hz) corresponded to the methoxy protons. This assignment was further supported by a doublet at 54.4 ppm ($^2J_{cp}$=6 Hz) observed by $^{13}C$ NMR spectroscopy.

Figure 3:
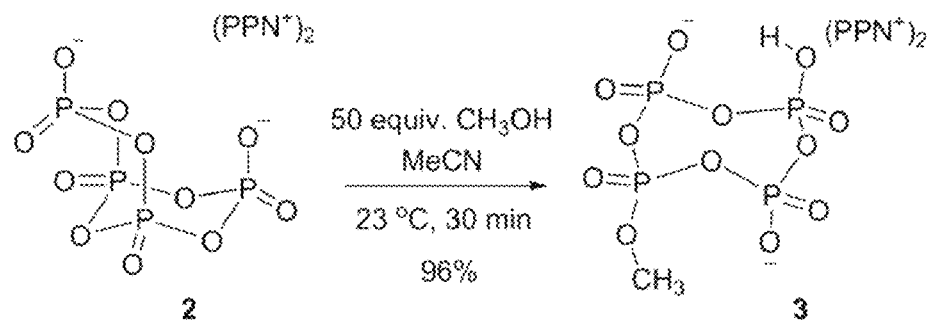
FIG. 3 shows methanolysis of 2 to monohydrogen tetrametaphosphate methyl ester 3.

FIG. 3 shows methanolysis of 2 to monohydrogen tetrametaphosphate methyl ester 3.

Figure 4:
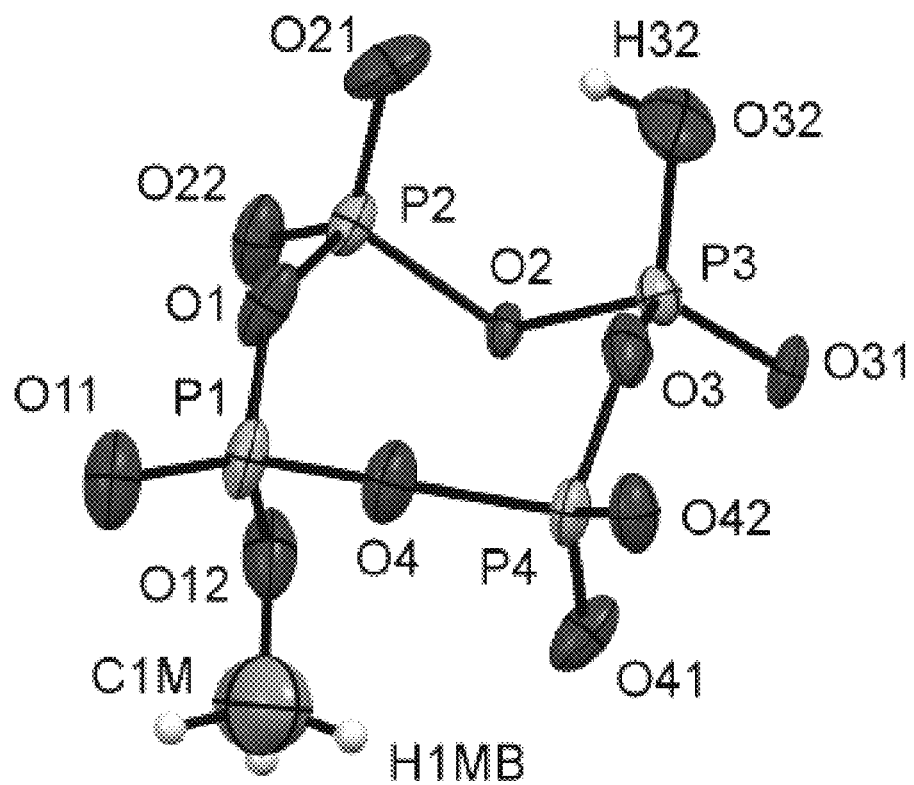
FIG. 4 shows solid state molecular structure of $[(P_4O_{10})(OH)-(OMe)]^{2-}$ (3) with ellipsoids at the 30% probability level and [PPN]+ cations omitted for clarity.

The solid-state structure of 3 was determined by single-crystal X-ray crystallography and is shown in FIG. 4. The proton and methyl groups are positioned on the 1,5-disposed phosphorus atoms. Intramolecular hydrogen bonding between the hydroxyl and neighboring P—O⁻ bond was observed, with a P—O . . . H distance of 1.841 Å, which is slightly shorter than that observed in the solid-state structure of 1.

FIG. 4 shows solid state molecular structure of $[(P_4O_{10})(OH)(OMe)]^{2-}$ (3) with ellipsoids at the 30% probability level and $[PPN]^+$ cations omitted for clarity.

Representative interatomic distances [Å] and angles [°] in 3: P1-O11 1.455(10), P1-O12 1.464(6), O12-C1M 1.358(12), P1-O1 1.509(6), P2-O21 1.473(6), P2-O22 1.488(7), P3-O31 1.451(7), P3-O32 1.535(6); C1M-O12-P1 115.4(8), P1-O1-P2 140.8(3), P3-O2-P2 122.0(4), P1-O4-P4 140.3(9), P3-O3-P4 134.3(3).

Preparation of Metal Tetrametaphosphate Complexes

A method of preparing a metal tetrametaphosphate complex can include adding a metal salt to a dihydrogen tetrametaphosphate in a solvent, such as an acetonitrile, an acetone, or a dichloromethane.

Since 1 can be delivered in anhydrous form and is soluble in organic solvents, it is uniquely suitable for synthesizing metal tetrametaphosphate complexes by protonolysis leading to replacement of simple basic ligands. Moreover, due to its diacidic nature 1 is commensurate for reaction with metals in the +2 oxidation state. The reactivity of 1 can be tested with a pair of metal (II) bis(hexamethyldisilazide) complexes, these reactions leading to new binary metal(II) tetrametaphosphate systems.

Figure 5:
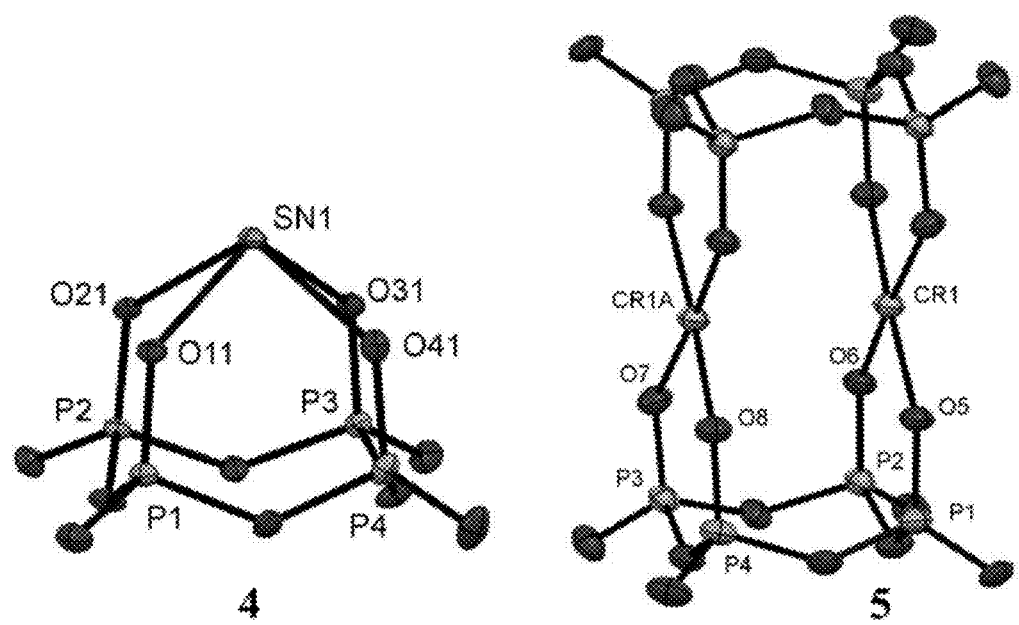
FIG. 5 shows solid-state molecular structures of $[Sn(P_4O_{12})]^{2-}$ (4) and $[Cr_2(P_4O_{12})_2]^{4-}$ (5) with ellipsoids at the 50% probability level and [PPN]+ cations and solvent molecules omitted for clarity.
Figure 6:
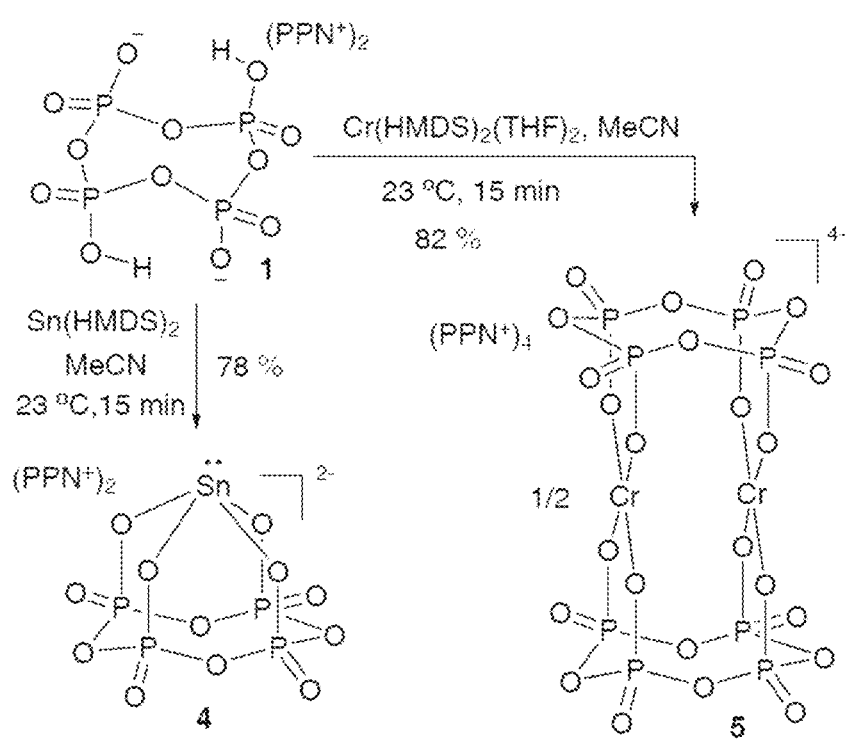
FIG. 6 shows syntheses of tin(II) k$^4$ tetrametaphosphate 4 and binary dimeric chromium(II) tetrametaphosphate dimer 5 from 1.

The reaction of 1 with 1 equivalent of $Sn(HMDS)_2$ (HMDS=hexamethyldisilazide) in acetonitrile at 23° C. can afford within 15 min a new species 4 showing a singlet in its $^{31}P\{^1H\}$ NMR spectrum at −23.54 ppm, which is slightly downfield from that of 1 (FIG. 6). $^{119}Sn$ NMR spectroscopy revealed a singlet at −800.57 ppm, consistent with the coordination of the cyclic phosphate to the tin center. As the reaction generates only the volatile $HN(SiMe_3)_2$ as byproduct, the PPN salt of 4 can be easily isolated as analytically pure solid with the formula $[PPN]_2[Sn(P_4O_{12})]$ in 78% yield. Its structure was established by an X-ray diffraction study to be a $C_{4v}$ symmetric tin(II) $\kappa^4$ tetrametaphosphate (FIG. 5). The tin vertex is centered above the four-membered face consisting of four oxygen atoms, resulting in a tetragonal pyramidal geometry. The Sn—O distances were found to be in the range of 2.1876(17) to 2.2240(16) Å. The O—Sn—O angles between neighboring phosphates are quite similar to each other varying from 74.65(3) to 75.90(4)°. The O—Sn—O angles between opposite phosphates are 119.82 and 120.05°, respectively. Previous reports of tin(II) in a similar C$_{4v}$ all-oxygen binding site was found in tungstostan-nate(II) heteropolyanions and tridentate alkoxyl tin(II) clusters. See, for example, Chorghade, G. S.; Pope, M. T. *J. Am. Chem. Soc.* 1987, 109, 5134-5138; Boyle, T. J.; Segall, J. M.; Alam, T. M.; Rodriguez, M. A.; Santana, J. M. *J Am. Chem. Soc.* 2002, 124, 6904-6913, each of which is incorporated by reference in its entirety. 4 is likely the first example of κ tetrametaphosphate coordination mode. The lone pair electrons at the tin(II) center can be localized in an orbital very rich in s character in view of Bent's rule considerations and therefore relatively non-nucleophilic/basic in character. See, for example, Bent, H. A. *Chem. Rev.* 1961, 61, 275-311, which is incorporated by reference in its entirety.

FIG. 6 shows syntheses of tin(II) k$^4$ tetrametaphosphate 4 and binary dimeric chromium(II) tetrametaphosphate dimer 5 from 1.

The reactivity of 1 toward the chromium(II) amide Cr(HMDS)$_2$(THF)$_2$ can be examined. See, for example, Bradley, D. C; Hursthouse, M. B.; Newing, C. W.; Welch, A. *J. Chem. Commun.* 1972, 567-568; Frazier, B. A.; Wolczanski, P. T.; Lobkovsky, E. B. *Inorg. Chem.* 2009, 48, 11576-11585, each of which is incorporated by reference in its entirety. Addition of 1 equivalent of 1 to the purple brown solution of Cr(HMDS)$_2$(THF)$_2$ at 23° C. can rapidly afford a pale-green solution. The $^{31}$P{$^1$H} NMR spectrum of this new species is silent in the phosphate region, suggesting that the tetrametaphosphate is coordinated to a paramagnetic chromium(II) center. After workup, a pale grey solid can be isolated in 82% yield. The solid-state structure of 5 was identified as a binary dimeric chromium(II) tetrametaphosphate dimer [Cr$_2$(P$_4$O$_{12}$)$_2$]$_4$- (5) (FIG. 6, FIG. 5) by X-ray diffraction. Each chromium adopts a square planar geometry by coordinating to the oxygen lone pairs of two tetrametaphosphate ligands. The Cr . . . Cr distance of 2.902 Å suggests a very weak Cr Cr interaction. See, for example, Pyykkoe, P.; Atsumi, M. *Chem. Eur. J.* 2009, 15, 12770-12779; Cotton, F. A.; Extine, M.; Rice, G. W. *Inorg. Chem.* 1978, 17, 176-186, each of which is incorporated by reference in its entirety. Compound 5 represents a binary metal (II) tetrametaphosphate dimer. In the case of other k$^2$ tetrametaphosphate complexes, such as those bearing d$^8$ Rh and Ir centers, invariably only one tetrametaphosphate ligand is involved with two metal moieties bonded on either side of the P$_4$O$_4$ mean plane.

FIG. 5 shows solid-state molecular structures of [Sn (P$_4$O$_{12}$)]$^{2-}$ (4) and [Cr$_2$(P$_4$O$_{12}$)$_2$]$^{4-}$ (5) with ellipsoids at the 50% probability level and [PPN]+ cations and solvent molecules omitted for clarity. Representative interatomic distances [A] and angles [°] in 4: Sn1-O11 2.2259(9), Sn1-O21 2.2068(10), Sn1-O31 2.2231(10), Sn1-O41 2.1886 (10); O41-Sn1-O21 119.82(4), O31-Sn1-O11 120.05(3), O21-Sn1-O11 74.65(3), O21-Sn1-O31 75.78(3), O41-Sn1-O31 75.66(4), O41-Sn1-O11 75.90(4). Representative interatomic distances [A] and angles [°] in 5: Cr1-O5 1.976(3), Cr1-O6 1.981(3), Cr1A-O7 1.989(4), Cr1-O8 1.976(3); O5-Cr1-O6 88.61(11), O8-Cr1A-O7 88.77(14).

Dihydrogen tetrametaphosphate [P$_4$O$_{12}$H$_2$]2$^-$ (1), can be prepared in high yield under benchtop conditions requiring no special equipment. This diacid dianion can serve as a robust and versatile precursor to numerous derivatives. The synthesis of anhydride 2 and ester 3 can be adapted to access tetrametaphosphate amino acids or nucleosides, which can potentially serve as valuable reagents opening the door to a new class of biologically important molecules. The reaction with metal amides can result in unconventional monomeric k$^4$ and dimeric k$^2$ species 4 and 5. A broad family of metal tetrametaphosphate derivatives can be accessed by the protolytic method illustrated herein.

Surface Functionalization of a Substrate

Phosphorylation of substrates can enhance the properties of the substrates and form new compositions of matter. By phosphorylation, it can create O-substituted phosphate (R—OPO$_3$) groups on the surface of a solid substrate. Metaphosphoric acid (HO—PO$_2$) and metaphosphates (R—OPO$_2$) can be useful sources of phosphate groups, since they are reactive, especially to hydroxyl groups.

Suitable substrates can comprise any material having pendant hydroxyl groups at the surface. For example, the substrate can include silica gel, zeolites, cellulosic material, and so on.

In addition, a process for phosphorylating a solid substrate having surface hydroxyl groups can include contacting the surface of said substrate with a solution. The solution can include an anhydride, such as a tetrametaphosphate anhydride. The solution can include a compound comprising a R—OPO$_2$ group, where R is a straight or branched, saturated or unsaturated alkyl group containing 1 to 60 carbon atoms, wherein the alkyl group optionally contains a linkage of the formula —O—, —S—, —NH—, —C(O)—, —C(O)O—, OC(O)—, —C(O)NH—, or —HNC(O)—, and is optionally substituted with —CN, —Cl, —Br, —F, aryl, aryloxy, heterocyclic or cyclo-C$_3$-C$_8$-alkyl; or R$^1$ is aryl, heterocyclic, cyclo-C$_3$-C$_8$-alkyl, or bicyclic, tricyclic or polycyclic alkyl, and is optionally substituted with —CN, —Cl, —Br, —F, phenyl, benzyl, or straight or branched, saturated or unsaturated alkyl or alkoxy containing up to 12 carbon atoms, the optional phenyl, benzyl, alkyl and alkoxy being optionally substituted with —CN, —Cl, —Br, —F, or C$_1$-C$_6$ alkyl.

EXAMPLE

General Methods

Unless stated otherwise, all manipulations were performed using standard Schlenk techniques or in a glove box equipped with an atmosphere of purified nitrogen. Bis (triphenylphosphine chloride ([PPN]Cl) was purchased from BOC SCIENCES. [PPN]$_4$[P$_4$O$_{12}$].5H$_2$O, Sn(HMDS)$_2$, and Cr(HMDS)$_2$(THF)$_2$ (HMDS=hexamethyldisilazide) were prepared according to reported procedures. See, for example, Kamimura, S.; Kuwata, S.; Iwasaki, M.; Ishii, Y. *Inorg. Chem.* 2004, 43, 399-401; Schaeffer, C. D.; Myers, L. K.; Coley, S. M.; Otter, J. C; Yoder, C. H. *J. Chem. Educ.* 1990, 61, 347; Frazier, B. A.; Wolczanski, P. T.; Lobkovsky, E. B. *Inorg. Chem.* 2009, 48, 11576-11585, each of which is incorporated by reference in its entirety. Aqueous solutions were prepared using reagent grade deionized water (p>18 Mfkm; Ricca Chemical Company, USA). Dicyclohexylcarbodiimide (DCC) was purchased from Sigma Aldrich and used as received. Acetone (H$_2$O content <0.5 w/w %) was purchased from Macron Fine Chemicals and used as received. Acetonitrile, diethyl ether, methanol, THF and pentane were purified on a Glass Contour Solvent Purification System built by SG Water USA, LLC and stored with 4 Å molecular sieves. Molecular sieves (4 Å) were dried at 50 mTorr overnight at a temperature above 200° C. IR spectra were recorded on a Bruker Tensor 37 Fourier transform IR (FT-IR) spectrometer. Elemental analyses were performed by Robertson Microlit Laboratories, Inc. NMR solvents were obtained from Cambridge Isotope Laboratories and dried using standard literature techniques. 1H, $^{13}$C{$^1$H}, $^{31}$P{$^1$H} and $^{119}$Sn NMR spectra were recorded on either a Varian Mercury-300 or a Bruker AVANCE-400 spectrometer. $^1$H and $^{13}$C{$^1$H} NMR chemical shifts are reported in ppm relative to tetramethylsilane (TMS) and are referenced to the solvent peaks. $^{31}$P{$^1$H} NMR chemical shifts are reported with respect to an external reference (85% $H_3PO_4$, 50.0 ppm). $^{119}$Sn NMR chemical shifts are reported with respect to an external reference ($Me_4Sn$ 90% in $C_6D_6$, δ 0.0 ppm).

Preparation of Dihydrogen Tetrametaphosphate (as its PPN salt) $[PPN]_2[P_4O_{12}H_2]([PPN]_2[1])$ Path 1: $[PPN]_4[P_4O_{12}].5H_2O$ with $(CF_3CO)_2O$ Under open air conditions in a fume hood, $[PPN]_4[P_4O_{12}]$ .5H$_2$O (4.227 g, 1.670 mmol, 1.0 equiv.) was suspended in 40 mL of commercial acetone. To this stirring suspension was added dropwise a solution of $(CF_3CO)_2O$ (240 μL, 1.700 mmol, 1.02 equiv.) in acetone (10 mL). After addition of ca. 50% of the $(CF_3CO)_2O$ solution, white precipitate began to crash out of the reaction mixture. After complete addition of the $(CF_3CO)_2O$ solution, the suspension was allowed to stir for a total of 40 minutes to allow complete precipitation of $[PPN]_2[P4O_{12}H_2]$. The solids were then collected by filtration on a medium porosity fritted funnel, washed with acetone (10 mL), and dried in vacuo affording $[PPN]_2[1]$ as a white solid (Yield: 2.194 g, 1.572 mmol, 94%). The material obtained in this way was both analytically pure and free of any observable quantity of trifluoroacetate according to $^{19}$F NMR spectroscopic analysis.

Path 2: $[PPN]_4[P_4O_{12}].5H_2O$ with $Tf_2O$

In a glove box, $[PPN]_4[P_4O_{12}].5H_2O$ (1.003 g, 0.39 mmol, 1.0 equiv.) was dissolved in 8 mL of acetonitrile. To this stirring suspension was added dropwise a solution of $Tf_2O$ (66 μL, 0.39 mmol, 1.0 equiv.) in acetonitrile (2 mL). The reaction mixture was kept stirring at room temperature for 20 min. All volatile materials were then removed in vacuo to yield a white solid, to which was added THF (20 mL), and the suspension was allowed to stir at room temperature for 1 h. The solids were then collected by filtration using a medium porosity fritted funnel, thoroughly washed with THF (6×6 mL), diethyl ether (3×3 mL), THF (6×6 mL), and diethyl ether (3×3 mL), respectively. The resulting white solid was dried in vacuo affording $[PPN]_2$ $[P_4O_{12}H_2]$ ($[PPN]_2[1]$) as white powder (Yield: 459.6 mg, 0.33 mmol, 84%).

Path 3: $[PPN]_2[P_4O_{11}]$ with $H_2O$ In a glove box, $[PPN]_2$ $[P_4O_{11}]$ ($[PPN]_2[2]$) (96.0 mg, 0.07 mmol) was loaded into a 20 mL vial which was then brought outside of the glove box into a fume hood. To the vial was added unpurified acetone (3 mL) at room temperature affording a colorless solution. An aliquot of the solution was examined by $^{31}$P NMR spectroscopy, which revealed the quantitative conversion of $[PPN]_2[P_4O_{11}]$ ($[PPN]_2[2]$) to $[PPN]_2[P_4O_{12}H_2]$ ($[PPN]_2[1]$). After keeping the solution at room temperature for ca. 1 h, colorless block crystals started to form. The solution was allowed to stand undisturbed at room temperature for 48 h to complete the crystallization. The mother liquor was then decanted away and the crystals were dried in vacuo and subsequently crushed into white powder, which was further washed with pentane (4×2 mL) and dried in vacuo affording $[PPN]_2[1]$ as a white solid (Yield: 66 mg, 0.047 mmol, 68%).

Characterization of $[PPN]_2[P_4O_{12}H_2]$ ($[PPN]_2[1]$)

ESI-MS(-)($CH_3CN$, m/z): 318.8122 ($[P_4O_{12}H_2]^{2-}$+H+), 158.8814 ($[P_4O_{12}H_2]^{2-}$). IR (ATR, cm$^{-1}$): ν 1270 (s, P=O), 1022 (s, P—O—), 996 (s, P—O). $^1$H NMR (CD$_3$CN, 300 MHz, ppm) δ: 14.03 (br, 2H, OH), 7.51-7.69 (m, 60H, Ph). $^{31}$P{$^1$H} NMR (CD$_3$CN, 122 MHz, ppm) δ: 22.10 (s, 4P, [PPN]$^+$), −25.60 (s, 4P). $^{13}$C NMR (CD$_3$CN, 75 MHz, ppm): δ: 133.62 (s), 132.26 (m), 129.39 (m), 127.78 (s), 126.69 (s). Anal. Calcd for $C_{72}H_{62}N_2O_{12}P_8$ (1395.08): C, 61.99; H, 4.48; N, 2.01%. Found: C, 61.95; H, 4.64; N, 2.04%.

Figure 7:
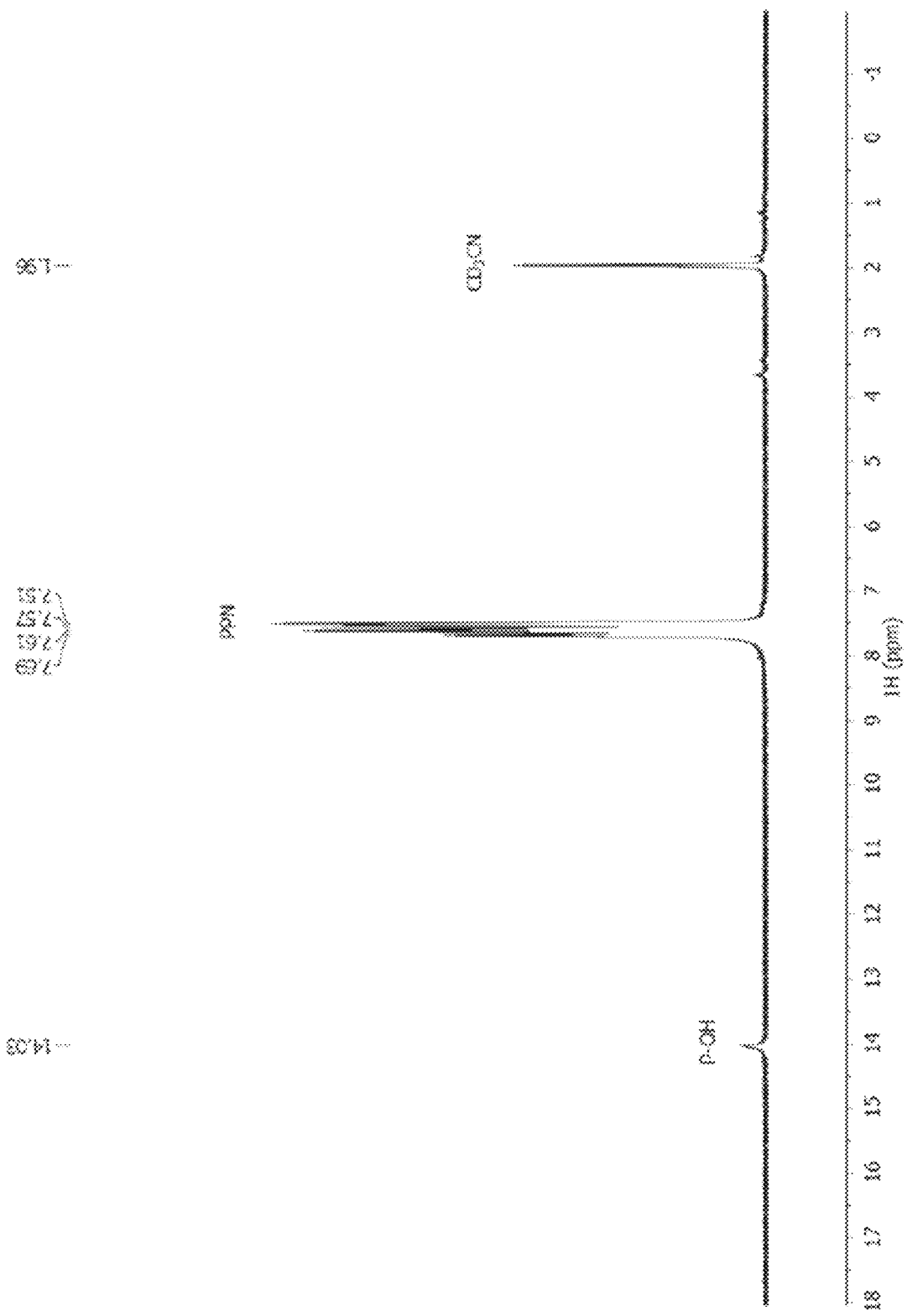
FIG. 7 shows 1H NMR (300 MHz) spectrum of the PPN salt of $[P_4O_{12}H_2]^{2-}$ (1) recorded at 23° C. in $CD_3CN$.
Figure 8:
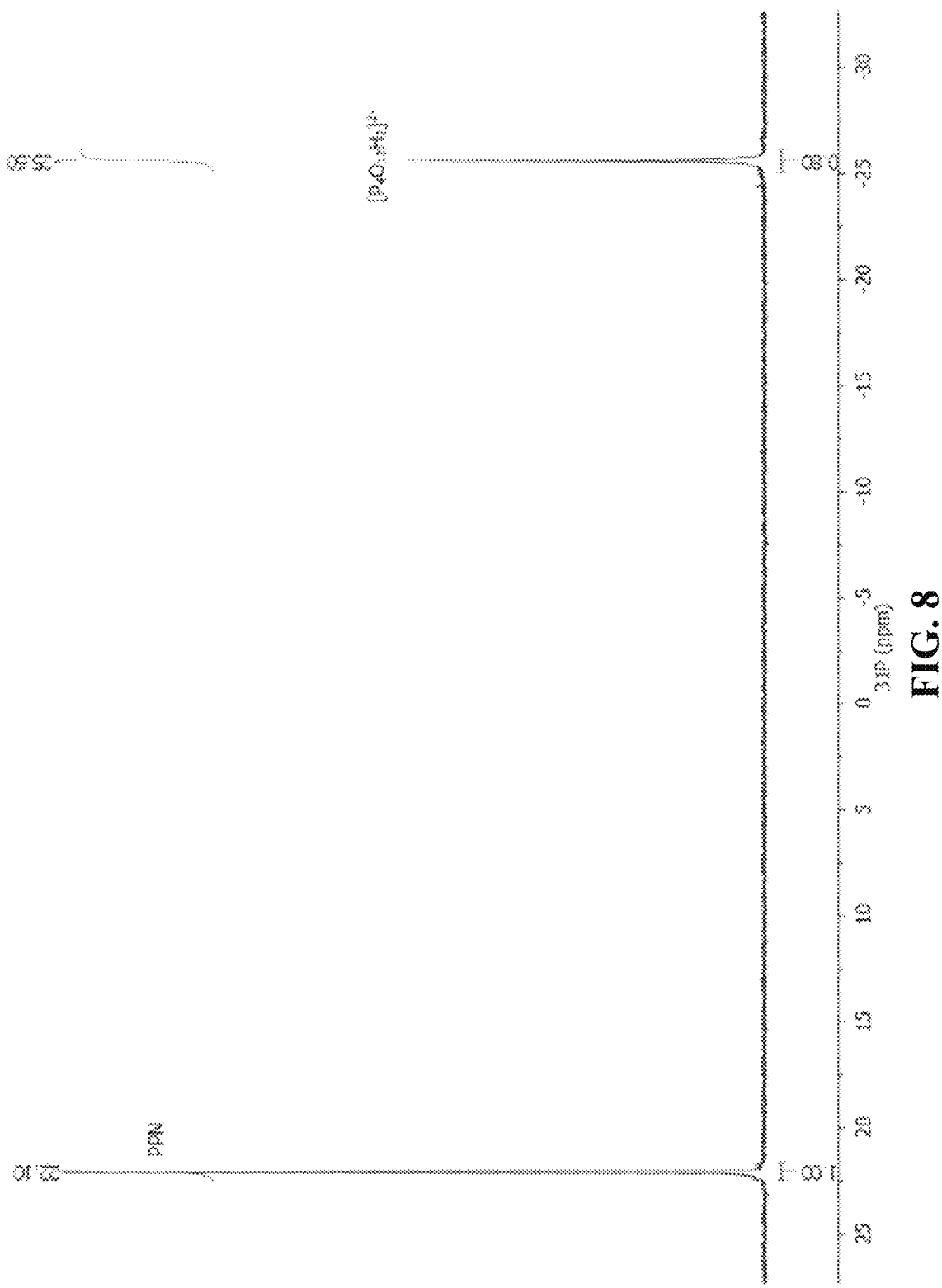
FIG. 8 shows $^{31}P\{^1H\}$ NMR (122 MHz) spectrum of the PPN salt of $[P_4O_{12}H_2]^{2-}$ (1) recorded at 23° C. in $CD_3CN$.
Figure 9:
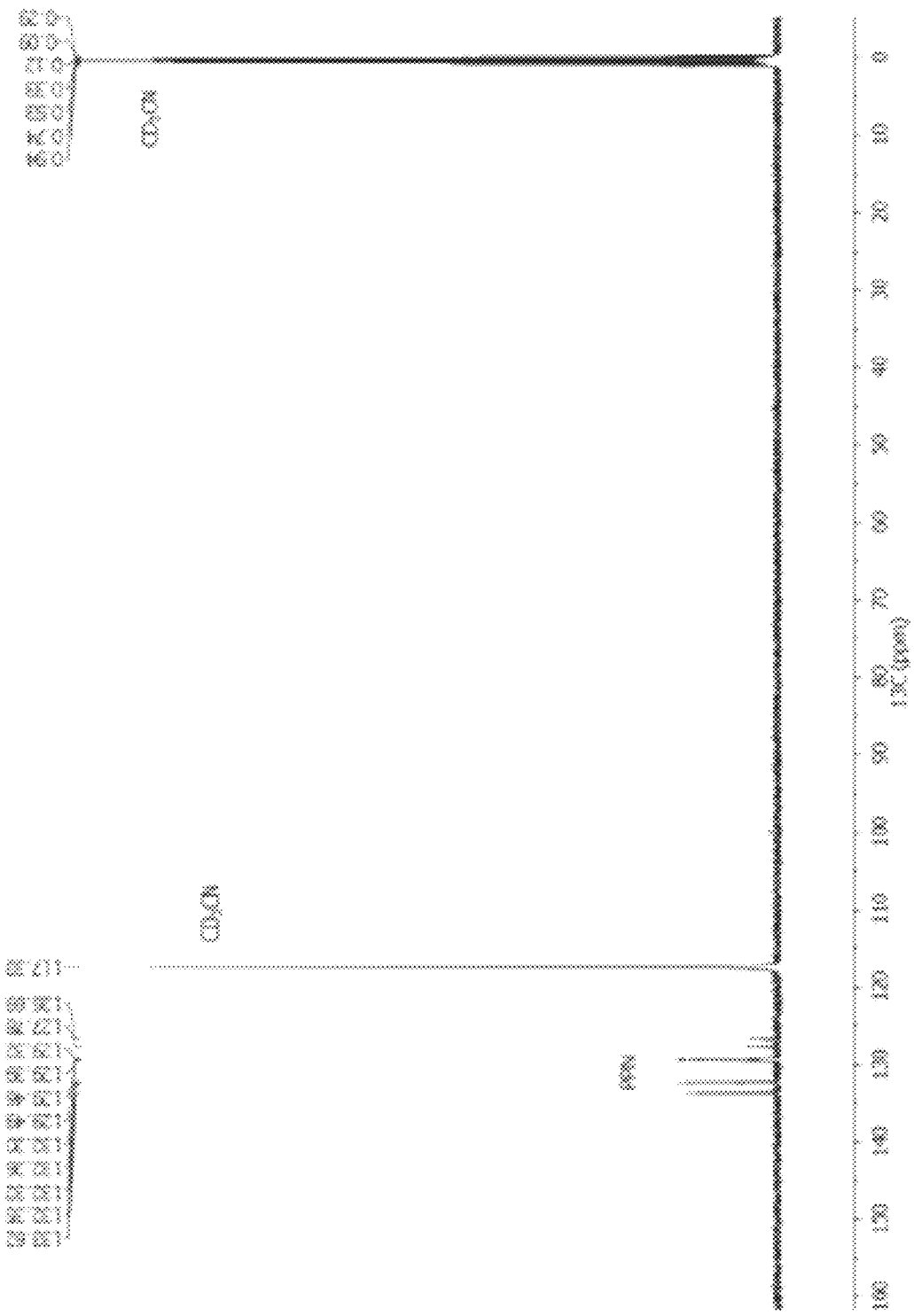
FIG. 9 shows $^{13}C$ NMR (75 MHz) spectrum of [the PPN salt of $[P_4O_{12}H_2]^{2-}$ (1) recorded at 23° C. in $CD_3CN$.
Figure 10:
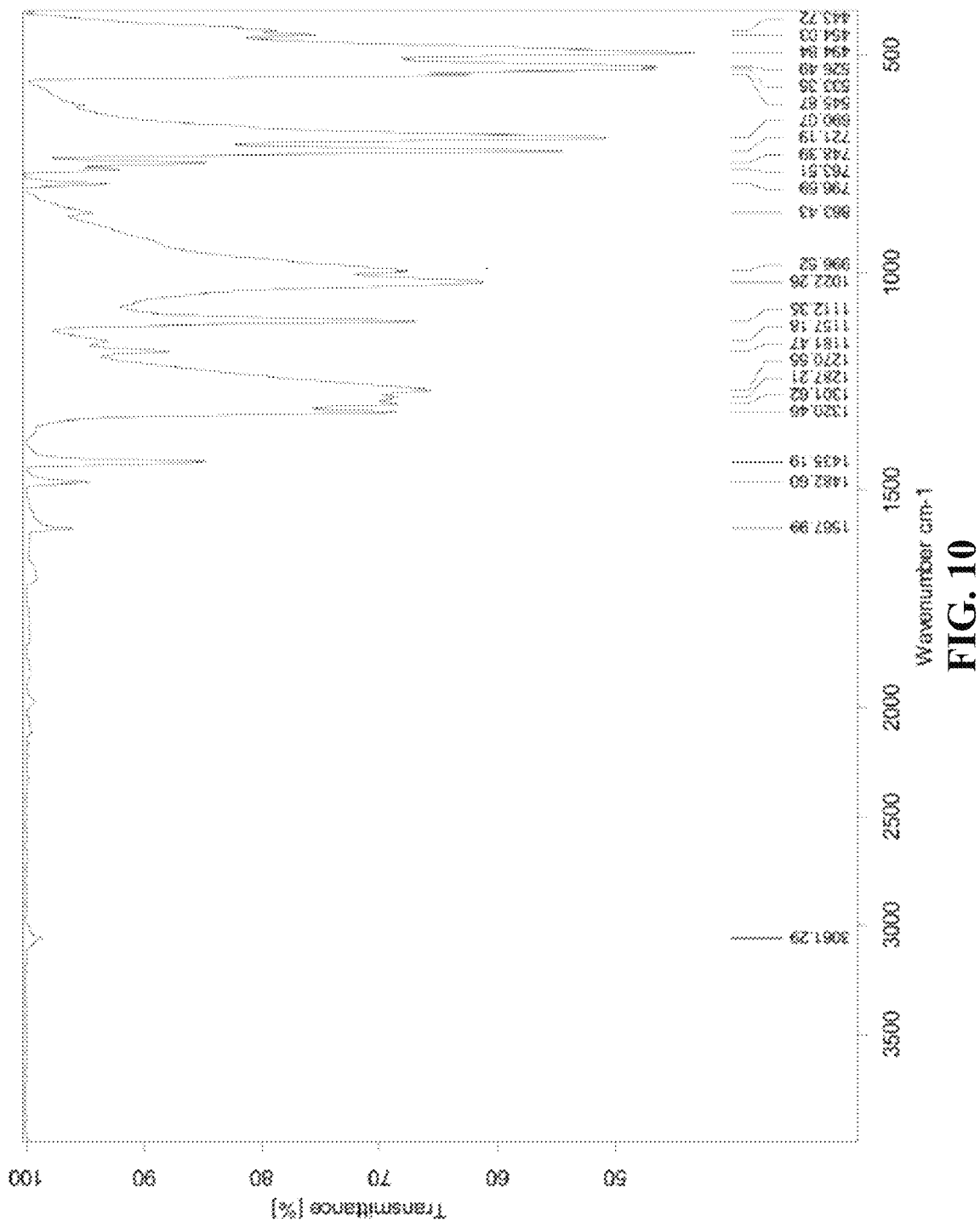
FIG. 10 shows ATR-IR spectrum of solid $[PPN]_2[P_4O_{12}H_2]$ ($[PPN]_2[1]$).
Figure 11:
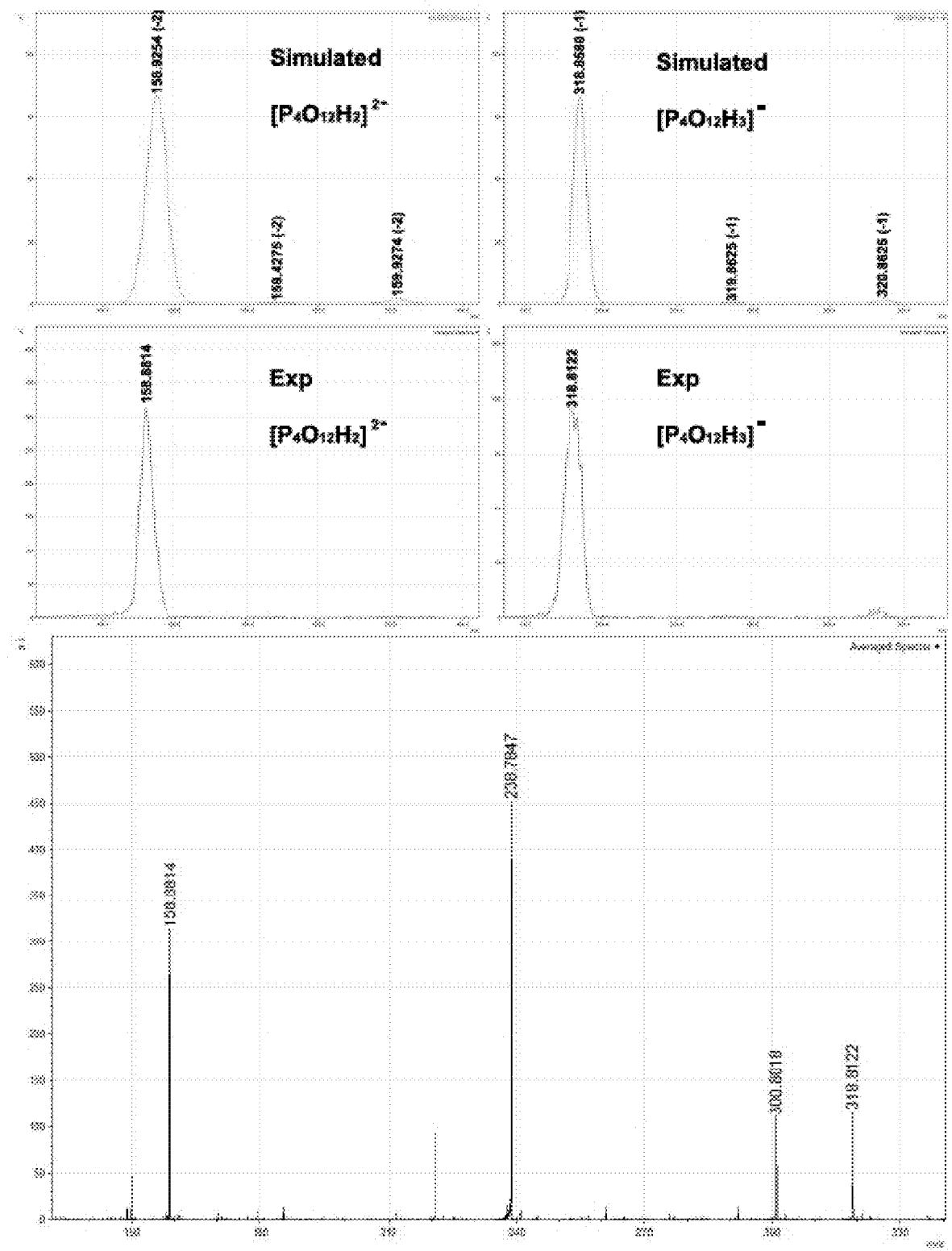
FIG. 11 shows ESI-MS(−) spectrum of [− the PPN salt of $[P_4O_{12}H_2]^{2-}$ (1).

FIG. 7 shows $^1$H NMR (300 MHz) spectrum of $[PPN]_2$ $[P_4O_{12}H_2]$ ($[PPN]_2[1]$) recorded at 23° C. in CD$_3$CN. FIG. 8 shows $^{31}$P {$^1$H} NMR (122 MHz) spectrum of $[PPN]_2$ $[P_4O_{12}H_2]$ ($[PPN]_2[1]$) recorded at 23° C. in CD$_3$CN. FIG. 9 shows $^{13}$C NMR (75 MHz) spectrum of $[PPN]_2[P_4O_{12}H_2]$ ($[PPN]_2[1]$) recorded at 23° C. in CD$_3$CN. FIG. 10 shows ATR-IR spectrum of solid $[PPN]_2[P_4O_{12}H_2]$ ($[PPN]_2[1]$). FIG. 11 shows ESI-MS(-) spectrum of $[PPN]_2[P_4O_{12}H_2]$ ($[PPN]_2[1]$).

Preparation of Tetrametaphosphate Anhydride (as its PPN Salt) $[PPN]_2[P_4O_{11}]$($[PPN]_2[2]$)

Path: $[PPN]_2[P_4O_{12}H_2]$ with DCC

In a glove box, $[PPN]_2[P_4O_{12}H_2]$ (320.2 mg, 0.230 mmol, 1 equiv.) and DCC (47.6 mg, 0.231 mmol, 1.01 equiv.) were mixed in dry acetonitrile (5 mL) affording a white suspension due to the production of the byproduct dicyclohexylurea (DCU), which is insoluble in acetonitrile. The reaction mixture was allowed to stir at room temperature for 30 minutes. The mixture then was filtered through a glass microfiber filter and the volatile materials were removed in vacuo from the filtrate to give a white solid, which was then washed with THF (3×3 mL), diethyl ether (3×3 mL), and dried in vacuo to give $[PPN]_2[2]$ as white powder (Yield: 258.6 mg, 0.188 mmol, 82%).

Characterization of $[PPN]_2[P_4O_{11}]$ ($[PPN]_2[2]$)

ESI-MS (-)($CH_3CN$, m/z): 300.8838 (100%, $[P_4O_{11}]^{2-}$+ H+). IR (ATR, cm$^{-1}$): ν 1262 (s, P=O), 995 (s, P—O). $^1$H NMR (CD$_3$CN, 300 MHz, ppm) δ: 7.48-7.71 (m, 60H, Ph). $^{31}$P{$^1$H} NMR (CD$_3$CN, 161.9 MHz, ppm) δ: 21.96 (s, 4P, [PPN]$^+$), −24.40 (t, $^2$J$_{PP}$=29 Hz, 2P, A$_2$), −32.51 (t, $^2$J$_{PP}$=29 Hz, 2P, X$_2$). $^{13}$C NMR (CD$_3$CN, 100 MHz, ppm) δ: 133.61 (s), 132.26 (m), 129.38 (m), 127.78 (s), 126.71 (s). Anal. Calcd for $C_{72}H_{60}N_2O_{11}P_8$ (1377.07): C, 62.80; H, 4.39; N, 2.03%. Found: C, 62.56; H, 4.56; N, 2.03%.

Figure 12:
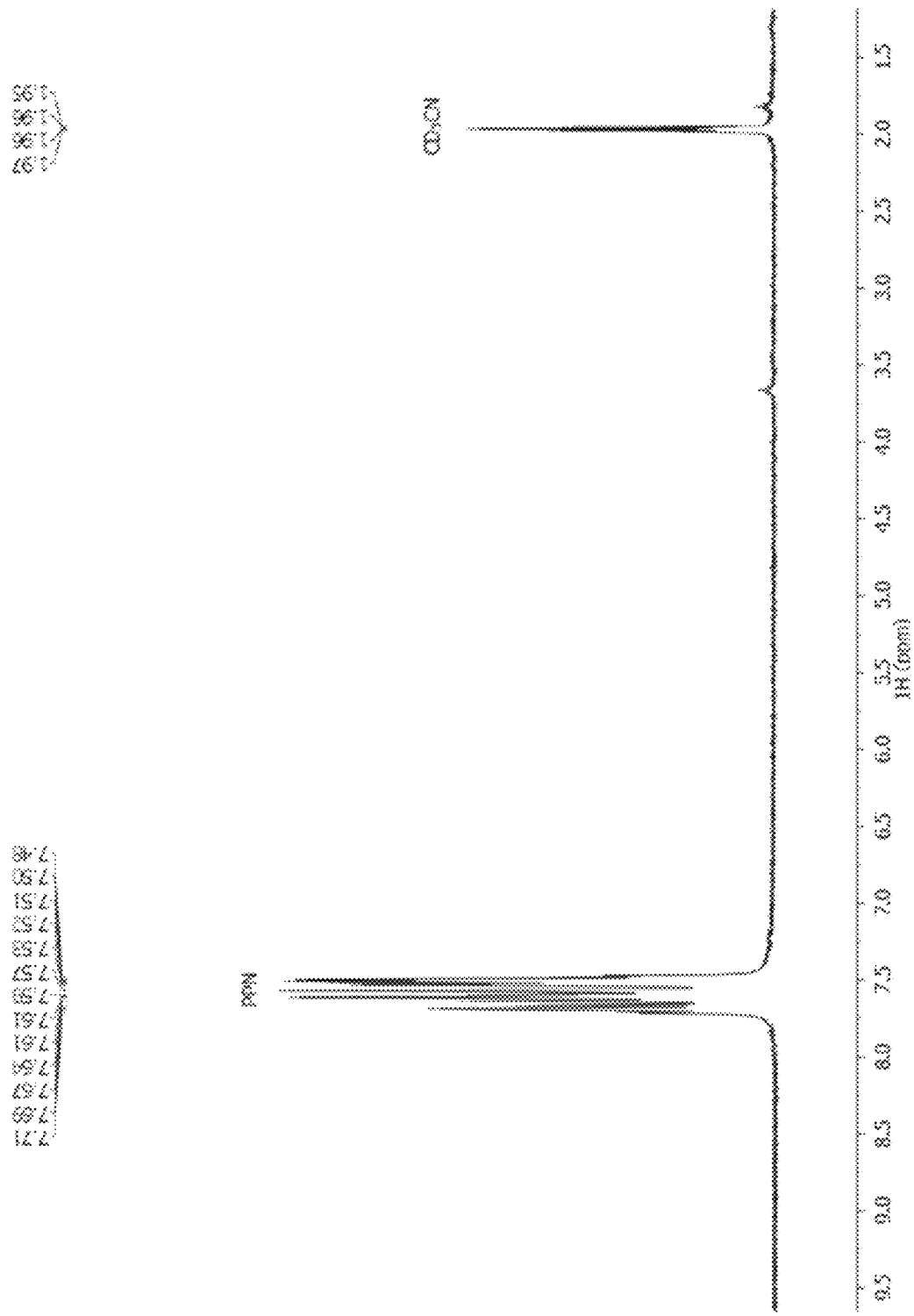
FIG. 12 shows $^1H$ NMR (300 MHz) spectrum of the PPN salt of $[P_4O_{11}]^{2-}$ (2) recorded at 23° C. in $CD_3CN$.
Figure 13:
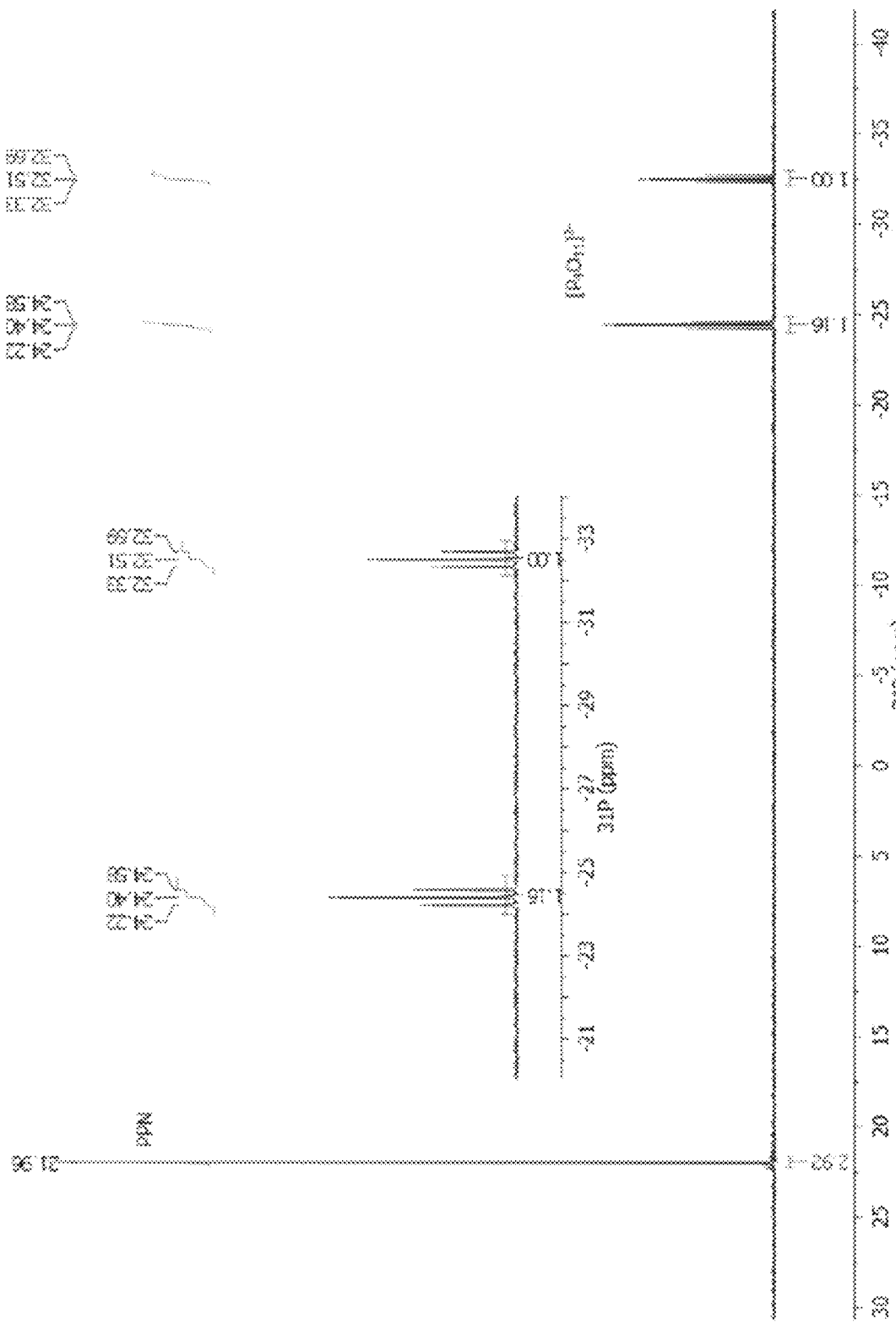
FIG. 13 shows $^{31}P\{^1H\}$ NMR (161.9 MHz) spectrum of the PPN salt of $[P_4O_{11}]^{2-}$ (2) recorded at 23° C. in $CD_3CN$.
Figure 14:
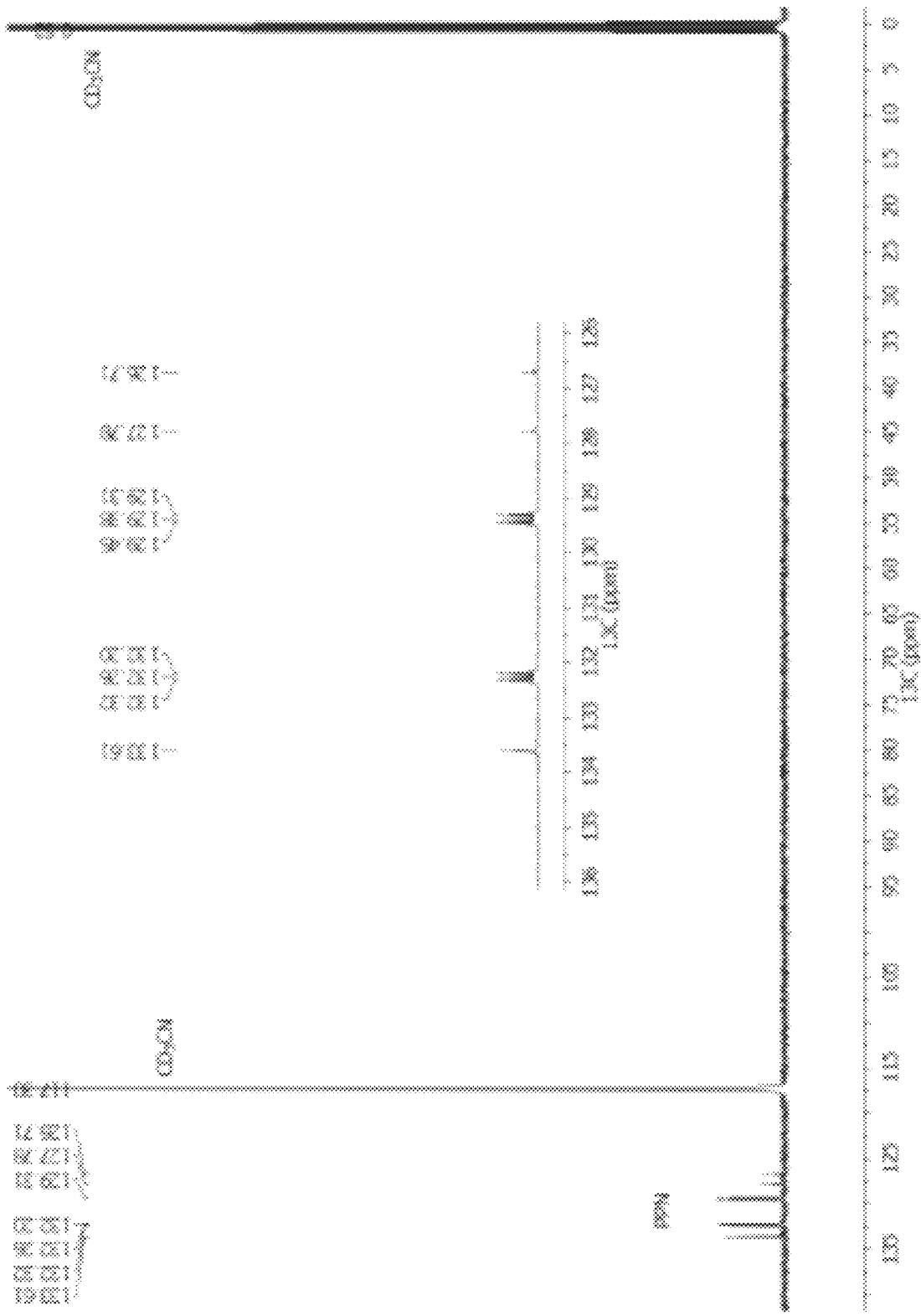
FIG. 14 shows $^{13}C$ NMR (100 MHz) spectrum of the PPN salt of $[P_4O_{11}]^{2-}$ (2) recorded at 23° C. in $CD_3CN$.
Figure 15:
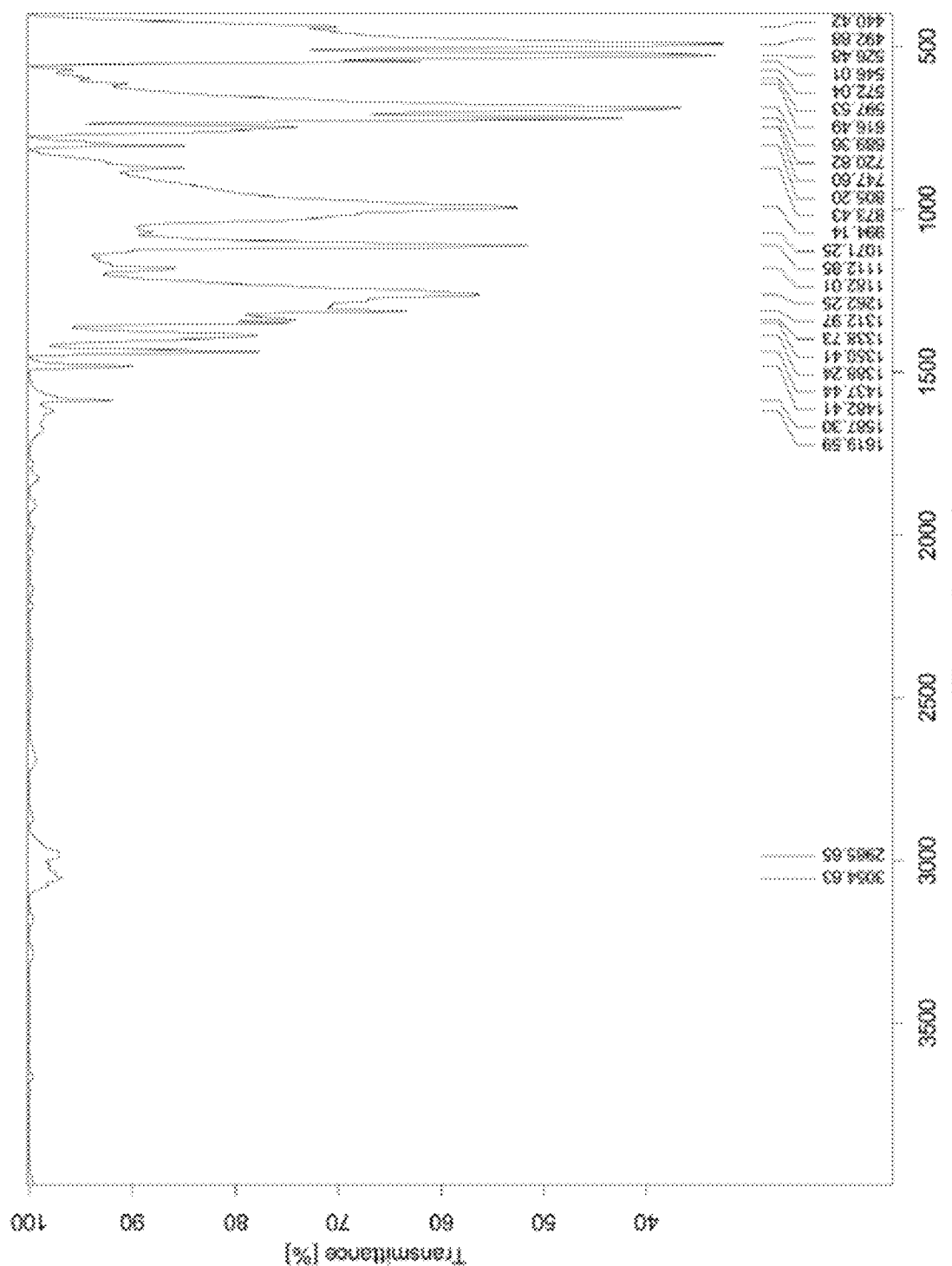
FIG. 15 shows ATR-IR spectrum of solid $[PPN]_2[P_4O_{11}]$ ($[PPN]_2[2]$).
Figure 16:
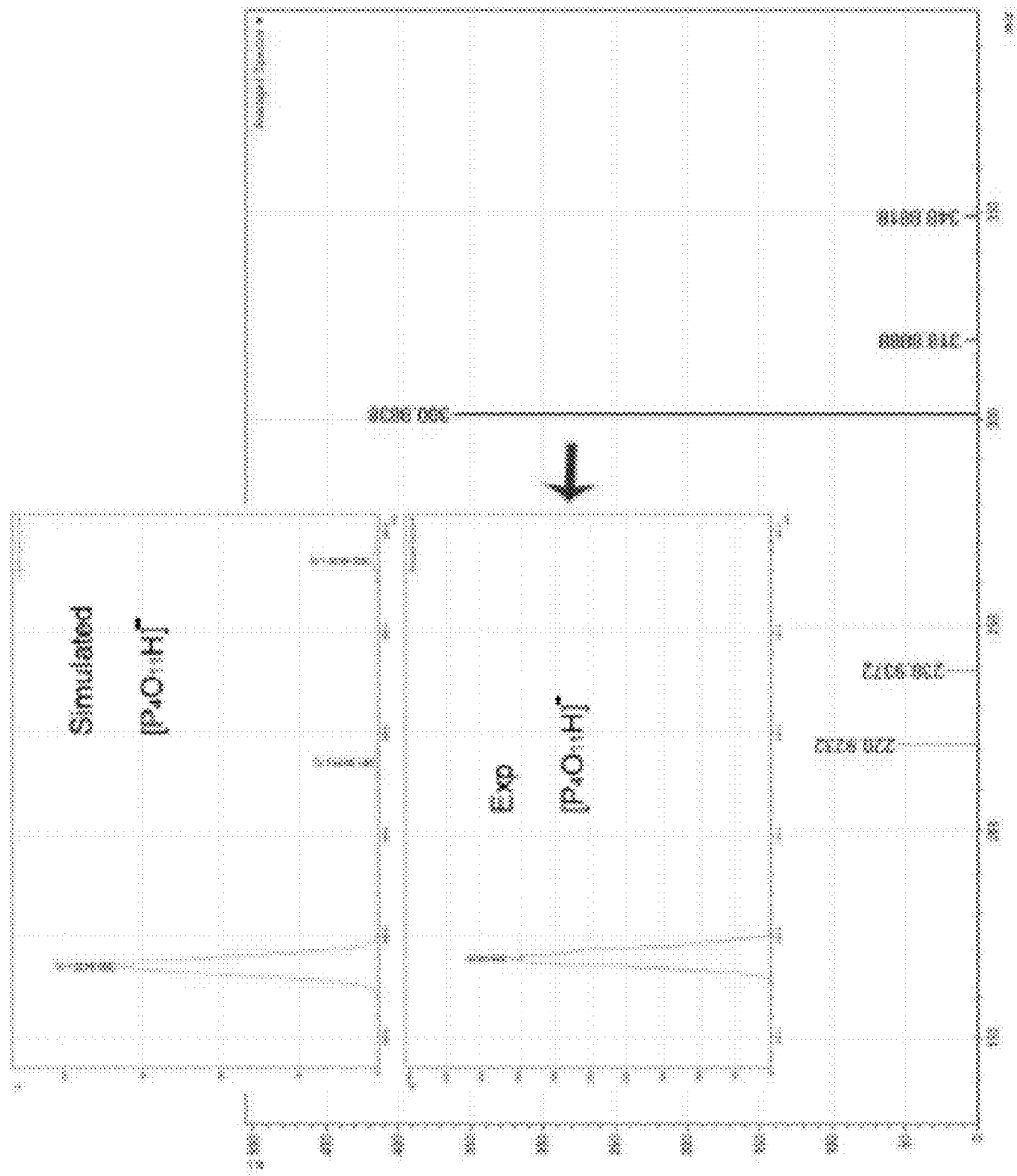
FIG. 16 shows ESI-MS(−) spectrum of the PPN salt of $[P_4O_{11}]^{2-}$ (2).

FIG. 12 shows $^1$H NMR (300 MHz) spectrum of $[PPN]_2$ $[P_4O_{11}]$ ($[PPN]_2[2]$) recorded at 23° C. in CD$_3$CN. FIG. 13 shows $^{31}$P{$^1$H} NMR (161.9 MHz) spectrum of $[PPN]_2$ $[P_4O_{11}]$ ($[PPN]_2[2]$) recorded at 23° C. in CD$_3$CN. FIG. 14 shows $^{13}$C NMR (100 MHz) spectrum of $[PPN]_2[P_4O_{11}]$ ($[PPN]_2[2]$) recorded at 23° C. in CD$_3$CN. FIG. 15 shows ATR-IR spectrum of solid $[PPN]_2[P_4O_{11}]$ ($[PPN]_2[2]$). FIG. 16 shows ESI-MS(-) spectrum of $[PPN]_2[P_4O_{11}]$ ($[PPN]_2$ [2]).

Preparation of Monohydrogen Tetrametaphosphate Methyl Ester (as its PPN Salt) $[PPN]_2$ $[(P_4O_{10})(OH)(OMe)]$ ($[PPN]_2$ [3])

Path: $[PPN]_2[P_4O_{11}]$ with Methanol

In a glove box, $[PPN]_2[P_4O_{11}]$ ($[PPN]_2[2]$) (180 mg, 0.131 mmol, 1 equiv.) was dissolved in dry acetonitrile (4 mL) and to the resulting solution was added dropwise dry methanol (200 μL, 4.9 mmol, 37 equiv.) affording a colorless solution. The reaction mixture was allowed to stir at ambient temperature for 30 min. An aliquot of the mixture was examined by $^{31}$P NMR spectroscopy revealing the quantitative formation of the desired $[PPN]_2[(P_4O_{10})(OH)(OMe)]$ ($[PPN]_2[3]$). All volatile materials were then removed in vacuo giving a sticky colorless residue, which was washed with diethyl ether (2×2 mL) and pentane (2×2 mL), and dried in vacuo affording $[PPN]_2[3]$ as white powder (Yield: 177.4 mg, 0.126 mmol, 96%).

Characterization of $[PPN]_2[(P_4O_{10})(OH)(OMe)]$ ($[PPN]_2$ [3])

ESI-MS(-)($CH_3CN$, m/z): 332.8115 ($[(P_4O_{10})(OH)(OMe)]^{2-}$+H+), 165.9093 ($[(P_4O_{10})$—(OH)(OMe)]$^{2-}$). IR (ATR, cm$^{-1}$): ν 3413 (br, OH), 1257 (br, P=O), 993 (s, P—O$^-$). $^1$H NMR (CD$_3$CN, 400.1 MHz, ppm). δ: 13.21 (br, 1H, OH), 7.48-7.70 (m, 60H, Ph), 3.77 (d, $^3J_{HP}$=12 Hz, CH$_3$). $^{31}$P{$^1$H} NMR (CD$_3$CN, 161.9 MHz, ppm) δ: 21.61 (s, 4P, [PPN]$^+$), −24.64 (t, $^2J_{PP}$=24 Hz, 1 P, P—OMe), −25.31 to −26.43 (m, 3P). VT $^{31}$P{$^1$H} NMR (MeCN, 161.9 MHz, ppm, −30° C.): 21.37 (s, 4P, [PPN]$^+$), −24.68 (t, $^2J_{PP}$=24 Hz, 1P, P—OMe), −26.15 (t, $^2J_{PP}$=24 Hz, 1P, P-OH), −27.18 (t, $^2J_{PP}$=24 Hz, 2P, P—O). $^{13}$C NMR (CD$_3$CN, 100 MHz, ppm) δ 133.72 (s), 132.28 (m), 129.48 (m), 127.77 (d), 126.70 (d), 54.38 (d, $^2J_{CP}$=6 Hz, CH$_3$). Anal. Calcd for C$_{73}$H$_{64}$N$_2$O$_{12}$P$_8$ (1409.1071): C, 62.22; H, 4.58; N, 1.99%. Found: C, 61.67; H, 4.95; N, 2.45%.

Figure 17:
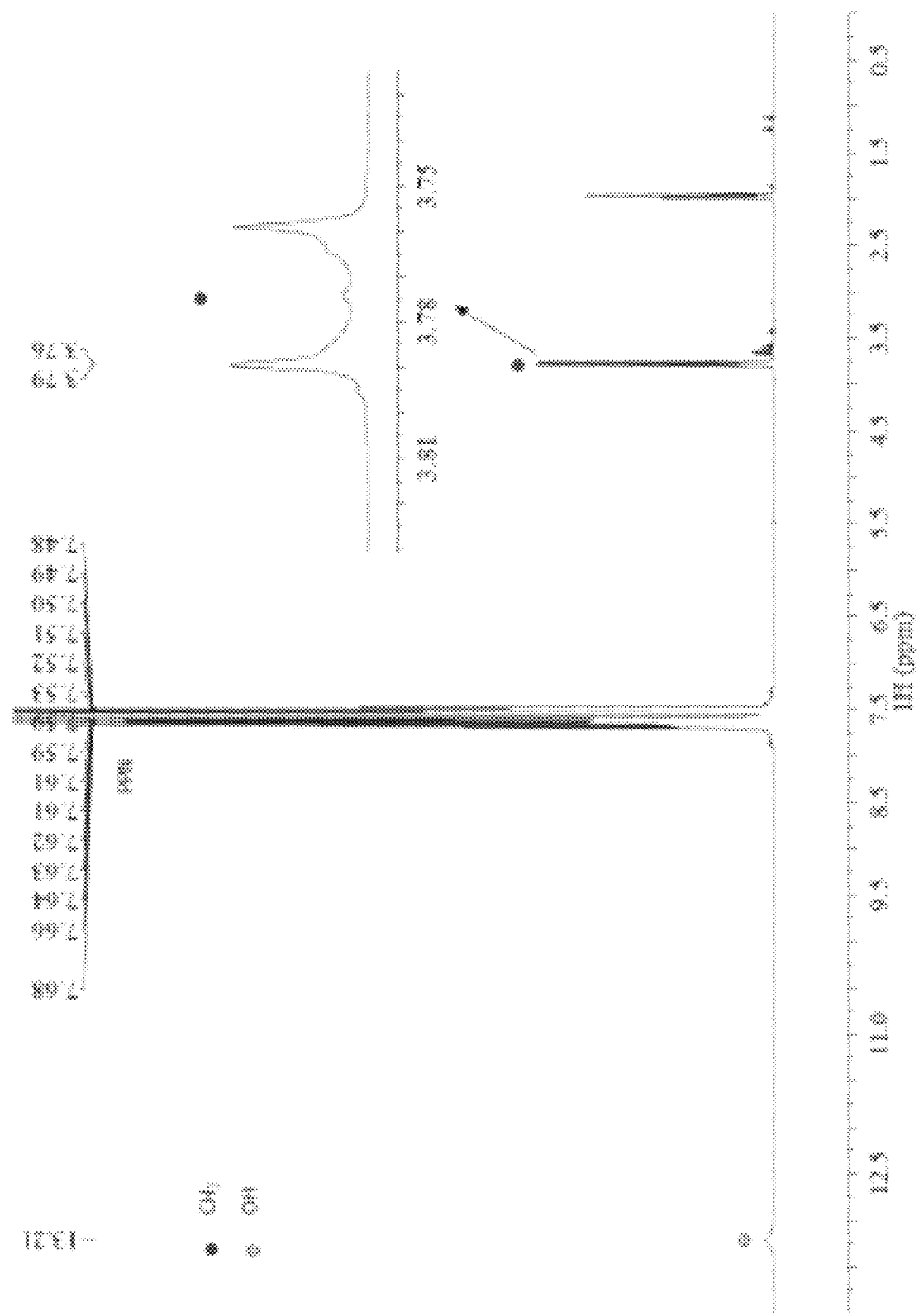
FIG. 17 shows 1H NMR (400.1 MHz) spectrum of the PPN salt of $[(P_4O_{10})(OH)(OMe)]^{2-}$ (3) recorded at 23° C. in $CD_3CN$.
Figure 18:
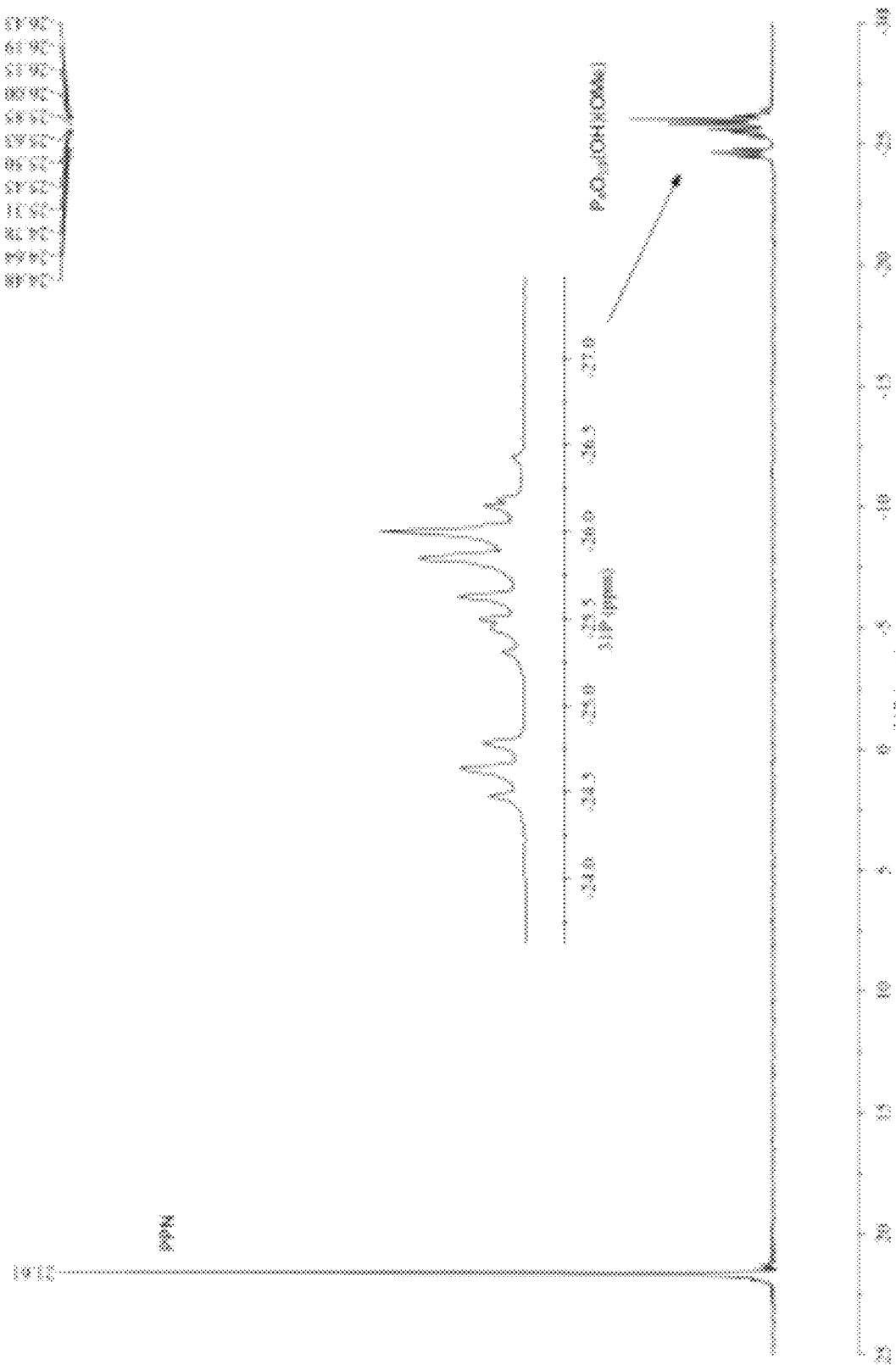
FIG. 18 shows $^{31}P\{^1H\}$ NMR (161.9 MHz) spectrum of the PPN salt of $[(P_4O_{10})(OH)(OMe)]^{2-}$ (3) recorded at 23° C. in $CD_3CN$.
Figure 19:
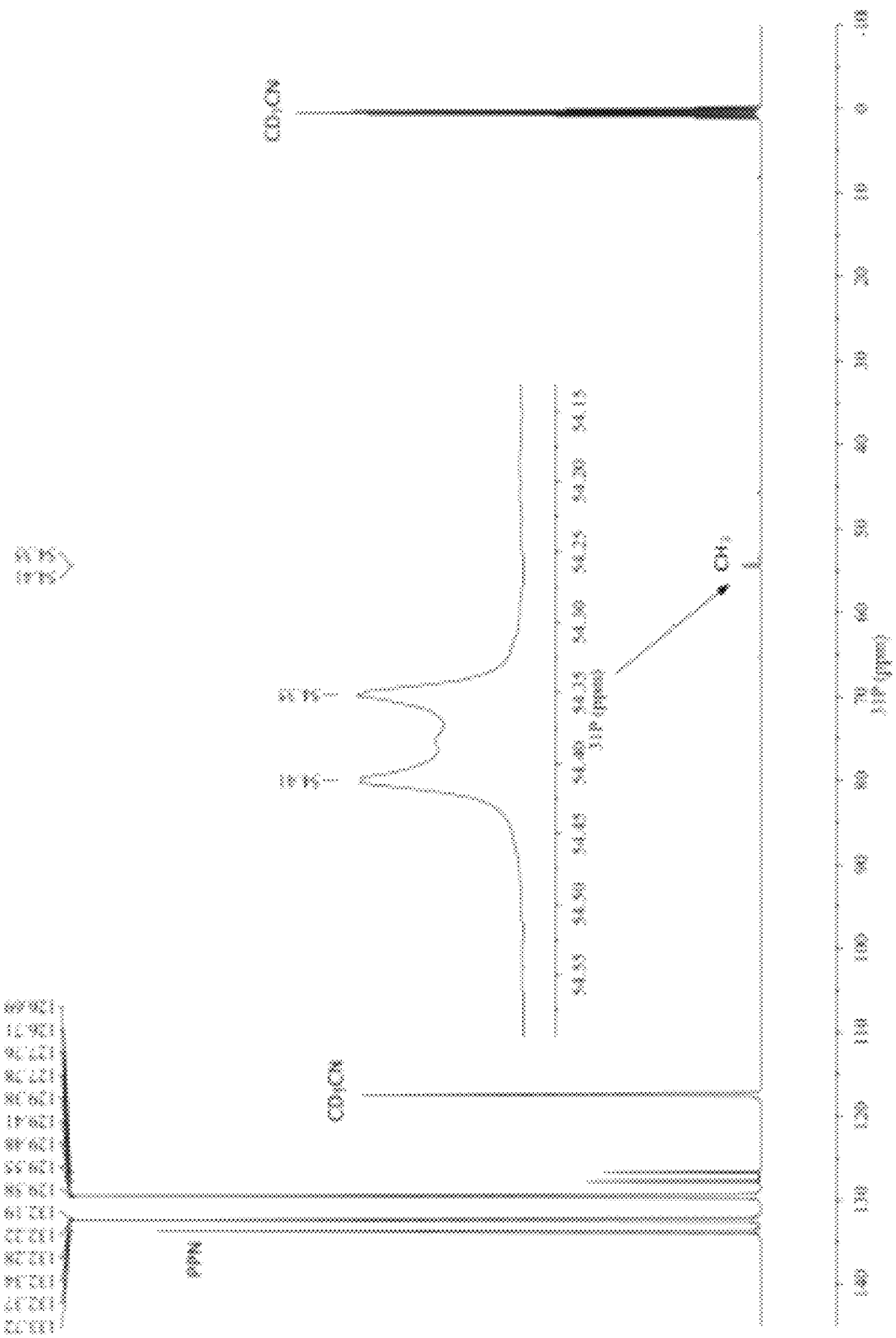
FIG. 19 shows $^{13}C$ NMR (100 MHz) spectrum of the PPN salt of $[(P_4O_{10})(OH)(OMe)]^{2-}$ (3) recorded at 23° C. in $CD_3CN$.
Figure 20:
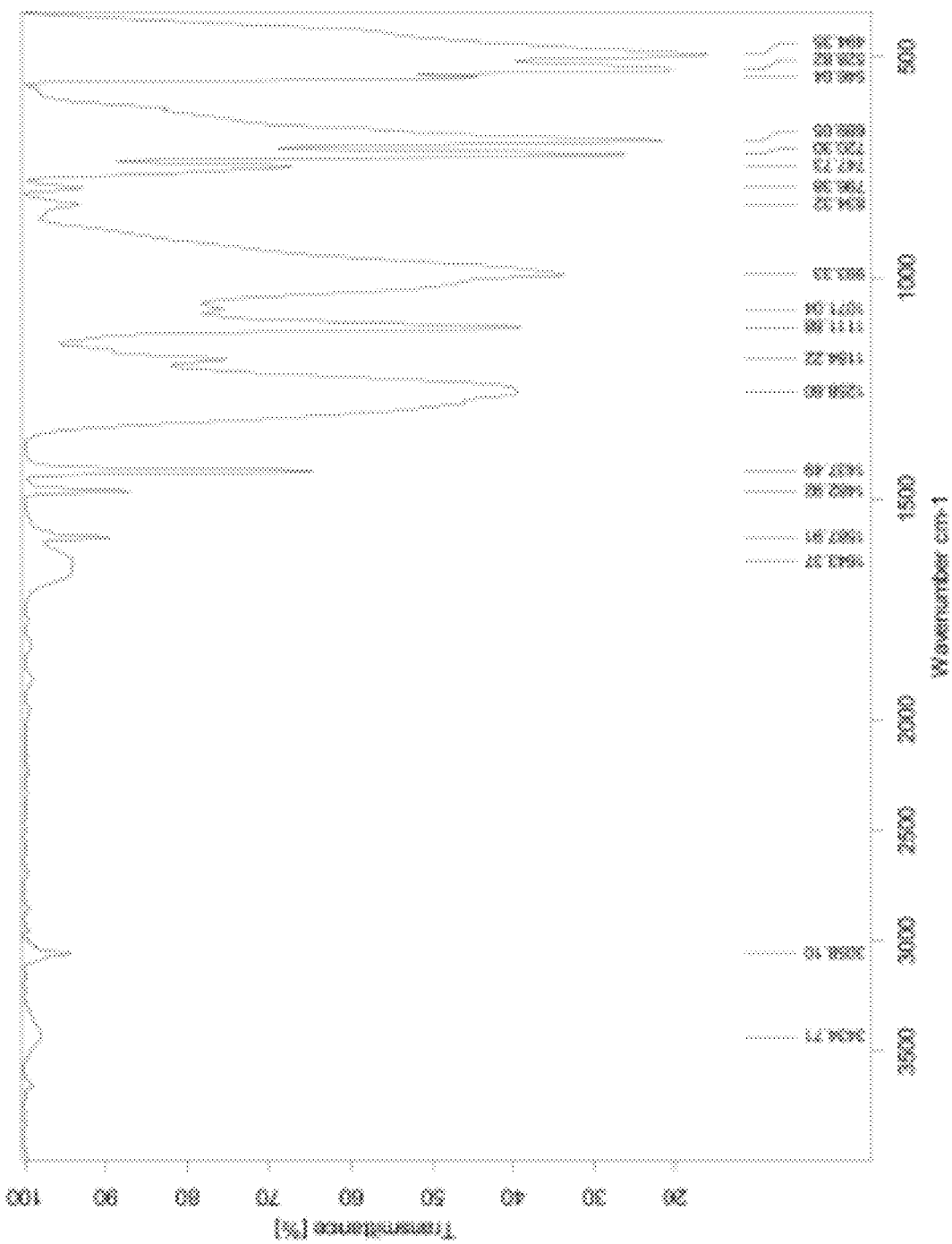
FIG. 20 shows ATR-IR spectrum of solid $[PPN]_2[(P_4O_{10})(OH)(OMe)]$ ($[PPN]_2[3]$).
Figure 21:
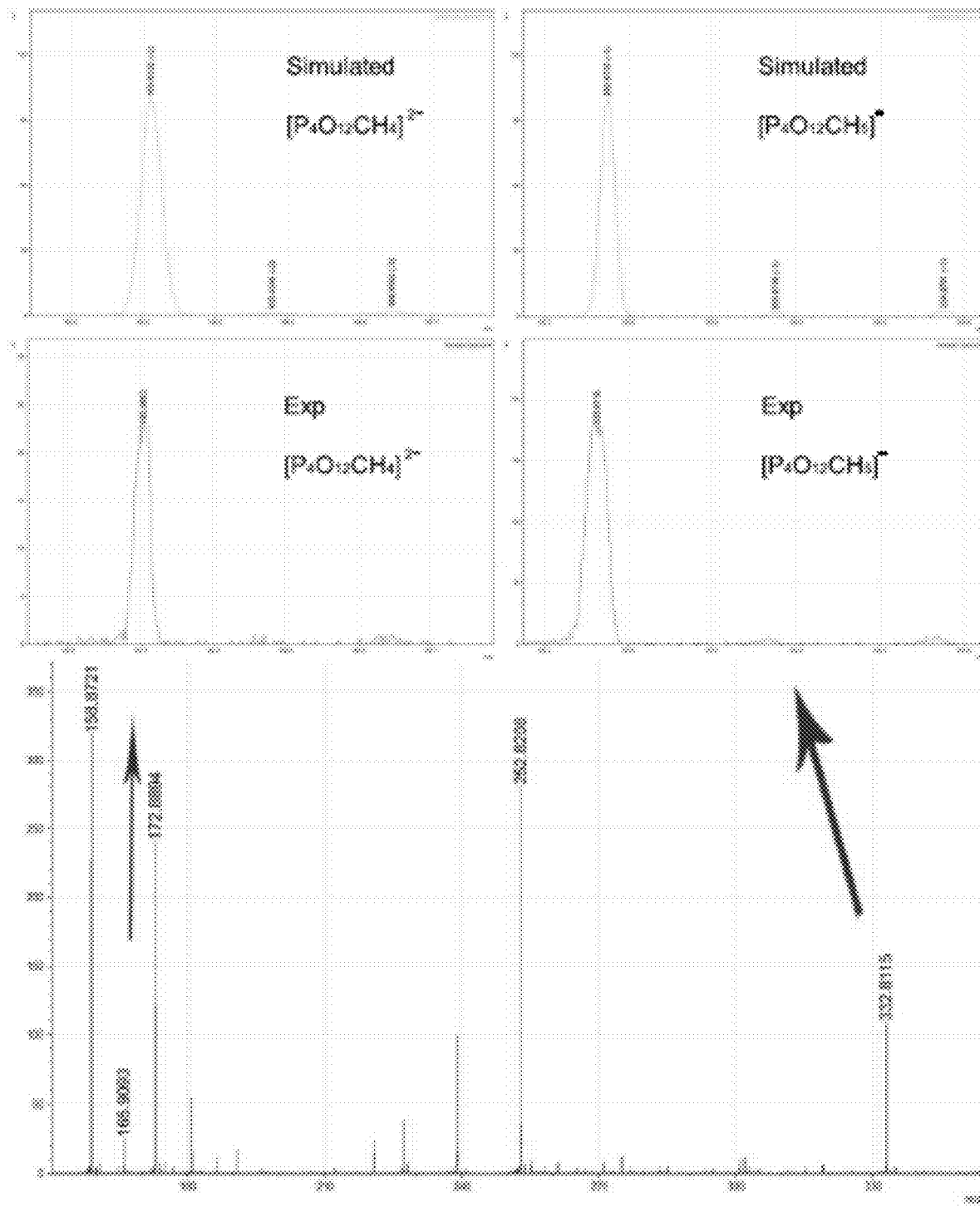
FIG. 21 shows ESI-MS(−) spectrum of the PPN salt of $[(P_4O_{10})(OH)(OMe)]^{2-}$ (3).
Figure 22:
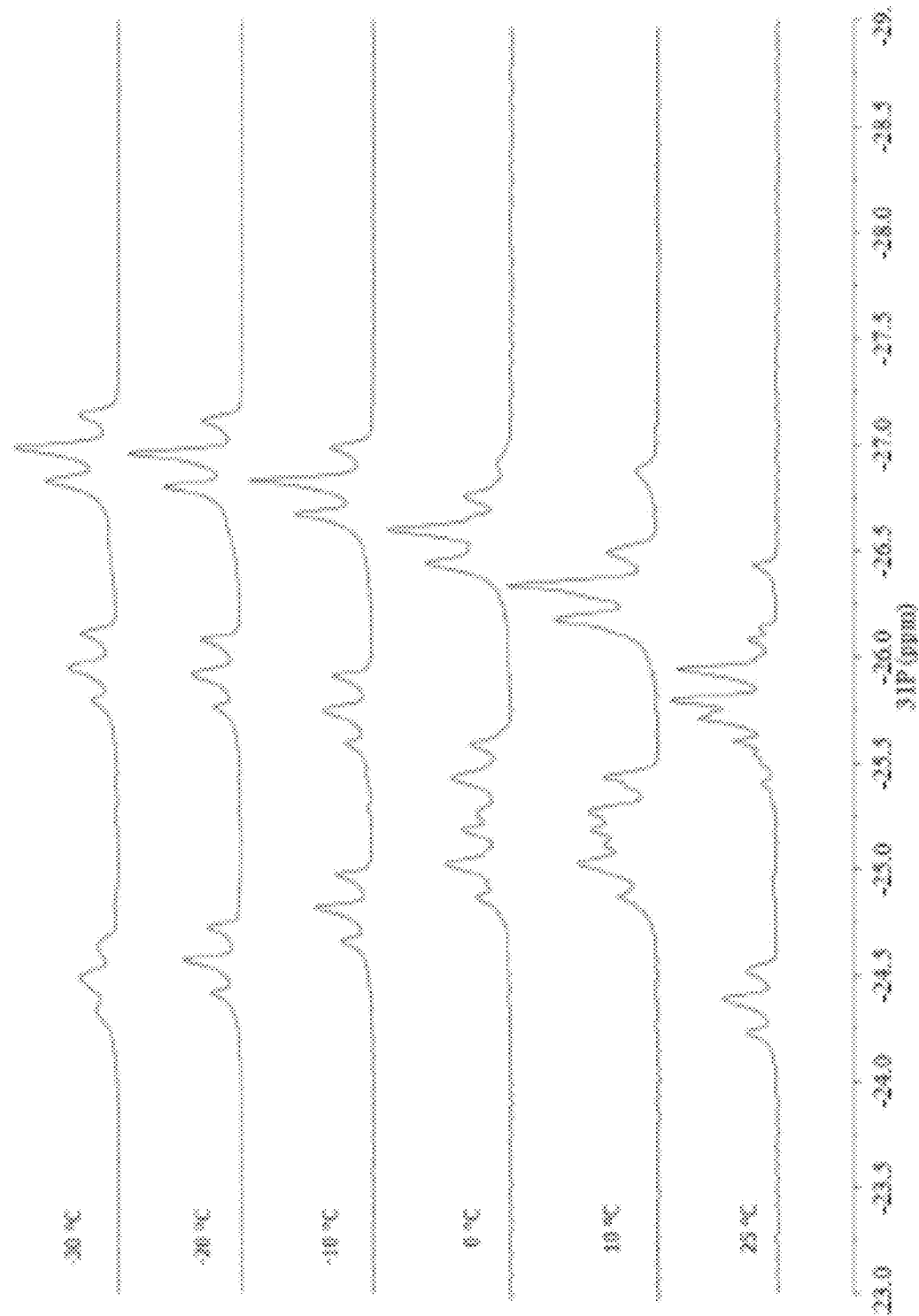
FIG. 22 shows VT-$^{31}P\{^1H\}$ NMR spectra of the PPN salt of $[(P_4O_{10})(OH)(OMe)]^{2-}$ (3) recorded from 25 to −30° C. in $CH_3CN$.
Figure 23:
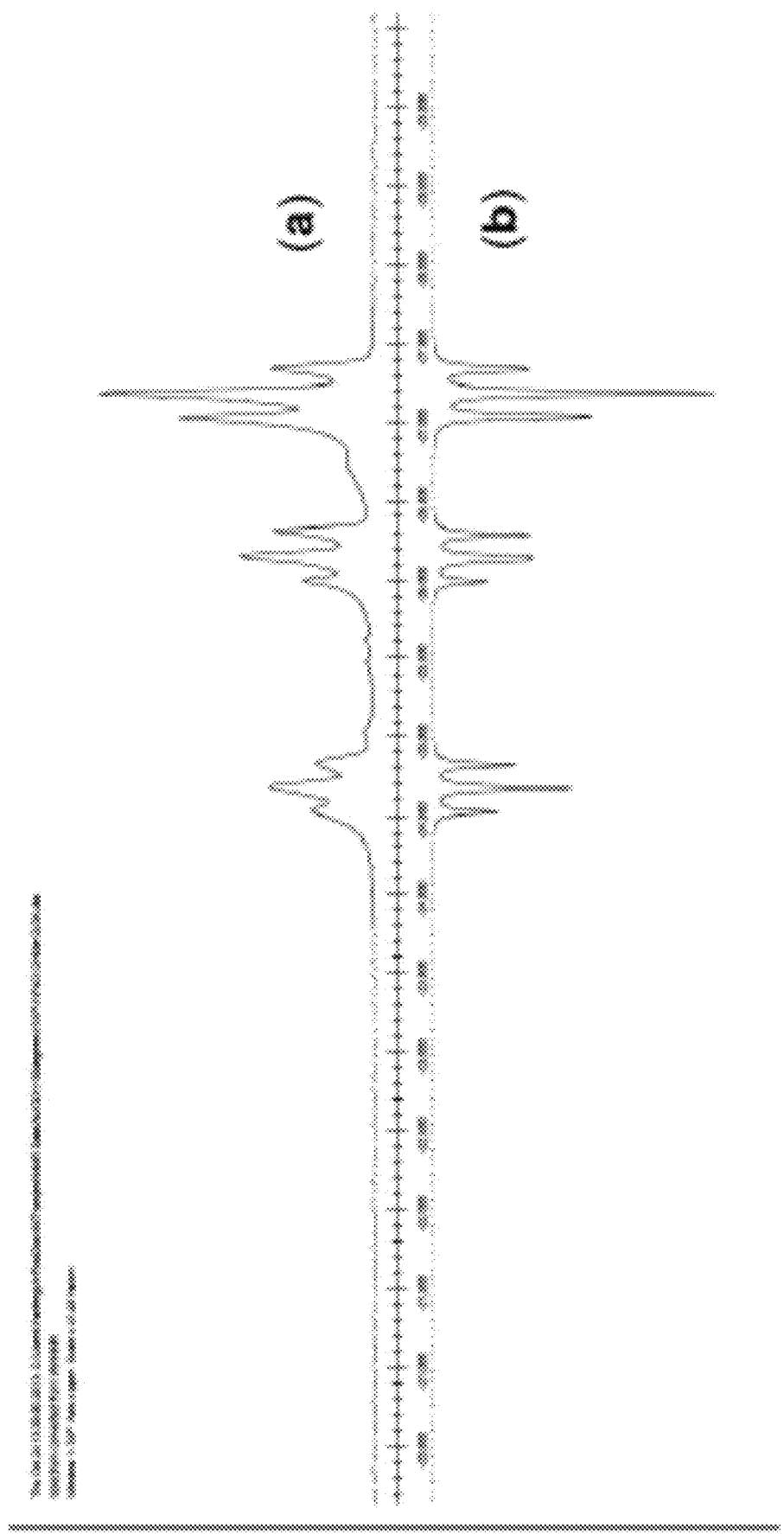
FIG. 23 shows $^{31}P\{^1H\}$ NMR spectra of (a): $[PPN]_2[(P_4O_{10})(OH)(OMe)]$ ($[PPN]_2[3]$) recorded at −30° C. in $CH_3CN$ and (b): Simulated spectrum using gNMR (gNMR V5, Adept Scientific pic, Amor Way, Letchworth Herts, SG6 1ZA, UK, 2003).

FIG. 17 shows $^1$H NMR (400.1 MHz) spectrum of [PPN]$_2$[(P$_4$O$_{10}$)(OH)(OMe)] ([PPN]$_2$[3]) recorded at 23° C. in CD$_3$CN. FIG. 18 shows $^{31}$P{$^1$H} NMR (161.9 MHz) spectrum of [PPN]$_2$[(P$_4$O$_{10}$)(OH)(OMe)] ([PPN]$_2$[3]) recorded at 23° C. in CD$_3$CN. FIG. 19 shows $^{13}$C NMR (100 MHz) spectrum of [PPN]$_2$[(P$_4$O$_{10}$)(OH)(OMe)] ([PPN]$_2$[3]) recorded at 23° C. in CD$_3$CN. FIG. 20 shows ATR-IR spectrum of solid [PPN]$_2$[(P$_4$O$_{10}$)(OH)(OMe)] ([PPN]$_2$[3]). FIG. 21 shows ESI-MS(−) spectrum of [PPN]$_2$[(P$_4$O$_{10}$)(OH)(OMe)] ([PPN]$_2$[3]). FIG. 22 shows VT-$^{31}$P{$^1$H} NMR spectra of [PPN]$_2$[(P$_4$O$_{10}$)(OH)(OMe)] ([PPN]$_2$[3]) recorded from 25 to −30° C. in CH$_3$CN. FIG. 23 shows $^{31}$P{$^1$H} NMR spectra of (a): [PPN]$_2$[(P$_4$O$_{10}$)(OH)(OMe)] ([PPN]$_2$[3]) recorded at −30° C. in CH$_3$CN and (b): Simulated spectrum using gNMR (gNMR V5, Adept Scientific pic, Amor Way, Letchworth Herts, SG6 1ZA, UK, 2003).

Preparation of Monomeric Tin(II) κ$^4$ Tetrametaphosphate (as its PPN Salt) [PPN]$_2$[Sn(P$_4$O$_{12}$)] ([PPN]$_2$[4])

Path: [PPN]$_2$[P$_4$O$_{12}$H$_2$] with Sn(HMDS)$_2$

In a glove box, Sn(HMDS)$_2$ (18.8 mg, 0.043 mmol, 1.0 equiv.) was dissolved in acetonitrile (0.5 mL) and to the resulting solution was added dropwise [PPN]$_2$[P$_4$O$_{12}$H$_2$] (61.7 mg, 0.044 mmol, 1.02 equiv.) as a solution in acetonitrile (2 mL) at room temperature over 30 s. Upon complete addition of the [PPN]$_2$[P$_4$O$_{12}$H$_2$] solution the color of the reaction mixture changed from orange to colorless. The reaction mixture was allowed to stir at room temperature for 15 minutes. Afterwards the mixture was filtered through a glass microfiber filter and all volatile materials were removed in vacuo affording a colorless residue, which was washed with diethyl ether (2×2 mL) and pentane (2×2 mL), and dried in vacuo to afford [PPN]$_2$[4] as an analytically pure white solid (Yield: 51 mg, 0.034 mmol, 78%).

Characterization of [PPN]$_2$[Sn(P$_4$O$_{12}$)] ([PPN]$_2$[4])

ESI-MS(−)(CH$_3$CN, m/z): 436.8545 ([SnP$_4$O$_{12}$H]$^-$), 217.9028 ([SnP$_4$O$_{12}$]$^{2-}$). IR (ATR, cm$^{-1}$): ν 1282 (s, P=O), 996 (s, P—O). 1H NMR (CD$_3$CN, 400.1 MHz, ppm) δ: 7.48-7.71 (m, 72H, [PPN]$^+$). $^{31}$P{H} NMR (CD$_3$CN, 161.9 MHz, ppm) δ: 22.10 (s, 4P, PPN), −23.54 (s, 4P). $^{13}$C NMR (CD$_3$CN, 100 MHz, ppm): 133.67 (s), 132.28 (m), 129.45 (m), 127.76 (s), 126.69 (s). $^{119}$Sn NMR (CD$_3$CN, 149 MHz, ppm) δ: −800.57 (s, 1 Sn). Anal. Calcd for C$_{72}$H$_{60}$N$_2$O$_{12}$P$_8$Sn (1511.7741): C, 57.20; H, 4.00; N, 1.85%. Found: C, 57.41; H, 3.90; N, 1.86%.

Figure 24:
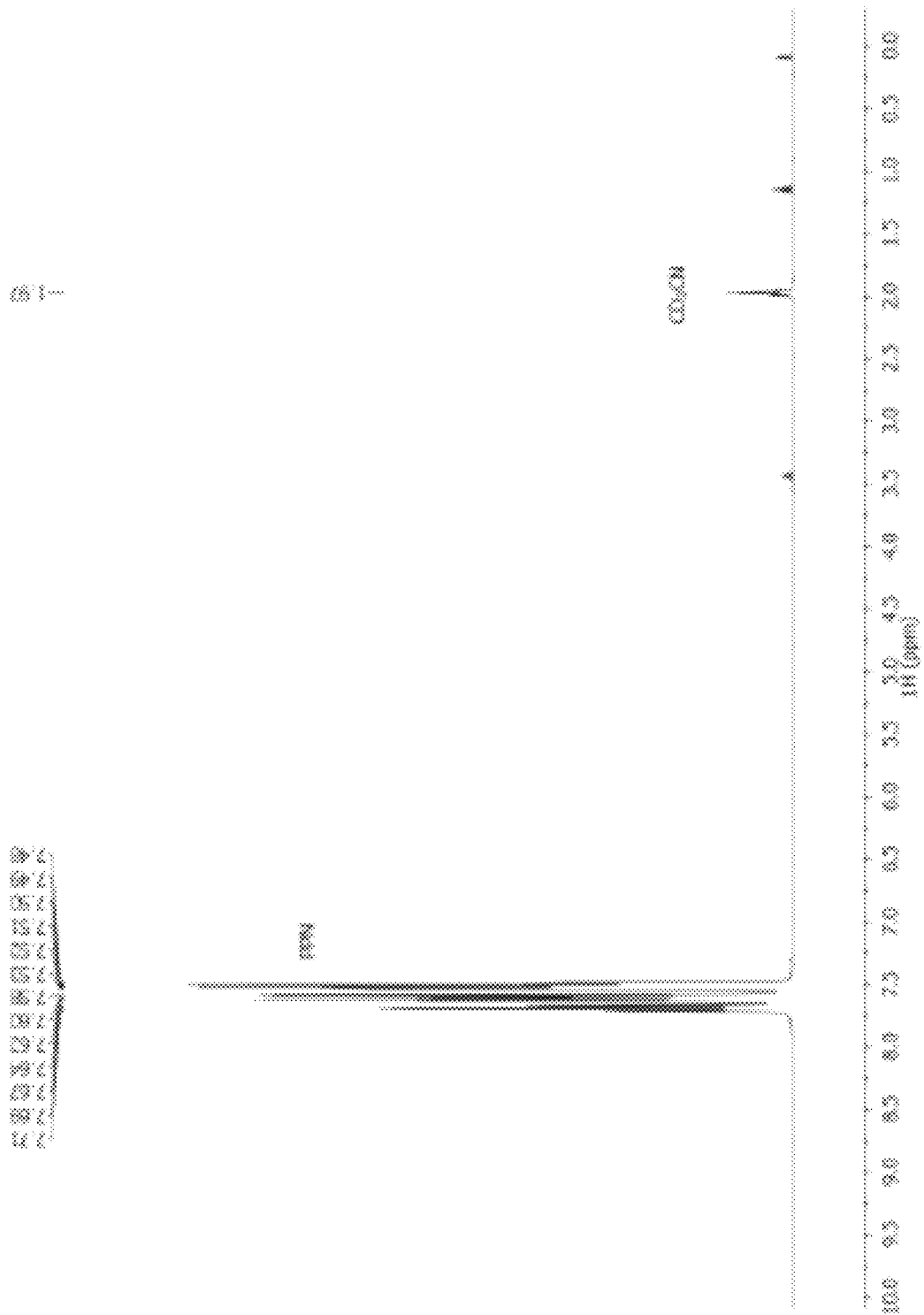
FIG. 24 shows $^1H$ NMR (400.1 MHz) spectrum of the PPN salt of $[Sn(P_4O_{12})]^{2-}$ (4) recorded at 23° C. in $CD_3CN$.
Figure 25:
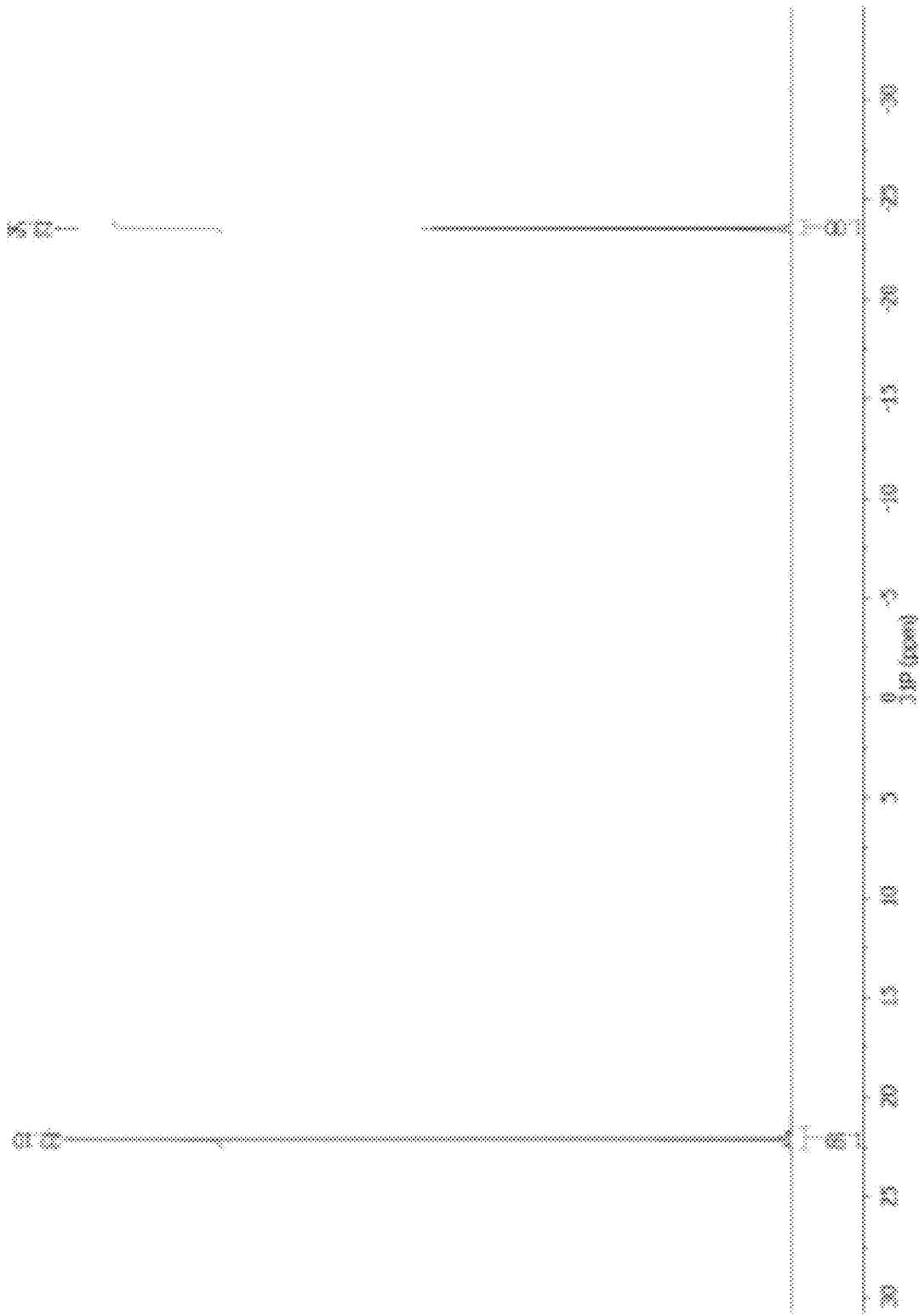
FIG. 25 shows $^{31}P\{^1H\}$ NMR (161.9 MHz) spectrum of the PPN salt of $[Sn(P_4O_{12})]^{2-}$ (4) recorded at 23° C. in $CD_3CN$.
Figure 26:
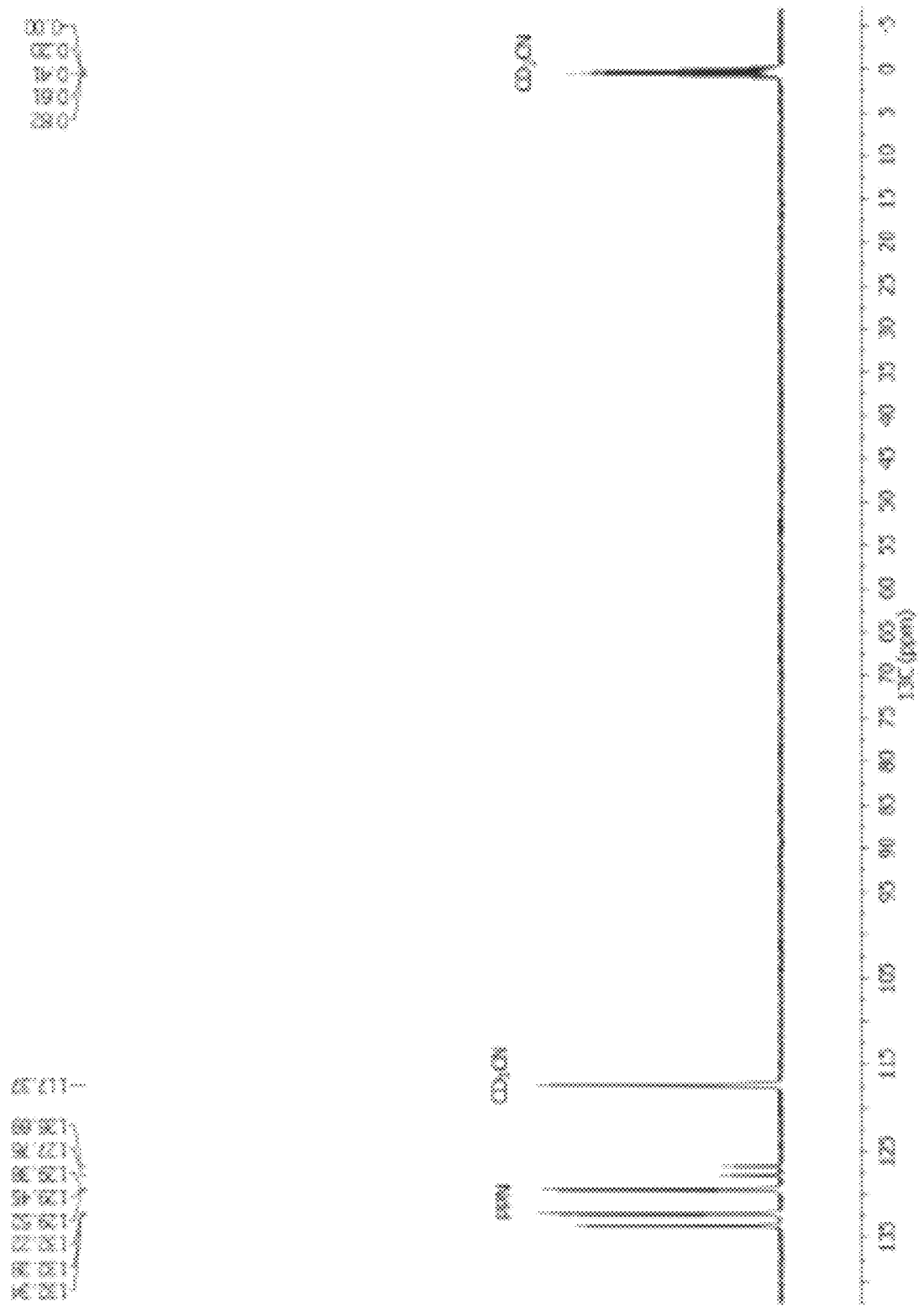
FIG. 26 shows 13C NMR (100 MHz) spectrum of the PPN salt of $[Sn(P_4O_{12})]^{2-}$ (4) recorded at 23° C. in $CD_3CN$.
Figure 27:
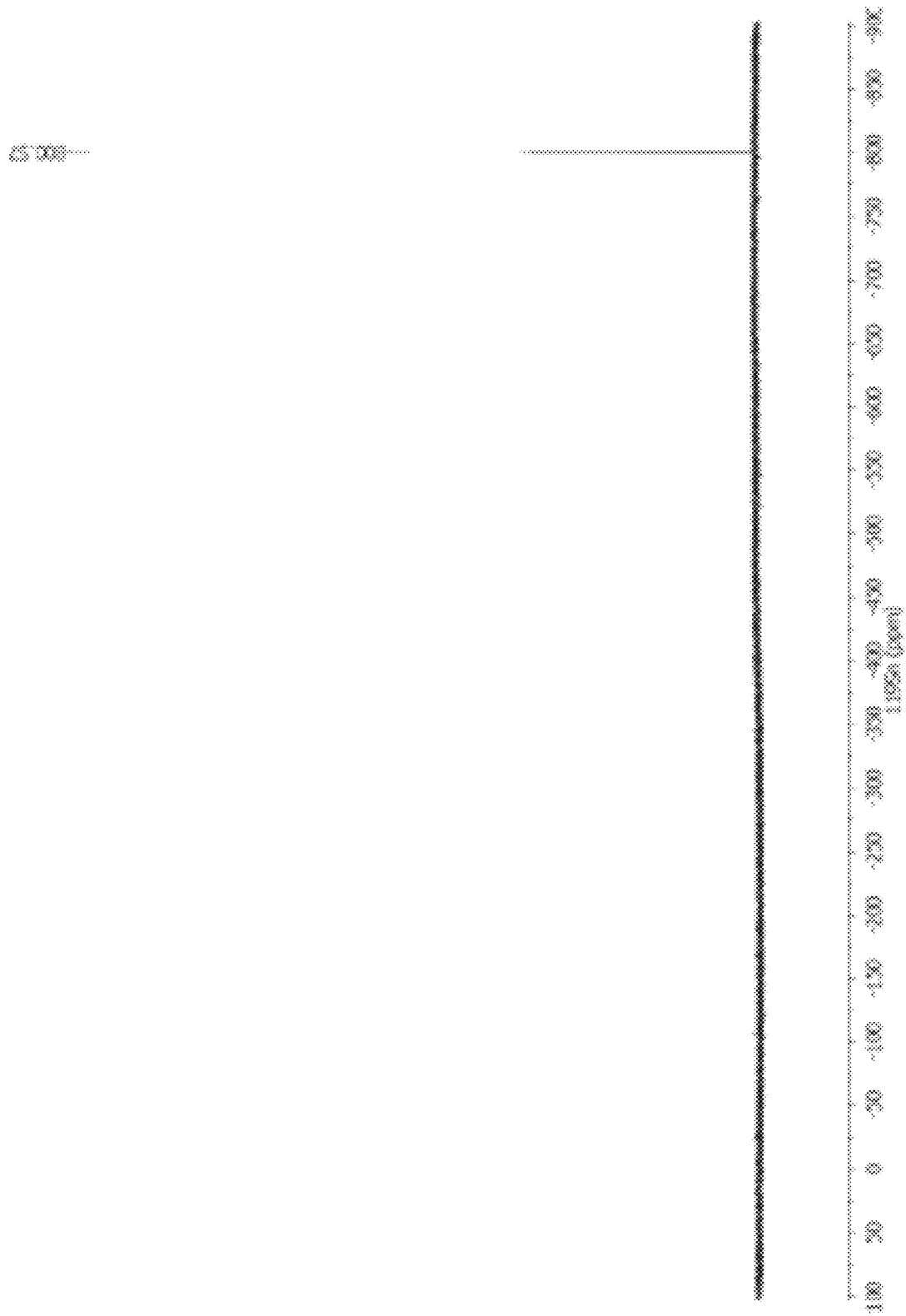
FIG. 27 shows $^{119}Sn$ NMR (149 MHz) spectrum of the PPN salt of $[Sn(P_4O_{12})]^{2-}$ (4) recorded at 23° C. in $CD_3CN$.
Figure 28:
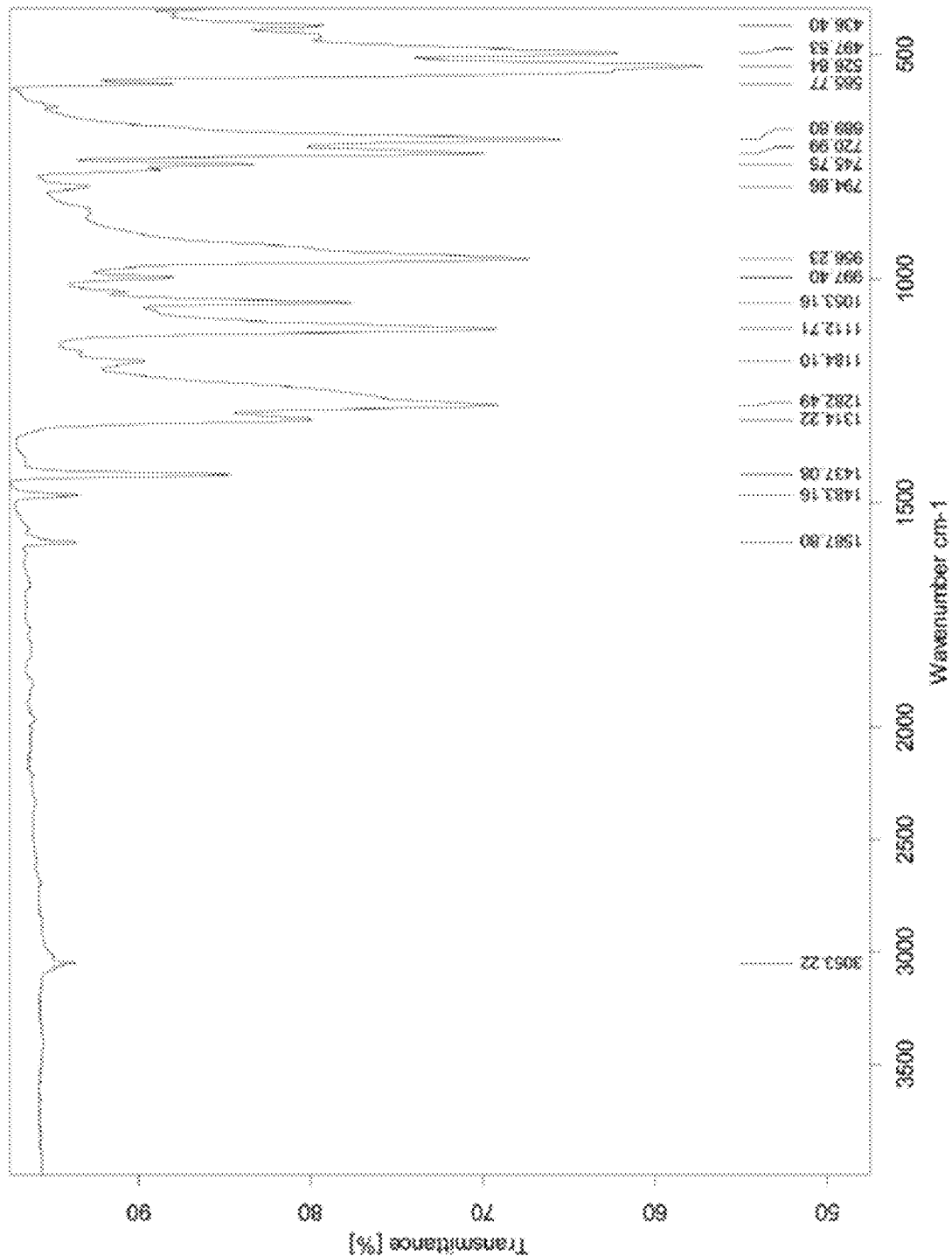
FIG. 28 shows ATR-IR spectrum of solid $[PPN]_2[Sn(P_4O_{12})]$ ($[PPN]_2[4]$).
Figure 29:
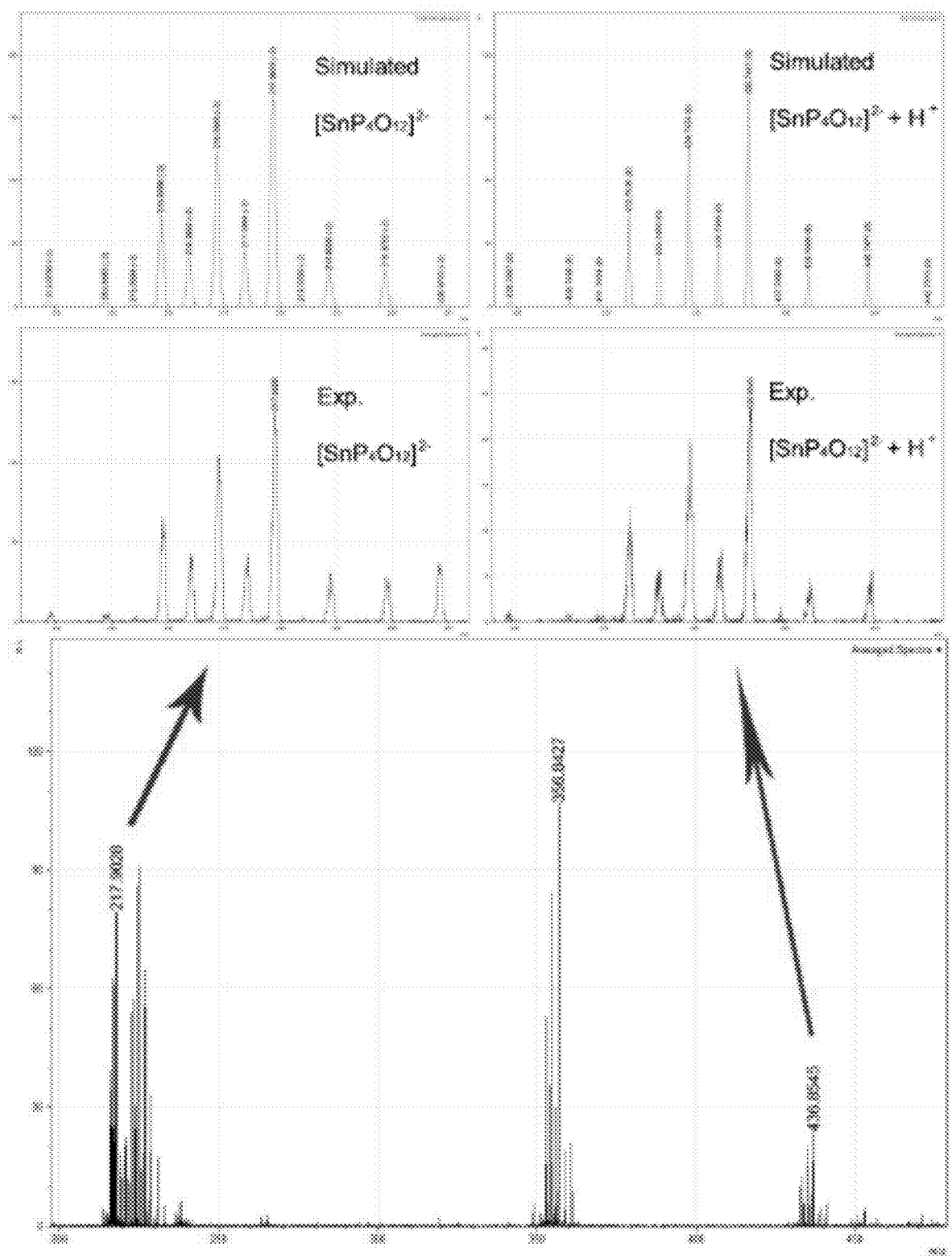
FIG. 29 shows ESI-MS(−) spectrum of the PPN salt of $[Sn(P_4O_{12})]^{2-}$ (4).

FIG. 24 shows $^1$H NMR (400.1 MHz) spectrum of [PPN]$_2$[Sn(P$_4$O$_{12}$)] ([PPN]$_2$[4]) recorded at 23° C. in CD$_3$CN. FIG. 25 shows $^{31}$P{$^1$H} NMR (161.9 MHz) spectrum of [PPN]$_2$[Sn(P$_4$O$_{12}$)] ([PPN]$_2$[4]) recorded at 23° C. in CD$_3$CN. FIG. 26 shows $^{13}$C NMR (100 MHz) spectrum of [PPN]$_2$[Sn(P$_4$O$_{12}$)] ([PPN]$_2$[4]) recorded at 23° C. in CD$_3$CN. FIG. 27 shows $^{119}$Sn NMR (149 MHz) spectrum of [PPN]$_2$[Sn(P$_4$O$_{12}$)] ([PPN]$_2$[4]) recorded at 23° C. in CD$_3$CN. FIG. 28 shows ATR-IR spectrum of solid [PPN]$_2$[Sn(P$_4$O$_{12}$)]([PPN]$_2$[4]). FIG. 29 shows ESI-MS(−) spectrum of [PPN]$_2$[Sn(P$_4$O$_{12}$)] ([PPN]$_2$[4]).

Preparation of Binary Dimeric Chromium(II) κ$^2$ Tetrametaphosphate (as its PPN salt) [PPN]$_4$[Cr$_2$(P$_4$O$_{12}$)$_2$] ([PPN]$_4$[5])

Path: [PPN]$_2$[P$_4$O$_{12}$H$_2$] with Cr(HMDS)$_2$(THF)$_2$

In a glove box, Cr(HMDS)$_2$(THF)$_2$ (25.5 mg, 0.05 mmol, 1.0 equiv.) was mixed with acetonitrile (5 mL), to which mixture was then added dropwise [PPN]$_2$[P$_4$O$_{12}$H$_2$](70.9 mg, 0.05 mmol, 1.0 equiv.) as a solution in acetonitrile (5 mL) at room temperature. Immediately the color of the solution changed from brown-purple to pale green. After stirring at room temperature for 30 min, the solution was filtered through a glass microfiber filter. Solvent was removed from the filtrate in vacuo to afford a pale green residue. Addition of diethyl ether (2 mL) to the latter residue afforded a pale green solution with grey solids. The pale green solution was decanted away, and the solid was further washed with pentane (2×1 mL), and freed of solvent residues in vacuo to afford [PPN]$_4$[5] as a pale grey powder (Yield: 59 mg, 0.019 mmol, 82%).

Characterization of [PPN]$_4$[Cr$_2$(P$_4$O$_{12}$)$_2$] ([PPN]$_4$[5])

ESI-MS(−) (CH$_3$CN, m/z): 367.7146 ([Cr(III)$_2$(P$_4$O$_{12}$)$_2$]$^{2-}$). IR (ATR, cm$^{-1}$): ν 1268 (P=O), 977 (P—O). Anal. Calcd for 4(C$_{36}$H$_{30}$NP$_2$), Cr$_2$O$_{24}$P$_8$, 0.70(C$_4$H$_{10}$O), 3.3(C$_2$H$_3$N) (3077.45): C, 59.87; H, 4.48; N, 3.32%. Found: C, 60.21; H, 4.72; N, 3.19%.

Figure 30:
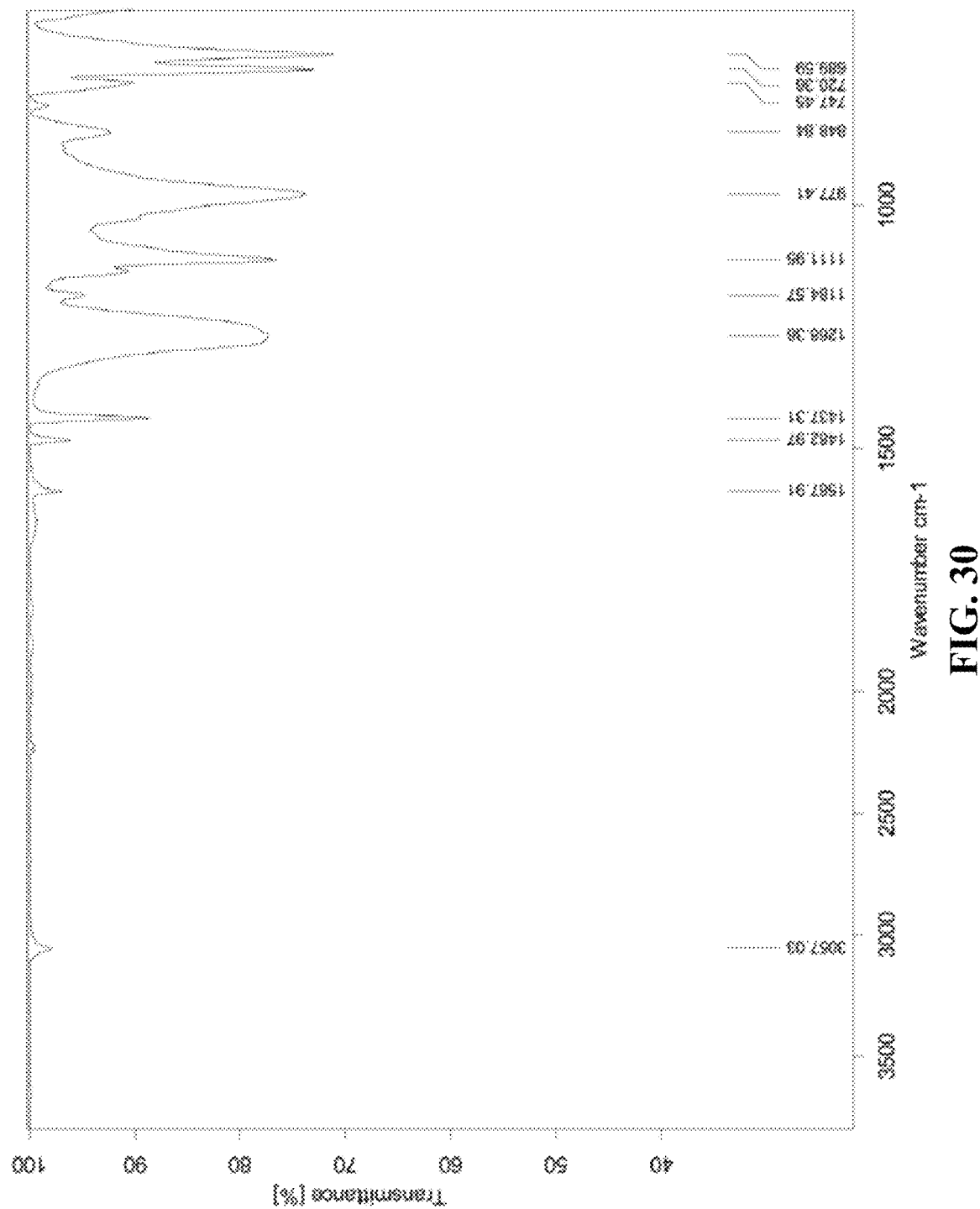
FIG. 30 shows ATR-IR spectrum of solid $[PPN]_4[Cr_2(P_4O_{12})_2]$ ($[PPN]_4[5]$).
Figure 31:
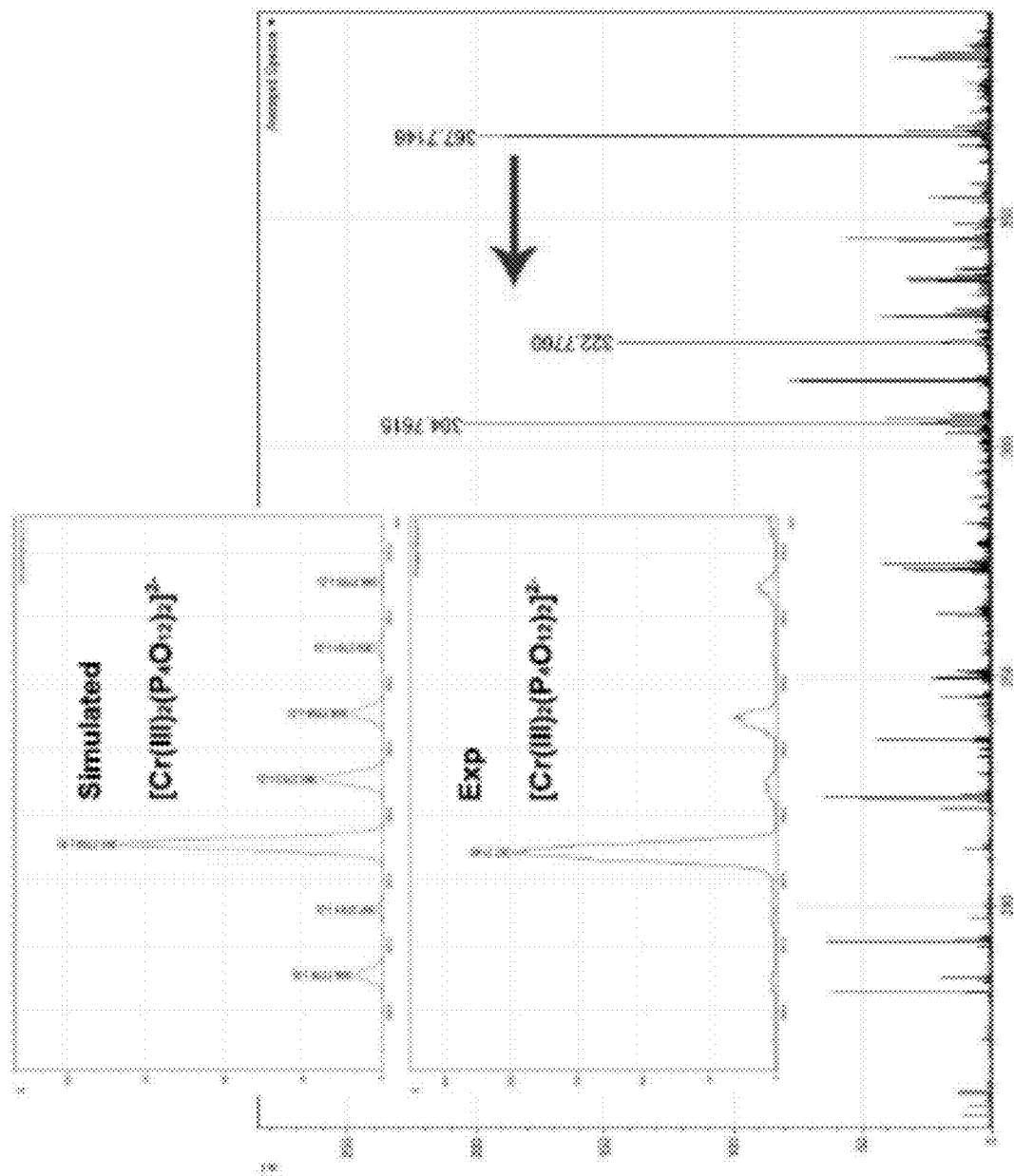
FIG. 31 shows ESI-MS(−) spectrum of $[PPN]_4[Cr_2(P_4O_{12})_2]$ ($[PPN]_4[5]$). $[Cr_2(P_4O_{12})_2]^{4-}$ cannot be directly observed by ESI-MS spectroscopy due to its tetraanion character. However, its oxidized form $[Cr(III)_2(P_4O_{12})_2]^{2-}$, which was generated under ESI-MS conditions, was indeed observed by ESI-MS spectroscopy confirming the presence of $[Cr_2(P_4O_{12})_2]^{4-}$.

FIG. 30 shows ATR-IR spectrum of solid [PPN]$_4$[Cr$_2$(P$_4$O$_{12}$)$_2$] ([PPN]$_4$[5]). FIG. 31 shows ESI-MS(−) spectrum of [PPN]$_4$[Cr$_2$(P$_4$O$_{12}$)$_2$] ([PPN]$_4$[5]). [Cr$_2$(P$_4$O$_{12}$)$_2$]$^{4-}$ cannot be directly observed by ESI-MS spectroscopy due to its tetraanion character. However, its oxidized form [Cr(III)$_2$(P$_4$O$_{12}$)$_2$]$^{2-}$, which was generated under ESI-MS conditions, was indeed observed by ESI-MS spectroscopy confirming the presence of [Cr$_2$(P$_4$O$_{12}$)$_2$]$^{4-}$.

pK$_a$ Determination of [PPN]$_2$[P$_4$O$_{12}$H$_2$] in Acetonitrile

The acid dissociation of [PPN]$_2$[P$_4$O$_{12}$H$_2$] is one of the four steps in the ionization of tetrametaphosphoric acid H$_4$P$_4$O$_{12}$ (Eqn. 1). Herein, pK$_{a3}$ value which corresponds to the acidity of [PPN]$_2$[P4O$_{12}$H$_2$] (Eqn. 1c) was determined.

$$H_4P_4O_{12} \rightarrow [P_4O_{12}H_3]^- + H^+ \tag{1a}$$

$$[P_4O_{12}H_3]^- \rightarrow [P_4O_{12}H_2]^{2-} + H^+ \tag{1b}$$

$$[P_4O_{12}H_2]^{2-} \rightarrow [P_4O_{12}H]^{3-} + H^+ \tag{1c}$$

$$[P_4O_{12}H]^{3-} \rightarrow [P_4O_{12}]^{4-} + H^+ \tag{1d}$$

Spectrophotometric titration was employed to determine the pK$_a$ of [PPN]$_2$[P$_4$O$_{12}$H$_2$] in acetonitrile, following an established procedure. See, for example, Yagupolskii, L. M.; Petrik, V. N.; Kondratenko, N. V.; Soovali, L.; Kaljurand, I.; Leito, I.; Koppel, I. A. J. Chem. Soc., Perkin Trans. 2002, 2, 1950-1955, which is incorporated by reference in its entirety. Inside a glove box equipped with an atmosphere of purified nitrogen, acetonitrile from a Glass Contour Solvents Purification System was stored over 4 Å molecular sieves for 3 days and filtered through a PTFE syringe filter with a 0.22 μm pore size purchased from Santa Cruz Biotechnology prior to all titrations. A solution of NEt$_3$ (1.83×10$^{-3}$ M) was used as a basic titrant and was prepared by diluting 2.53 μL NEt$_3$ with acetonitrile to 10.00 mL. UV-Visible absorption spectra were recorded using a HP 845x UV-Visible spectrophotometer.

The acidity measurement was sensitive to ambient moisture and hence had to be performed under anhydrous condition. Sample preparation was conducted inside a glove box equipped with an atmosphere of purified nitrogen. In a quartz cuvette capped with a PTFE septum, a UV-Vis absorption spectrum of 2,4-dinitrophenol (3.00 mL, 6.08× $10^{-5}$M) was recorded prior to the titration. The sample was then mixed with [PPN]$_2$[P$_4$O$_{12}$H$_2$](199 μL, 9.175×$10^{-4}$ M), resulting in a color change of the mixture from yellow to colorless which corresponded to the reaction between [PPN]$_2$[P$_4$O$_{12}$H$_2$] and 2,4-dinitrophenolate anion present in the 2,4-dinitrophenol (Eqn. 2).

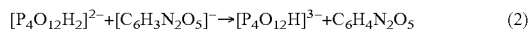  (2)

Triethylamine titrant (5-10 μL, 1.83×$10^{-3}$ M) was introduced into a cuvette by the use of microsyringe and septum. A UV-Vis absorption spectrum was taken immediately following each addition. The titration was discontinued when no changes were observed in the UV-Vis absorption spectra upon further addition of titrant. After the titration was complete, portions of triflic acid (10-20 μL, 1.01×$10^{-2}$ M) were added to confirm the reversibility of the reaction until all 2,4-dinitrophenolate absorption peaks disappeared, signifying the point at which 2,4-dinitrophenol existed only in acid form. No distortion of the isobestic point was observed, thus homoconjugation and heteroconjugation were assumed negligible within the system.

The concentration of [P4O$_{12}$H$_2$]$^{2-}$ ([HA1]), 2,4-dinitrophenol ([HA$_2$]), [P$_4$O$_{12}$H]$^{3-}$ ([A$_1^-$]), and 2,4-dinitrophenolate ([A$_2^-$]) were calculated using the initial absorbance of 2,4-dinitrophenol (A$_{DNP}{}^\lambda$), the absorbances over the course of the titration (A$^\lambda$), and the absorbance at which 2,4-dinitrophenol existed only in acid form after addition of triflic acid (A$_0{}^\lambda$). The total molar concentrations of [PPN]$_2$[P$_4$O$_{12}$H$_2$] (C$_1$), 2,4-dinitrophenol (C$_2$), and triethylamine titrant (C$_{NEt3}$) were obtained from moles of corresponding reagents added to the analyte, and were used in the calculation (Eqn. 3).

The molar absorptivity of 2,4-dinitrophenolate ($\varepsilon^\lambda$) was obtained by a separate titration of 2,4-dinitrophenol with NEt3 titrant. Two maximum absorption peaks at 372 and 426 nm were chosen for the calculation. At these wavelengths, the absorption of 2,4-dinitrophenol was practically negligible. There was no absorption from [PPN]$_2$[P$_4$O$_{12}$H$_2$] in the region 350 to 500 nm of interest of the UV-Vis spectrum.

Generally, only the first 6-7 spectra over the course of the titration were useful because the indicator ratio of 2,4-dinitrophenol was in the range where high accuracy could be obtained, and the second acid dissociation by [P$_4$O$_{12}$H]$^{3-}$ started to interfere with the determination thereafter (Eqn. 1d). The relative acidity could be calculated from equation 4.

$$HA_1 + A_2^- \rightleftharpoons A_1^- + HA_2 \quad (4)$$

$$\Delta pK_a = pK_a(HA_2) - pK_a(HA_1) = \log\frac{[A_1^-][HA_2]}{[A_2^-][HA_1]}$$

The acidity determination using 12 data points from two absorption peaks over the course of the titration resulted in pK$_{a3}$ value of 15.83, with a standard deviation of 0.11. The relative acidity was referenced to 2,4-dinitrophenol of which pK$_a$ is 16.66 in acetonitrile. See, for example, Leito, I.; Kaljurand, I.; Koppel, I. A.; Yagupolskii, L. M.; Vlasov, V. M. *J. Org. Chem.* 1998, 63, 7868-7874, which is incorporated by reference in its entirety.

X-ray Data Collection and Structure Determinations

Single crystal X-ray diffraction data for the PPN salts of 1-5 (ø- and ω-scans) were collected at 100 K either on a Bruker-AXS X8 Kappa Duo diffractometer coupled to a Smart Apex2 CCD detector (the PPN salts of 1, 3-5) or on a Siemens Platform three-circle diffractometer coupled to a Bruker-AXS Smart Apex CCD detector (the PPN salt of 2), using graphite-monochromated Mo-Kα radiation (λ=0.71073 Å) in either case, and processed through the SAINT reduction and SADABS absorption software. The structures were solved by direct methods using SHELXS and refined against F$^2$ on all data by full-matrix least squares with SHELXL-2013, using established methods. See, for example, SAINT, Version 6.45, Bruker Analytical X-ray Systems Inc., Madison, Wis., USA, 2003; SADABS, Version 2.03, Bruker AXS Inc., Madison, Wis., USA, 2000; Sheldrick, G. M. Acta Cryst. 1990, 46, 467-473; Sheldrick, G. M. Acta Cryst. 2008, 64, 112-122; Mueller, P.; Herbst-Irmer, R.; Spek, A. L.; Schneider, T. R.; Sawaya, M. R. In Crystal Structure Refinement: A Crystallographers Guide to SHELXL; Mueller, P., Ed.; Oxford University Press: Oxford, 2006; Mueller, P. Cryst. Rev. 2009, 15, 57-83, each of which is incorporated by reference in its entirety. All non-hydrogen atoms were refined anisotropically. The hydrogen atoms on the phenyl rings of the [PPN]$^+$ cations and those on solvent molecules were generally included at geometrically calculated positions and refined using a riding model. Crystal data and refinement conditions for the PPN salts of 1-5 are summarized in Tables S1-S3. Crystal structure data for the PPN salts of 1-5 have been deposited to the Cambridge Crystallographic Data Centre with CCDC numbers of 998201-998205, respectively.

Colorless crystals of [PPN]$_2$[P$_4$O$_{12}$H$_2$] ([PPN]$_2$[1] 1) were grown in situ from either the reaction of [PPN]$_4$[P$_4$O$_{12}$].5H$_2$O with (CF$_3$CO$_2$)$_2$O in acetone or the reaction of [PPN]$_2$[P$_4$O$_{11}$] with H$_2$O in acetone. [PPN]$_2$[P$_4$O$_{12}$H$_2$] crystallizes in the orthorhombic space group Pbca, with half of the [P$_4$O$_{12}$H$_2$]$^{2-}$ anion in the asymmetric unit, along with a [PPN]$^+$ countercation. The dihydrogen tetrametaphosphate anion was found to be disordered. All the oxygen atoms were modeled over two positions, which were refined freely within SHELXL while constraining the sum of the occupancies to unity; the relative occupancies of the two alternative sets reached values of 0.58:0.42 at convergence. The disorder was treated with the aid of similarity restraints on the 1,2- and 1,3-distances, as well as rigid bond restraints. See, for example, Thorn, A.; Dittrich, B.; Sheldrick, G. M. Acta Cryst. 2012, 68, 448-451, which is incorporated by reference in its entirety. The hydrogen atoms on the P—OH moieties were placed in calculated positions by referring to a good distance from neighboring P=O acceptors and refined as riding atoms.

Colorless crystals of [PPN]$_2$[P$_4$O$_{11}$] ([PPN]$_2$[2]) were grown from vapor diffusion of diethyl ether into a concentrated solution of 2 in acetonitrile. 2 crystallizes in the monoclinic space group P2$_1$/c with one anion of [P$_4$O$_{11}$]$^{2-}$, one entire cation of [PPN]$^+$, and two half PPN$^+$ countercations in the asymmetric unit. The model contains no disorder and no restraints were applied.

Colorless crystals of [PPN]$_2$[(P$_4$O$_{10}$)(OH)(OMe)] ([PPN]$_2$[3]) were grown from vapor diffusion of diethyl ether into a concentrated solution of [PPN]$_2$[1] in acetonitrile. [PPN]$_2$[1] crystallizes in the monoclinic space group P2$_1$/n. The asymmetric unit comprises one fully occupied [PPN]$^+$ cation and one [(P$_4$O$_{10}$)(OH)(OMe)]$^{2-}$ anion with a crystallographically imposed half occupancy. The latter anion is located near a crystallographic inversion center and it is disordered accordingly. The disorder was refined with the help of the PART-1 instruction. Geometrical restraints as well as similarity restraints on the 1,2- and 1,3-distances and rigid bond restraints were applied. The hydrogen atom on the P—OH moiety and those belonging to the methyl group were placed in calculated positions and refined as riding atoms. The placement of the hydroxyl hydrogen atom was also referred to the distance from the neighboring P=O acceptor. The [PPN]$^+$ cation also was found to be partially disordered. Three of its six phenyl rings were modeled over multiple positions. This disorder also was refined with the aid of geometrical restraints as well as similarity restraints on the 1,2- and 1,3-distances and rigid bond restraints. Similar anisotropic displacement parameters (ADP) were also applied as needed to stabilize the refinement.

Colorless crystals of [PPN]$_2$[Sn(P$_4$O$_{12}$)] ([PPN]$_2$[4]) were grown via vapor diffusion of diethyl ether into a concentrated solution of [PPN]$_2$[4] in acetonitrile. [PPN]$_2$[4] crystallizes in the triclinic space group P1, with one [Sn (P$_4$O$_{12}$)]$^{2-}$ complex anion and two [PPN]$^+$ countercations in the asymmetric unit. One of the phenyl rings belonging to one [PPN]$^+$ cation was modeled over two positions. The relative occupancies of the two alternative sets was refined freely within SHELXL and reached values of 0.69:0.31 at convergence. The disorder was treated with the aid of similarity restraints on the 1,2- and 1,3-distances, as well as rigid bond restraints. Geometrical restraints as well as similar anisotropic displacement parameters (ADP) were also applied. Residual electron density peaks were attributed to disordered solvent molecules. There appears to be a highly disordered diethyl ether molecule and three acetonitrile molecules in a solvent accessible void. The program Squeeze as implemented in Platon was used to remove the contribution of the disordered solvent from the diffraction data. See, for example, van der Sluis, P.; Spek, A. L. Acta Cryst. 1990, 46, 194-201; Spek, A. L. J. Appl. Crystallogr. 2003, 36, 7-13, each of which is incorporated by reference in its entirety. The disorder observed in this case may be attributed to the facility with which crystals of [PPN]$_2$[4] lose solvent.

Colorless crystals of [PPN]$_4$[Cr$_2$(P$_4$O$_{12}$)$_2$] ([PPN]$_4$[5]) were grown via vapor diffusion of diethyl ether into a concentrated solution of [PPN]$_4$[5] in acetonitrile. [PPN]$_4$[5] crystallizes in the monoclinic space group P2$_1$/c. The asymmetric unit comprises one fully occupied [PPN]$^+$ cation and one-half [Cr$_2$(P$_4$O$_{12}$)$_2$]$^{4-}$ dichromium(II) cage with a crystallographically imposed half occupancy, along with some disordered solvent (ca. 0.825 acetonitrile molecules and 0.175 diethyl ether molecules per asymmetric unit). The disordered solvent occupies large voids between neighboring dichromium cages piled along the crystallographic α axis. Similarity restraints on the 1,2- and 1,3-distances and displacement parameters along with rigid bond restraints were applied to the dichromium(II) complex anion. The disordered solvent was refined as well with the help of similarity restraints on the 1,2- and 1,3-distances and displacement parameters as well as rigid bond restraints for anisotropic displacement parameters. Geometrical restraints were also applied to the disordered diethyl ether molecule.

TABLE S1

| crystallographic data for compounds [PPN]$_2$[1]1 and [PPN]$_2$[2] | | |
|---|---|---|
| | [PPN]$_2$[P$_4$O$_{12}$H$_2$] (1) | [PPN]$_2$[P$_4$O$_{11}$] (2) |
| Reciprocal Net code/CCDC No. | XS_13135/998201 | 13013/998202 |
| Empirical formula FW (g/mol) | C$_{72}$H$_{62}$N$_2$O$_{12}$P$_8$, 1395.00 | C$_{72}$H$_{64}$N$_2$O$_{11}$P$_8$, 1376.98 |
| Crystal size (mm$^3$) | 0.50 × 0.40 × 0.30 | 0.26 × 0.22 × 0.14 |
| Temperature (K) | 100(2) | 100(2) |
| Wavelength (Å) | 0.71073 | 0.71073 |
| Crystal system, Space group | Orthorhmetric Pbca | Monoclinic, P2$_1$/c |
| a (Å), α(°) | 19.9148(9), 90 | 17.4891(13), 90.00 |
| b (Å), β(°) | 16.3924(7), 90 | 15.2366(11), 104.2850(10) |
| c (Å), γ(°) | 19.9502(9), 90 | 25.1850(18), 90.00 |
| Volume (Å$^3$) | 6512.8(5) | 6503.6(8) |
| Z | 4 | 4 |
| Density (calc., g/cm$^3$) | 1.423 | 1.406 |
| Absorption coefficient (mm$^{-1}$) | 0.281 | 0.279 |
| F(000) | 2896 | 2856 |
| Theta range for data collection (°) | 1.906 to 30.579 | 1.201 to 30.507 |
| Index ranges | −26 ≤ h ≤ 28 | −24 ≤ h ≤ 24 |
| | −17 ≤ k ≤ 23 | −21 ≤ k ≤ 21 |
| | −28 ≤ l ≤ 26 | −35 ≤ l ≤ 35 |
| Reflections collected | 75134 | 183927 |
| Independent reflections, R$_{int}$ | 9957(0.0383) | 19837(0.0566) |
| Completeness to θ = 25.242° | 100.0% | 100% |
| Refinement method | Full-matrix least-squares on F$^2$ | Full-matrix least squares on F$^2$ |
| Data/restraints/parameters | 9957/256/481 | 19837/0/841 |
| Goodness-of-fit on F$^2$ | 1.036 | 1.044 |
| Final R indices [I > 2σ(I)] | R$_1$ = 0.0373, wR$_2$ = 0.0971 | R$_1$ = 0.0407, wR$_2$ = 0.1010 |
| R indices (all data) | R$_1$ = 0.0467, wR$_2$ = 0.1040 | R$_1$ = 0.0581, wR$_2$ = 0.1127 |
| Extinction coefficient | n/a | n/a |
| Largest diff. peak and hole (e · Å$^{-3}$) | 0.556 and −0.540 | 0.634 and −0.565 |

TABLE S2

| crystallographic data for compounds [PPN]$_2$[3] | |
|---|---|
| | [PPN]$_2$[P$_4$O$_{10}$)(OH)(OMe)] (3) |
| Reciprocal Net code/CCDC No. | X8_13177/998203 |
| Empirical formula, FW (g/mol) | C$_{74}$H$_{64}$N$_2$O$_{12}$P$_8$, 1409.02 |
| Crystal size (mm$^3$) | 0.180 × 0.070 × 0.020 |
| Temperature (K) | 100(2) |
| Wavelength (Å) | 0.71073 |
| Crystal system, Space group | Monoclinic, P2$_1$/n |
| a (Å), α(°) | 12.3062(11), 90.00 |
| b (Å), β(°) | 13.1808(12), 195.085(2) |

TABLE S2-continued crystallographic data for compounds [PPN]$_2$[3]

| | [PPN]$_2$[P$_4$O$_{10}$)(OH)(OMe)] (3) |
|---|---|
| c (Å), γ(°) | 21.0215(18), 90.00 |
| Volume (Å$^3$) | 3292.3(5) |
| Z | 2 |
| Density (calc., g/cm$^3$) | 1.421 |
| Absorption coefficient (mm$^{-1}$) | 0.279 |
| F(000) | 1464 |
| Theta range for data collection (°) | 1.746 to 30.032 |
| Index ranges | −17 ≤ h ≤ 17 |
| | −18 ≤ k ≤ 18 |
| | −29 ≤ l ≤ 29 |
| Reflections collected | 122877 |
| Independent reflections, R$_{int}$ | 9628(0.0519) |
| Completeness to θ = 25.242° | 99.9% |
| Refinement method | Full-matrix least-squares on F$^2$ |
| Data/restraints/parameters | 9628/1269/664 |
| Goodness-of-fit on F$^2$ | 1.035 |
| Final R indices [I > 2σ(I)] | R$_1$ = 0.0592, wR$_2$ = 0.1558 |
| R indices (all data) | R$_1$ = 0.0796, wR$_2$ = 0.1741 |
| Extinction coefficient | n/a |
| Largest diff. peak and hole (e · Å$^{-3}$) | 0.806 and −0.662 |

TABLE S3

Crystallographic data for compounds [PPN]$_2$[4]- and [PPN]$_4$[5]

| | [PPN]$_2$[Sn(P$_4$O$_{12}$)] (4) | [PPN]$_4$[Cr$_2$(P$_4$O$_{12}$)$_2$] (5) |
|---|---|---|
| Reciprocal Net code/CCDC No. | XS_13157/998204 | XS_13191/998205 |
| Empirical formula, FW (g/mol) | C$_{72}$H$_{68}$N$_2$O$_{12}$P$_8$Sn, C$_2$H$_{10}$O, 3C$_2$H$_3$N, 1708.95 | C$_{141}$H$_{120}$N$_1$O$_{22}$P$_{14}$Cr$_2$, 0.7C$_4$H$_{14}$O, 3.3C$_2$H$_4$N, 3077.45 |
| Crystal size (mm$^3$) | 0.33 × 0.24 × 0.16 | 0.26 × 0.06 × 0.50 |
| Temperature (K) | 100(2) | 100(2) |
| Wavelength (Å) | 0.71073 | 0.71073 |
| Crystal system, Space group | Triclinic P1 | Monoclinic P2$_1$/c |
| a (Å), α(°) | 11.1026(13), 99.215(3) | 9.1075(6), 90 |
| b (Å), β(°) | 13.4157(15), 98.482(3) | 15.6493(10), 96.5610(10) |
| c (Å), γ(°) | 26.153(3), 92.599(3) | 24.7710(15), 90 |
| Volume (Å$^3$) | 3793.3(8) | 3507.4(4) |
| Z | 2 | 1 |
| Density (calc., g/cm$^3$) | 1.496 | 1.457 |
| Absorption coefficient (mm$^{-1}$) | 0.575 | 0.414 |
| F(000) | 1760 | 1594 |
| Theta range for data collection (°) | 1.542 to 31.538 | 1.542 to 30.037 |
| Index ranges | −16 ≤ h ≤ 16 | −12 ≤ h ≤ 12 |
| | −43 ≤ k ≤ 19 | −22 ≤ k ≤ 22 |
| | −38 ≤ l ≤ 38 | −34 ≤ l ≤ 34 |
| Reflections collected | 147447 | 113823 |
| Independent reflections, R$_{int}$ | 25169 (0.0356) | 10266(0.0620) |
| Completeness to θ = 25.242° | 100.0% | 100% |
| Refinement method | Full-matrix least-squares on F$^2$ | Full-matrix least-squares on F$^2$ |
| Data/restraints/parameters | 25169/165/875 | 10266/563/632 |
| Goodness-of-fit on F$^2$ | 1.045 | 1.036 |
| Final R indices [I > 2σ(I)] | R$_1$ = 0.0299, wR$_2$ = 0.0768 | R$_1$ = 0.0494, wR$_2$ = 0.1274 |
| R indices (all data) | R$_1$ = 0.0352, wR$_2$ = 0.0790 | R$_1$ = 0.0731, wR$_2$ = 0.1448 |
| Extinction coefficient | n/a | n/a |
| Largest diff. peak and hole (e · Å$^{-3}$) | 0.596 and −0.582 | 0.777 and −0.519 |

It was further examined whether the protonolysis protocol can be applied to other basic leaving groups, such as acetylacetate (acac). Under ambient conditions in an open atmosphere, treatment of [PPN]$_2$[P$_4$O$_{12}$H$_2$] ([PPN]$_2$[1]) with 1 equivalent of VO(acac)$_2$ in wet acetone afforded the formation of binary vanadyl(IV) tetrametaphosphate [PPN]$_4$[(VO)$_2$(P$_4$O$_{12}$)$_2$] ([PPN]$_4$[6]) in 80% isolated yield. Single crystals suitable for an X-ray diffraction study were grown from a concentrated acetone solution. The solid-state structure revealed a V . . . V distance of 4.260 Å. In a similar manner, the titanyl(IV) tetrametaphosphate dimer [PPN]$_4$[(OTi)$_2$(P$_4$O2)$_2$] ([PPN]$_4$[7]) was also accessed in 60% isolated yield from the reaction of [PPN]$_2$[P$_4$O$_{12}$H$_2$] with 1 equivalent of TiO(acac)$_2$. The diamagentic nature of Ti(IV) allows the characterization of [PPN]$_4$[7] by NMR spectroscopy and possibly facilitates the future investigation on the reactivity of [PPN]$_4$[7]. In the $^{31}$Pt{$^1$H} NMR spectrum, a singlet resonance at −27.61 ppm was observed speaking for identical tetrametaphosphte phosphorus atoms. X-ray quality crystals of [PPN]$_4$[(OTi)$_2$(P$_4$O$_{12}$)$_2$] ([PPN]$_4$[7]) were grown from a acetone:MeCN (10:1) mixture at room temperature.

Figure 32:
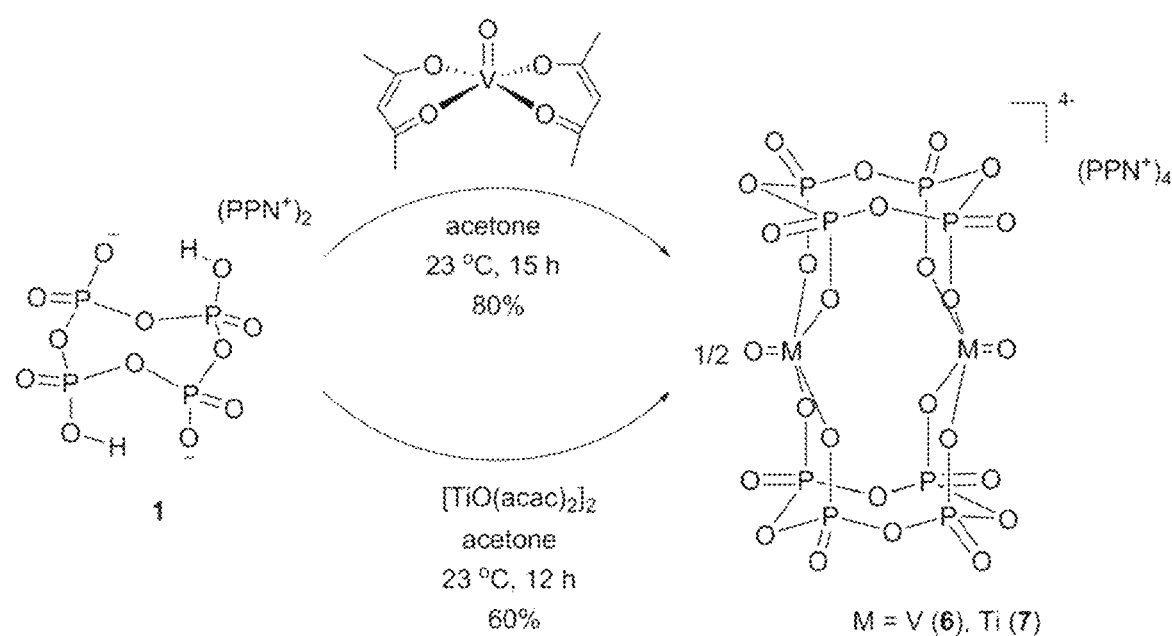
FIG. 32 shows a synthetic route to the PPN salts of binary vanadyl 6 and titanyl tetrametaphosphate dimer 7 from 1.
Figure 35:
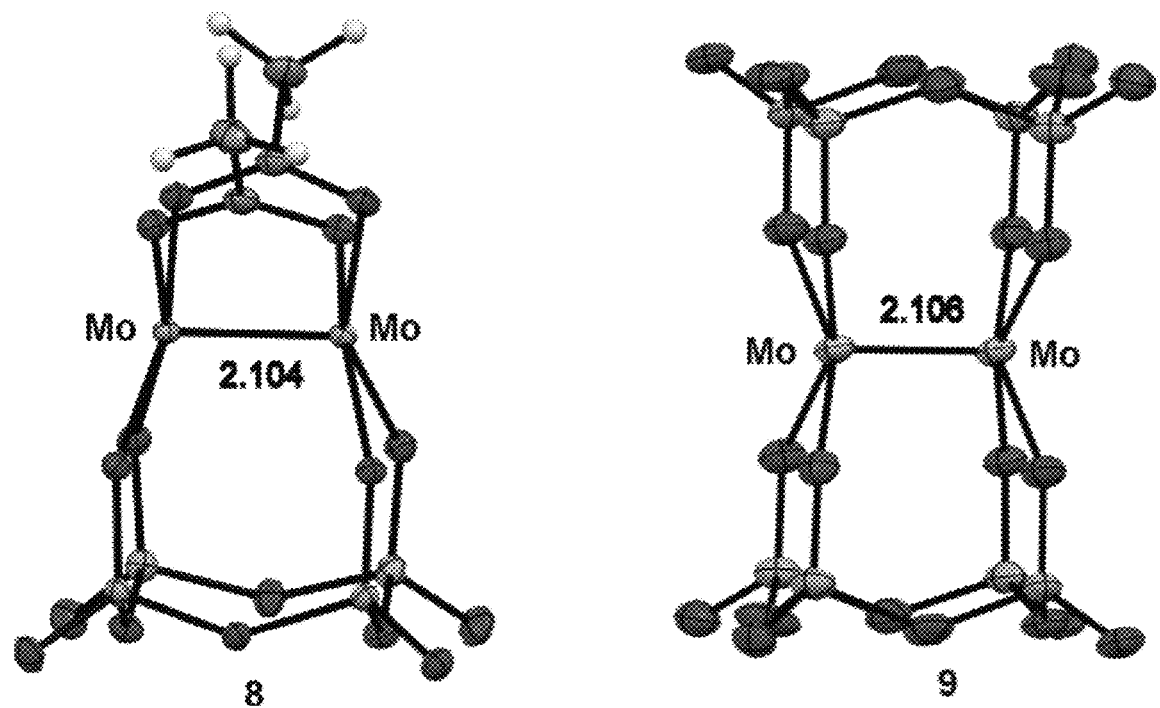
FIG. 35 shows a solid-state molecular structure of quadruple bonded binary molybdenum tetrametaphsophates 8 and 9 with ellipsoids at the 50% probability level and [PPN]+ cations omitted for clarity.
Figure 36:
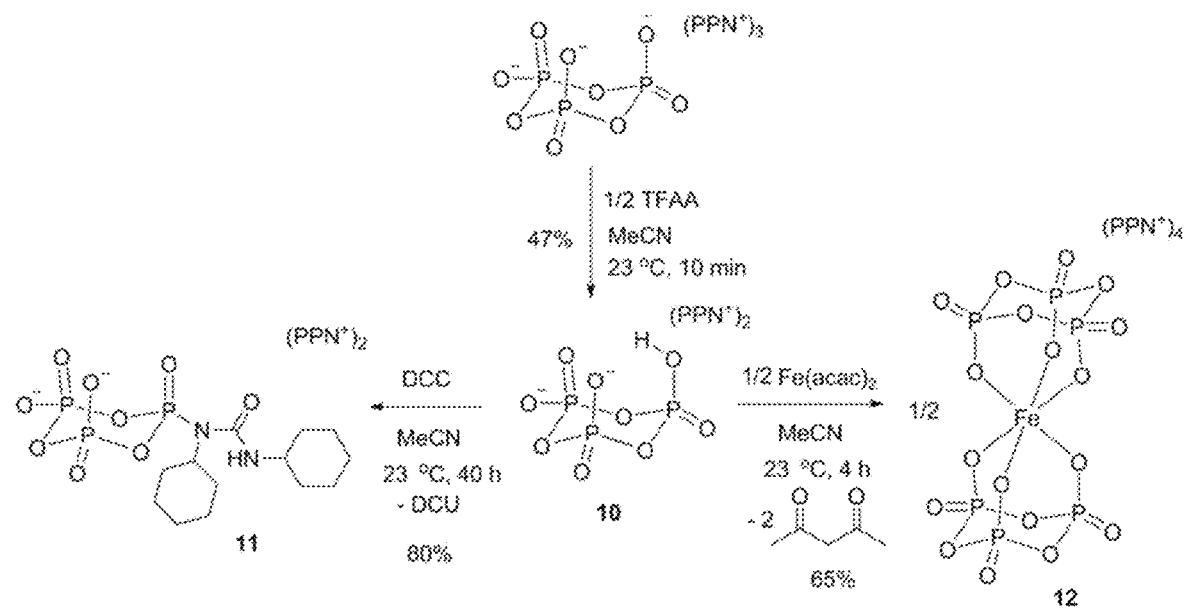
FIG. 36 shows reactivity of $[PPN]_2[P_3O_9H]$ ($[PPN]_2[10]$) toward DCC and Fe(acac)$_2$.

FIG. 32 shows synthetic route to the PPN salts of binary vanadyl 6 and titanyl tetrametaphosphate dimer 7 from 1.

Due to the strong acidity of [PPN]$_2$[P$_4$O$_{12}$H$_2$] ([PPN]$_2$[1]), even acetate ([OAc]$^+$) can be used as a basic ligand in the protonolysis reaction. Treatment of [PPN]$_2$[P$_4$O$_{12}$H$_2$] with 1 equivalent of quadruple bonded Mo$_2$(OAc)$_4$ in acetonitrile afforded within 20 min at room temperature the tetrametaphosphate dimolybdenum diacetate species [PPN]$_2$[Mo$_2$(P$_4$O$_{12}$)(OAc)$_2$] ([PPN]$_2$[8]) in 88% isolated yield. Essentially two acetate ligands can be easily replaced by tetrametaphosphate via protonolysis at room temperature while the other two acetates remained rather reluctant to dissociate from the Mo centers. Nevertheless, at higher temperature of 80° C., the reaction of Mo$_2$(OAc)$_4$ with 2 equivalents of [PPN]$_2$[P$_4$O$_{12}$H$_2$] afforded the fully substituted product [PPN]$_4$[Mo$_2$(P$_4$O$_{12}$)$_2$] ([PPN]$_4$[9]) in 61% isolated yield. The structures of 8 and 9 were established by X-ray diffraction studies. A short Mo . . . Mo distance of 2.104 (8) or 2.106 (9) Å indicates not only a strong bonding (possibly still a quadruple bond) between the two molybdenum atoms, but also the flexibility of tetrametaphosphate in accommodating two metal centers in a wide range of metal-metal distances.

The "protonation" protocol was also applied to the trimetaphosphate chemistry. Treatment of $[PPN]_3[P_3O_9]\cdot H_2O$ with half equivalent of trifluoroacetic anhydride (TFAA) in acetone at 23° C. resulted in the quantitative formation of the PPN salt of monohydrogen trimetaphosphate $[PPN]_2[P_3O_9H]$ ($[PPN]_2[10]$), which was isolated as crystalline solids in 47% yield. The presence of acidic P—OH groups is evidenced by a broad singlet at 11.63 ppm in the $^1H$ NMR spectrum recorded in $CD_3CN$ at 23° C. Notably the chemical shift of P—OH group is strongly affected by the amount of co-crystallized THF, as a result of intermolecular hydrogen bonding. The more THF is present, the broader and high-field shift of the resonance is observed. In the $^{31}P\{^1H\}$ NMR spectrum, a singlet resonance at −20.26 ppm was observed indicating of the fluxional behavior of the acidic hydrogen.

Figure 37:
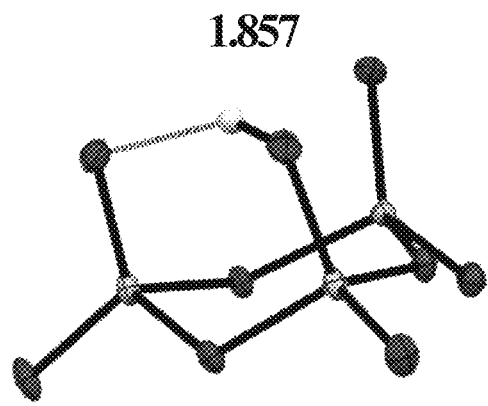
FIG. 37 shows solid-state molecular structure of $[P_3O_9H]^{2-}$ (10) with ellipsoids at the 50% probability level and [PPN]+ cations omitted for clarity.
Figure 38:
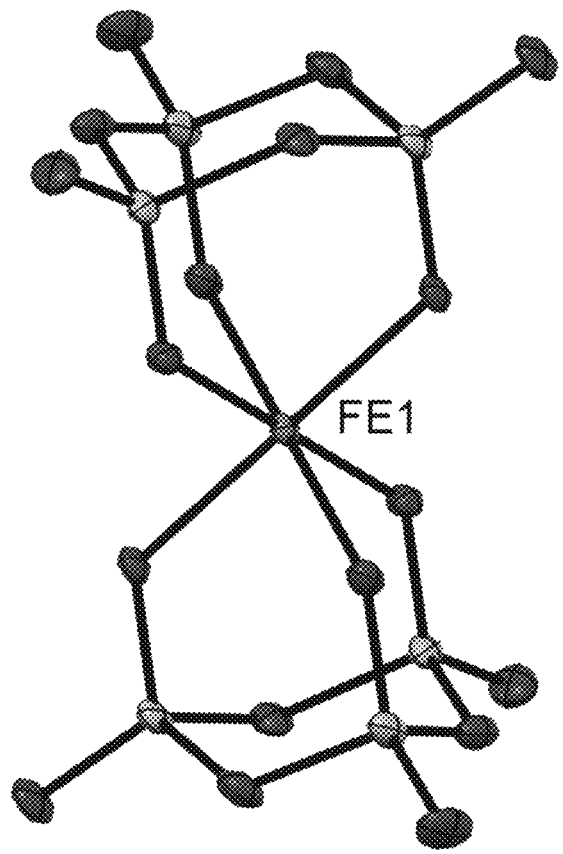
FIG. 38 shows solid-state molecular structure of $[Fe(P_3O_9)_2]_4^-$ (12) with ellipsoids at the 50% probability level and [PPN]+ cations omitted for clarity.
Figure 39:
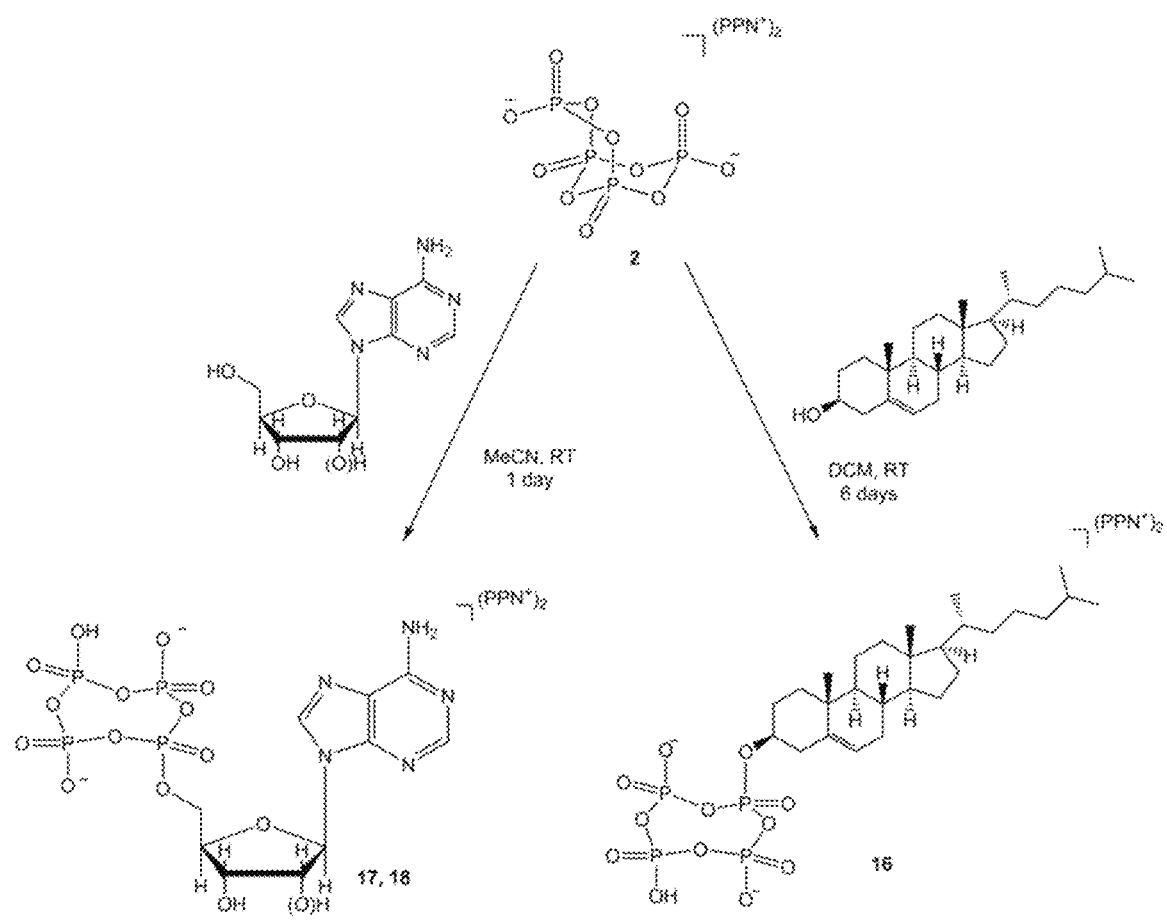
FIG. 39 shows reactivity of $[PPN]_2[P_4O_{11}]$ ($[PPN]_2[2]$) towards cholesterol, adenosine and 2'-deoxyadenosine.
Figure 40:
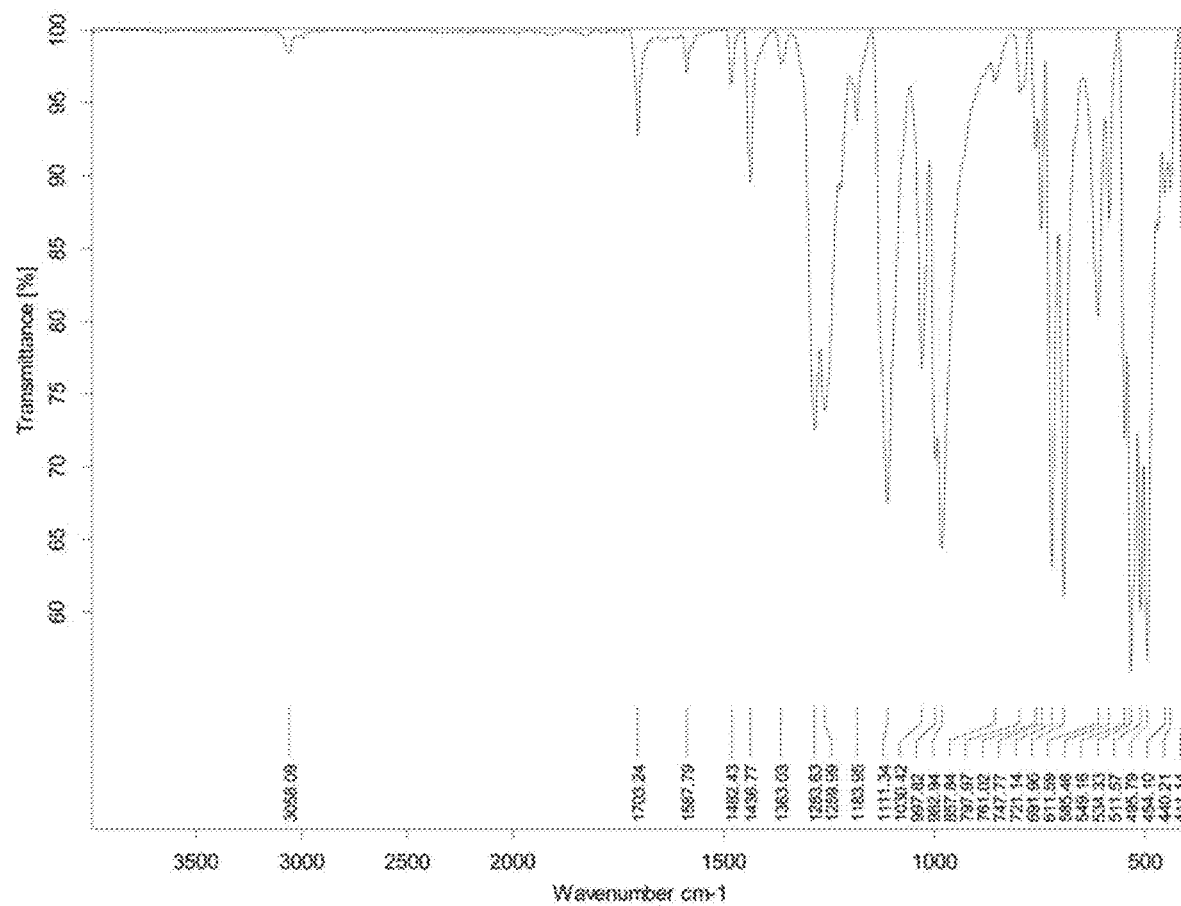
FIG. 40 shows ATR-IR spectrum of solid $[PPN]_4[(VO)_2(P_4O_{12})_2]$ ($[PPN]_4[6]$)
Figure 41:
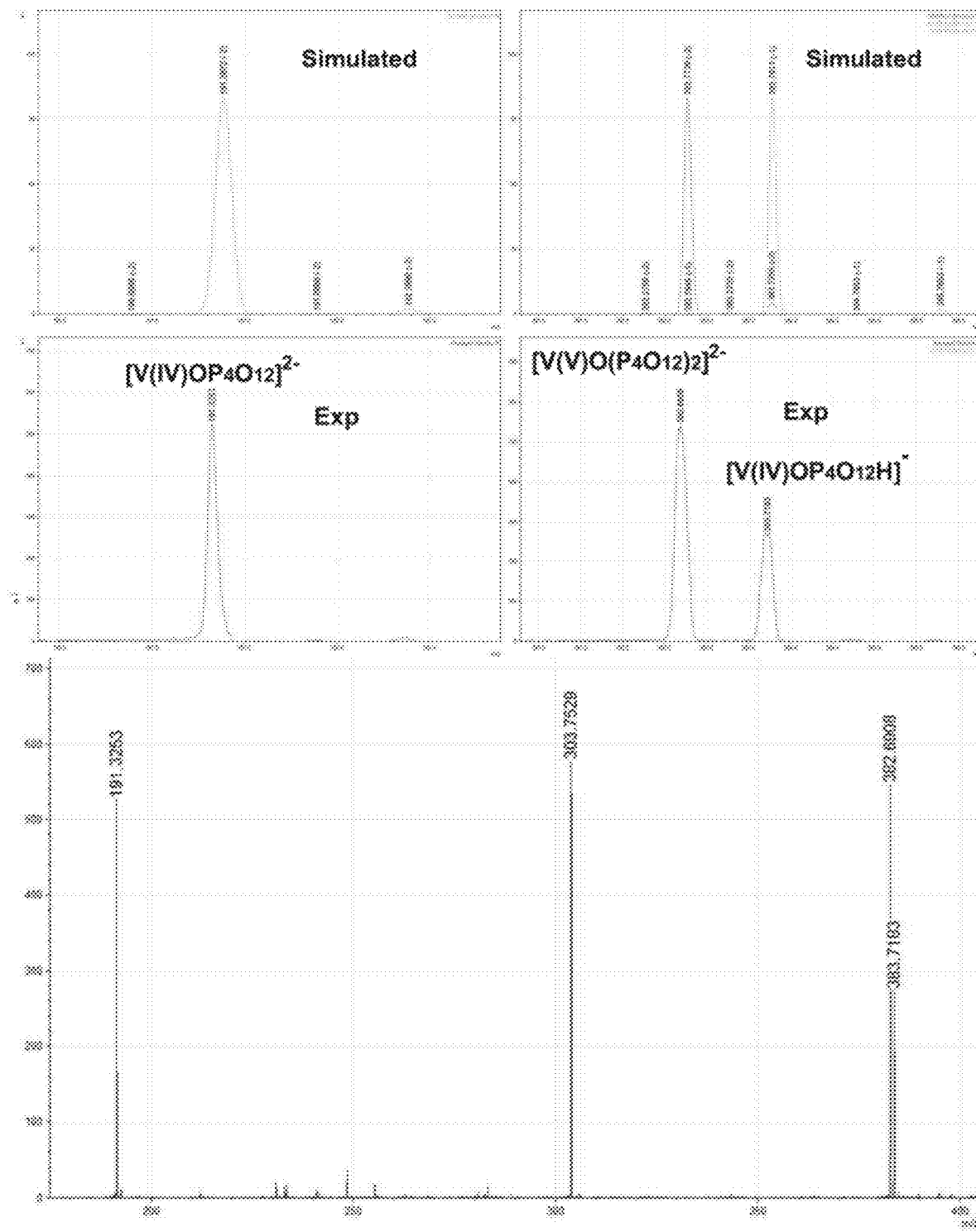
FIG. 41 shows ESI-MS(−) spectrum of $[PPN]_4(VO)_2(P_4O_{12})_2]$ ($[PPN]_4[6]$).
Figure 42:
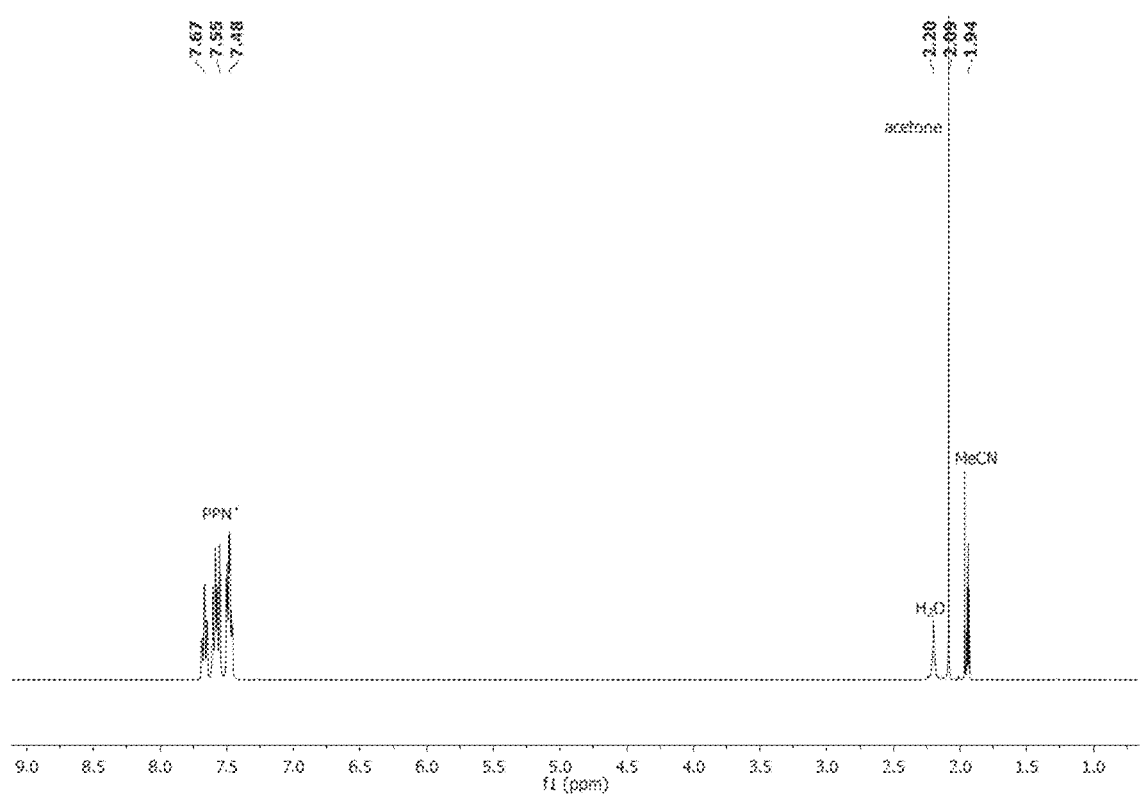
FIG. 42 shows $^1H$ NMR (400.1 MHz) of $[PPN]_4[OTiP_4O_{12}]2$ ($[PPN]_4[7]$) recorded at 23° C. in $CD_3CN$.
Figure 43:
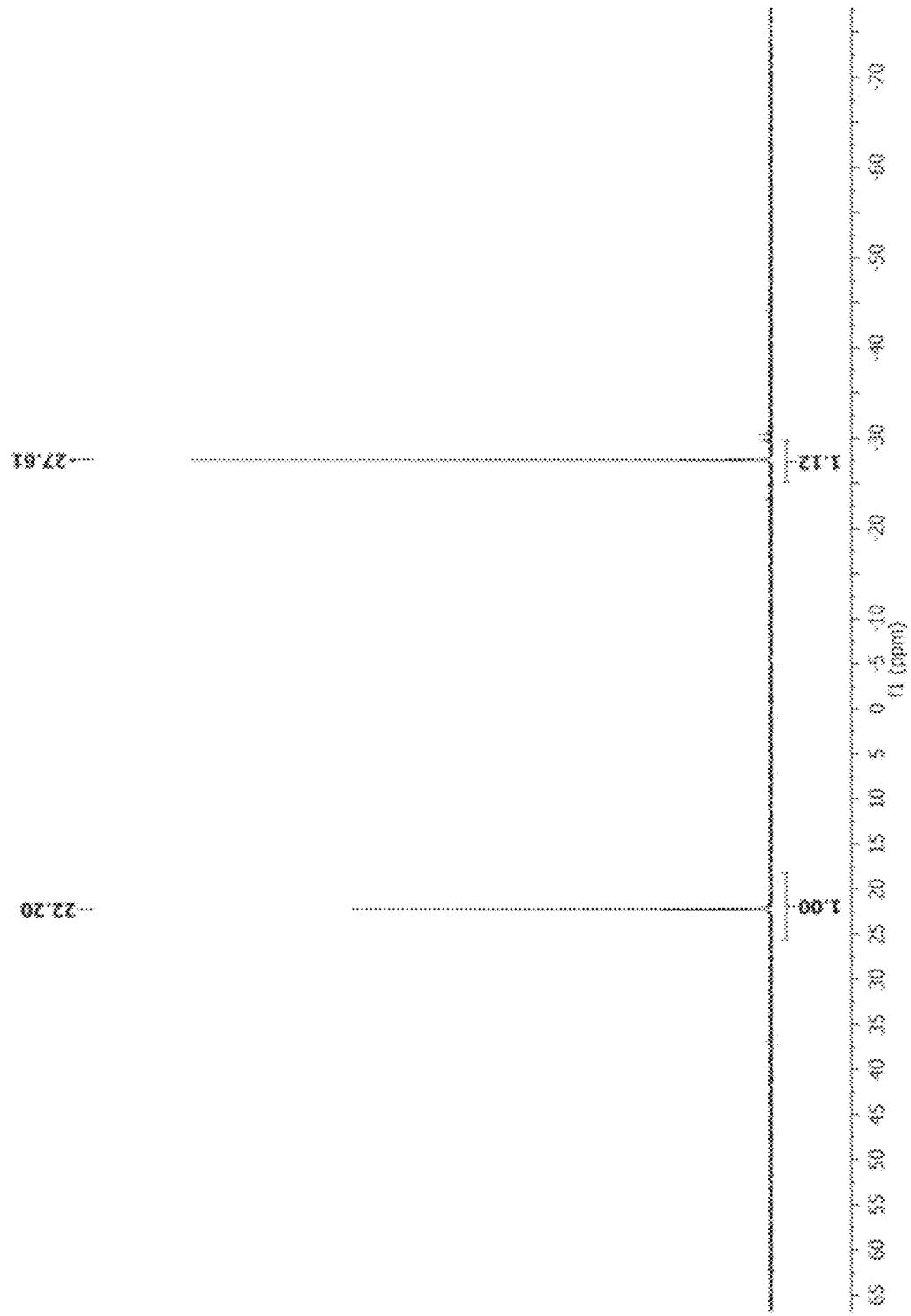
FIG. 43 shows $^{31}P\{^1H\}$ NMR (122.0 MHz) of $[PPN]_4[(OTi)_2(P_4O_{12})_2]$ ($[PPN]_4[7]$) recorded at 23° C. in $CD_3CN$.
Figure 44:
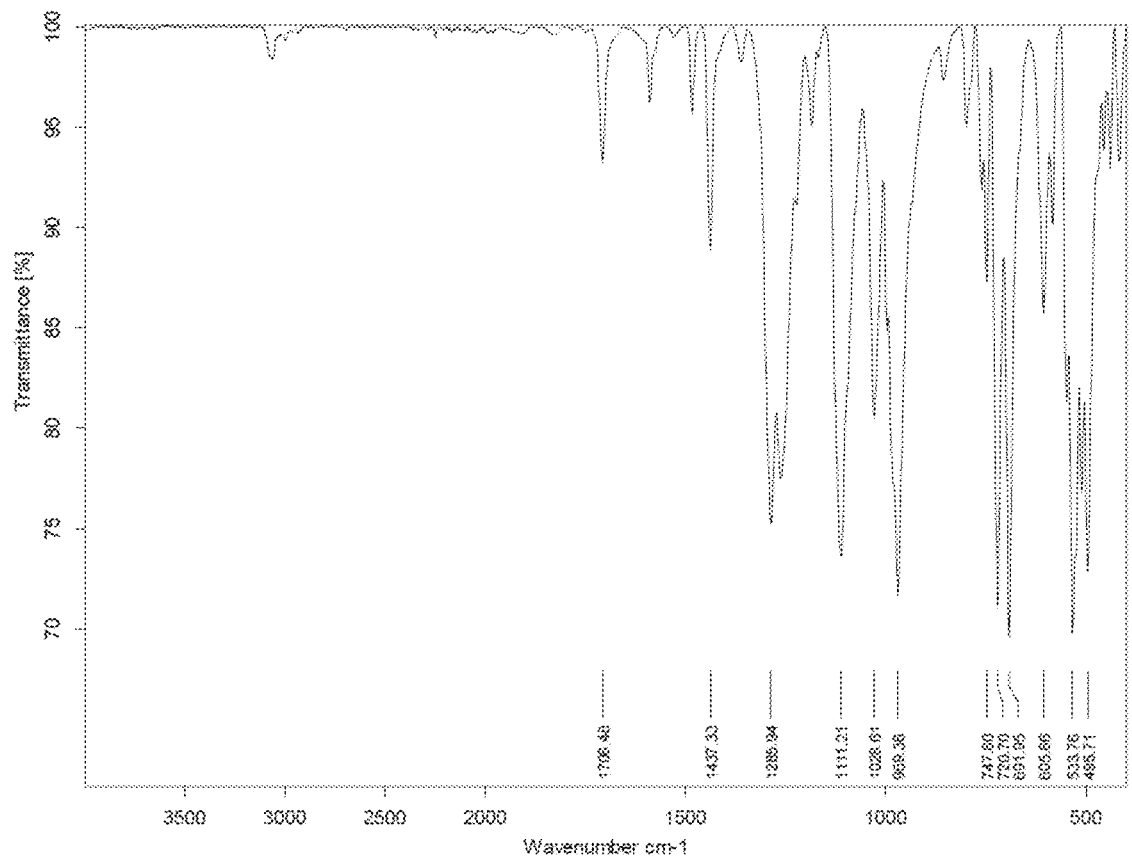
FIG. 44 shows ATR-IR spectrum of solid $[PPN]_4[(OTi)_2(P_4O_{12})_2]$ ($[PPN]_4[7]$)
Figure 45:
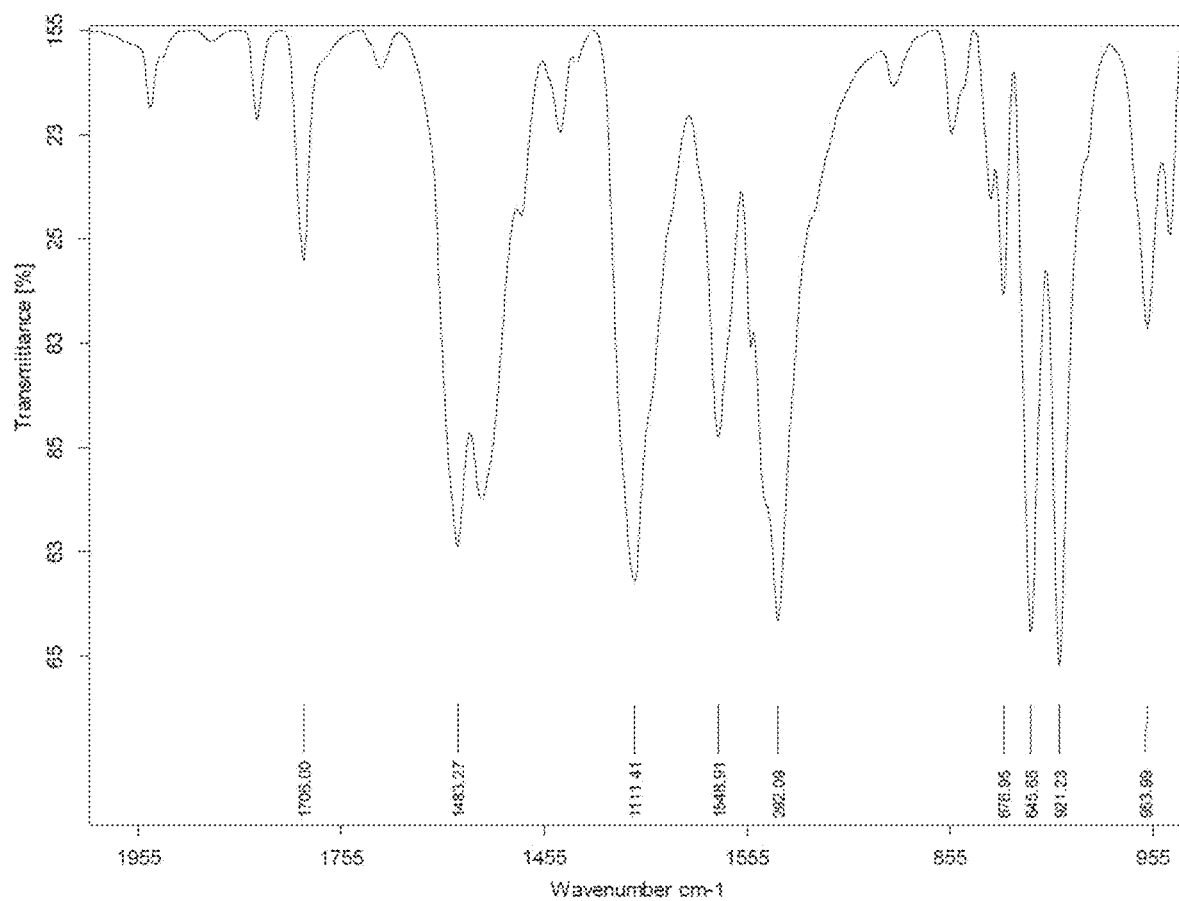
FIG. 45 shows Zoomed-in ATR-IR spectrum of solid $[PPN]_4[(OTi)_2(P_4O_{12})_2]$($[PPN]_4[7]$)
Figure 46:
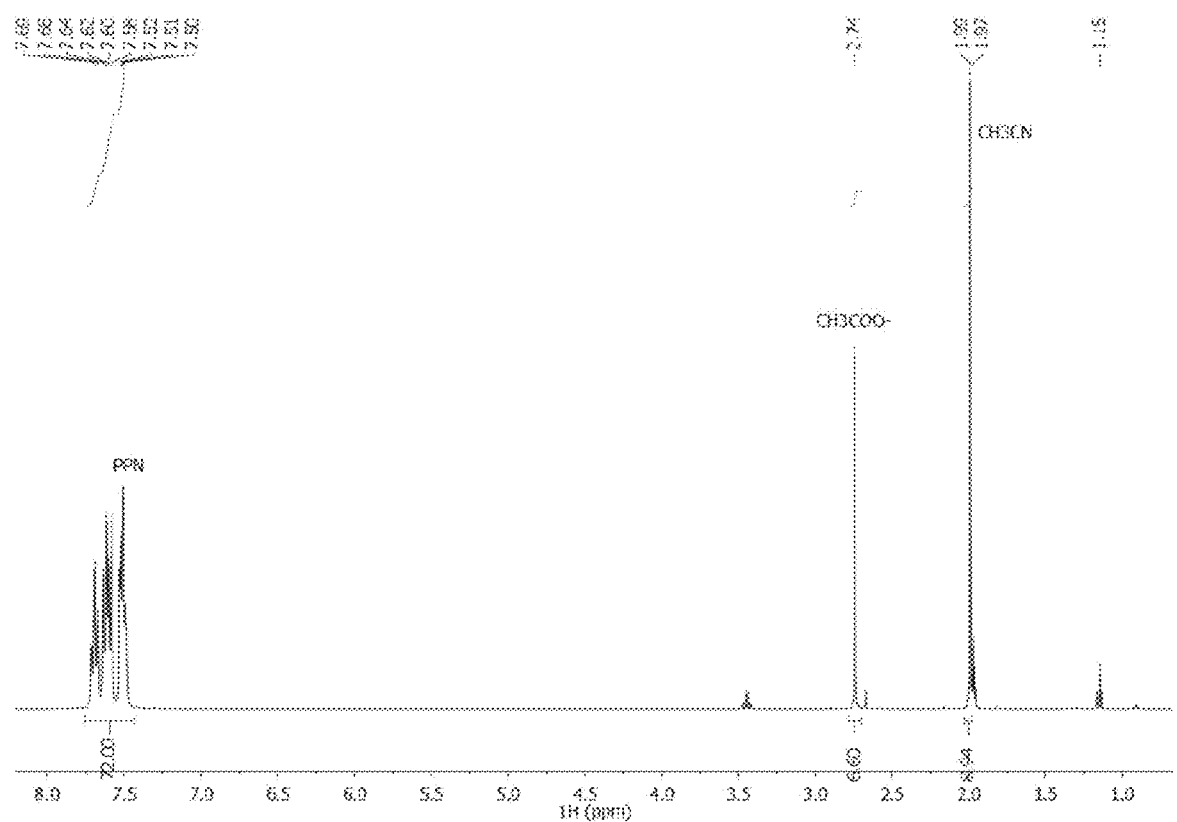
FIG. 46 shows $^1H$ NMR (400.1 MHz) of $[PPN]_2[Mo_2(P_4O_{12})(OAc)_2]$ (−$[PPN]_2$ [8]) recorded at 23° C. in $CD_3CN$.
Figure 47:
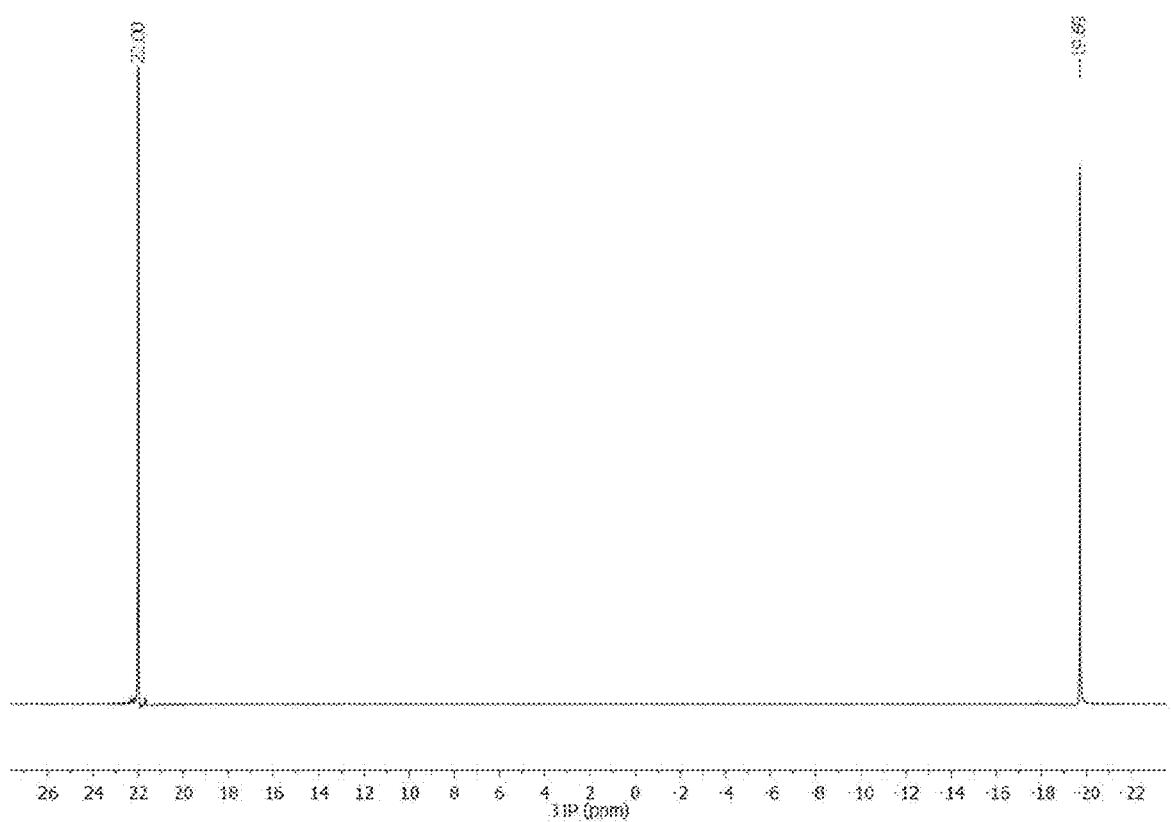
FIG. 47 shows $^{31}P\{^1H\}$ NMR (161.9 MHz) of $[PPN]_2[Mo_2(P_4O_{12})(OAc)_2]$ ($[PPN]_2[8]$) recorded at 23° C. in $CD_3CN$.
Figure 48:
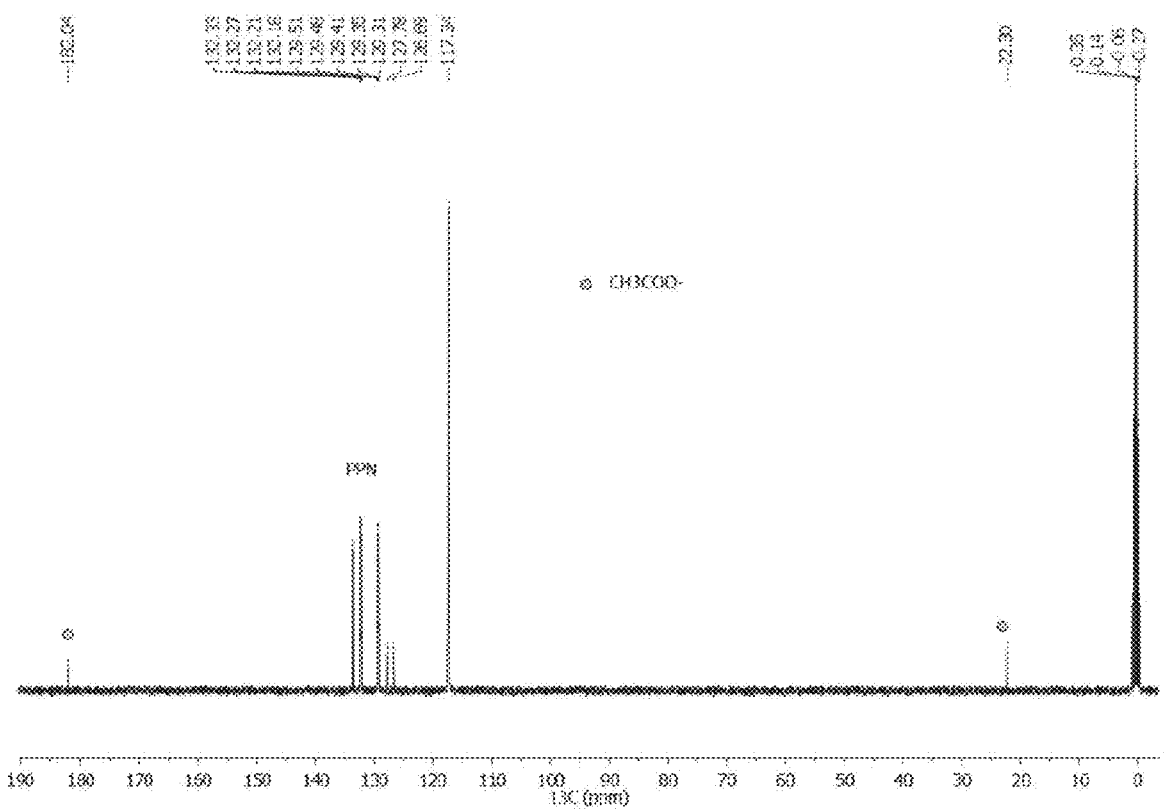
FIG. 48 shows $^{13}C$ NMR (100 MHz) of $[PPN]_2[Mo_2(P_4O_{12})(OAc)_2]$ ($[PPN]_2[8]$) recorded at 23° C. in $CD_3CN$.
Figure 49:
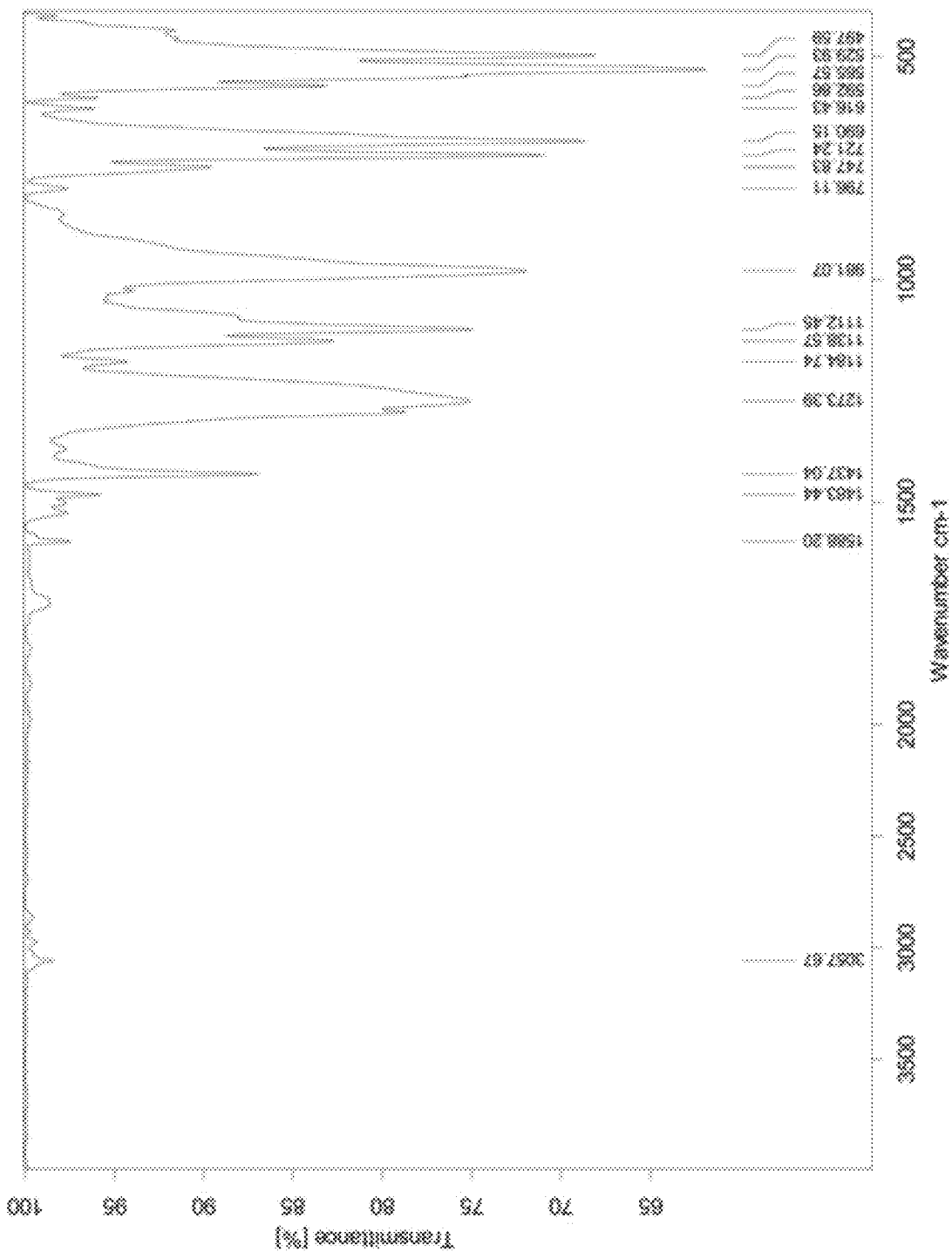
FIG. 49 shows ATR-IR spectrum of solid $[PPN]_2[Mo_2(P_4O_{12})(OAc)_2]$ ($[PPN]_2[8]$).
Figure 50:
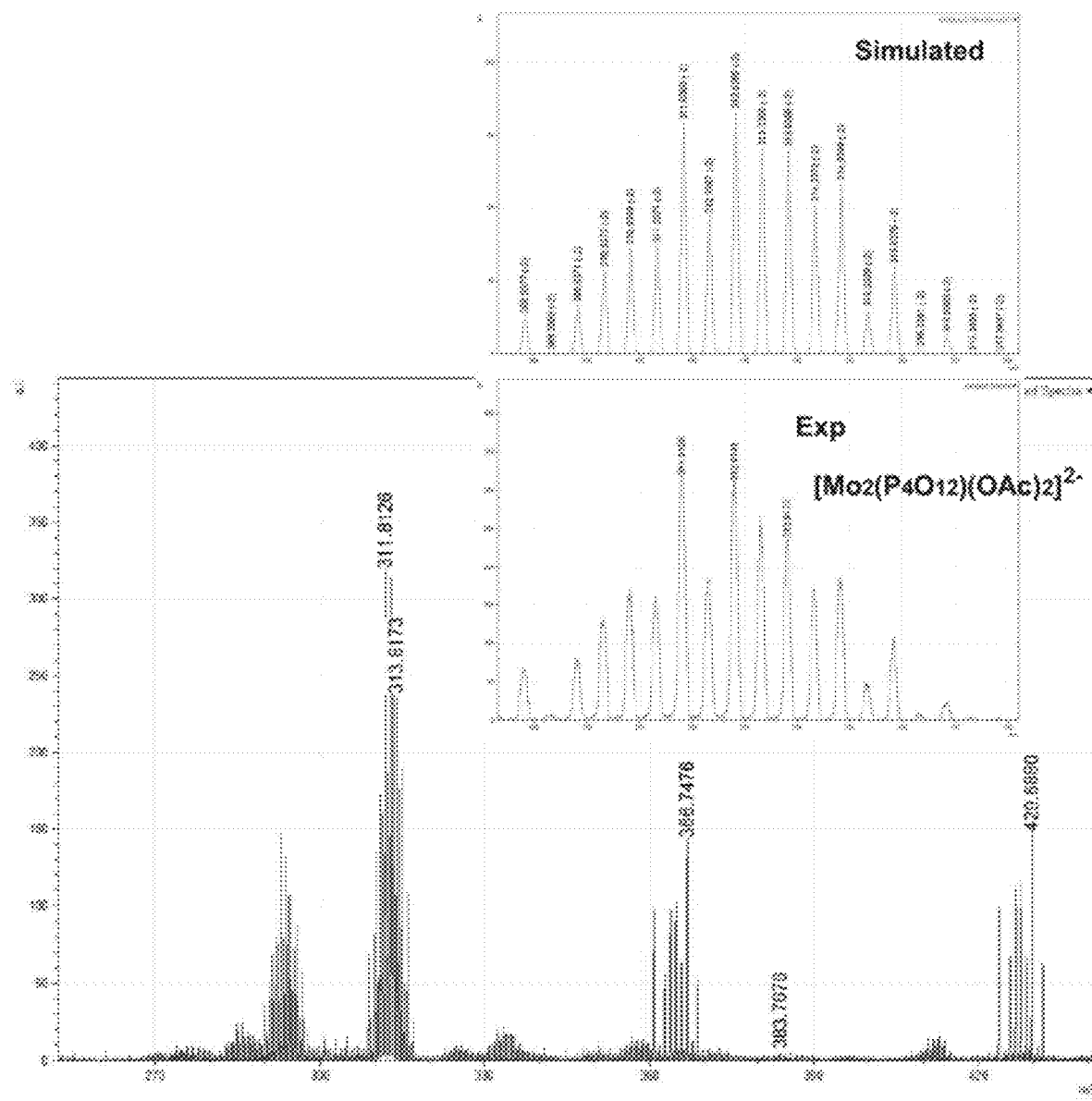
FIG. 50 shows ESI-MS(−) spectrum of $[PPN]_2[Mo_2(P_4O_{12})(OAc)_2]$ ($[PPN]_2[8]$)
Figure 51:
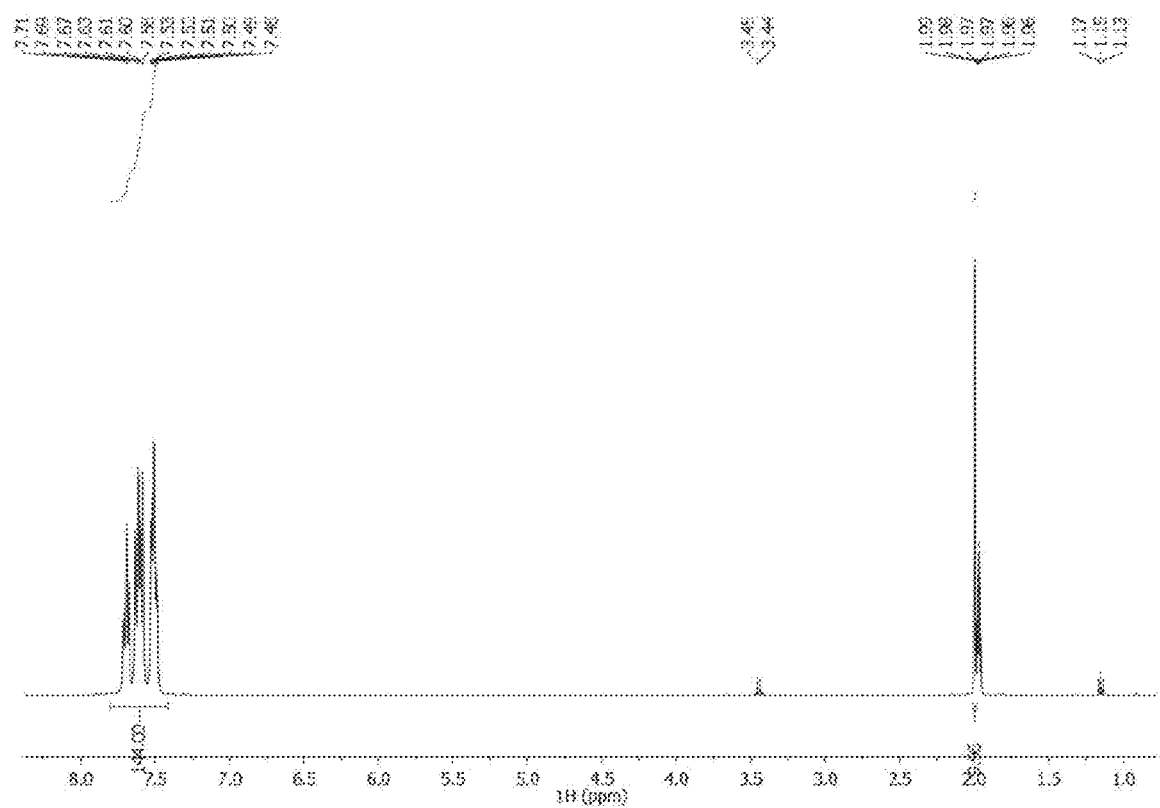
FIG. 51 shows 1H NMR (400.1 MHz) of $[PPN]_4[Mo_2(P_4O_{12})_2]$ ($[PPN]_4[9]$) recorded at 23° C. in $CD_3CN$
Figure 52:
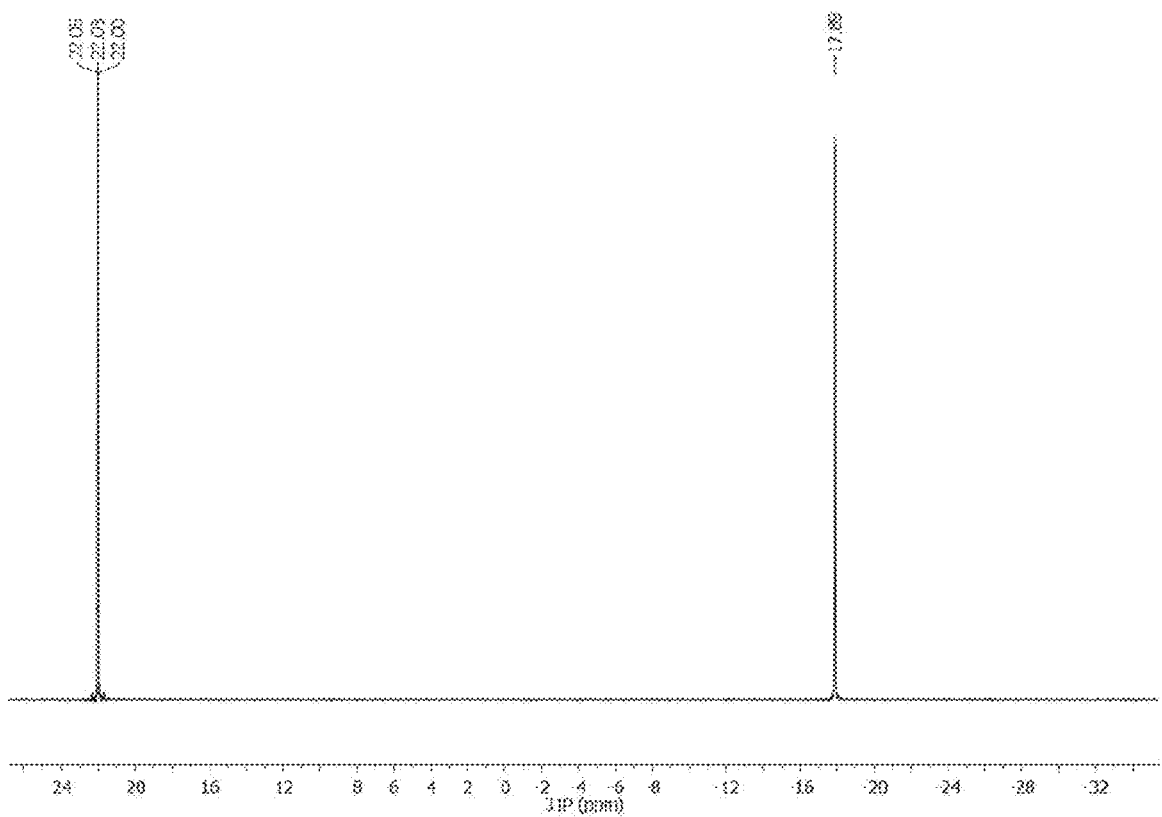
FIG. 52 shows $^{31}P\{^1H\}$ NMR (161.9 MHz) of $[PPN]_4[Mo_2(P_4O_{12})_2]$ ($[PPN]_4[9]$) recorded at 23° C. in $CD_3CN$.
Figure 53:
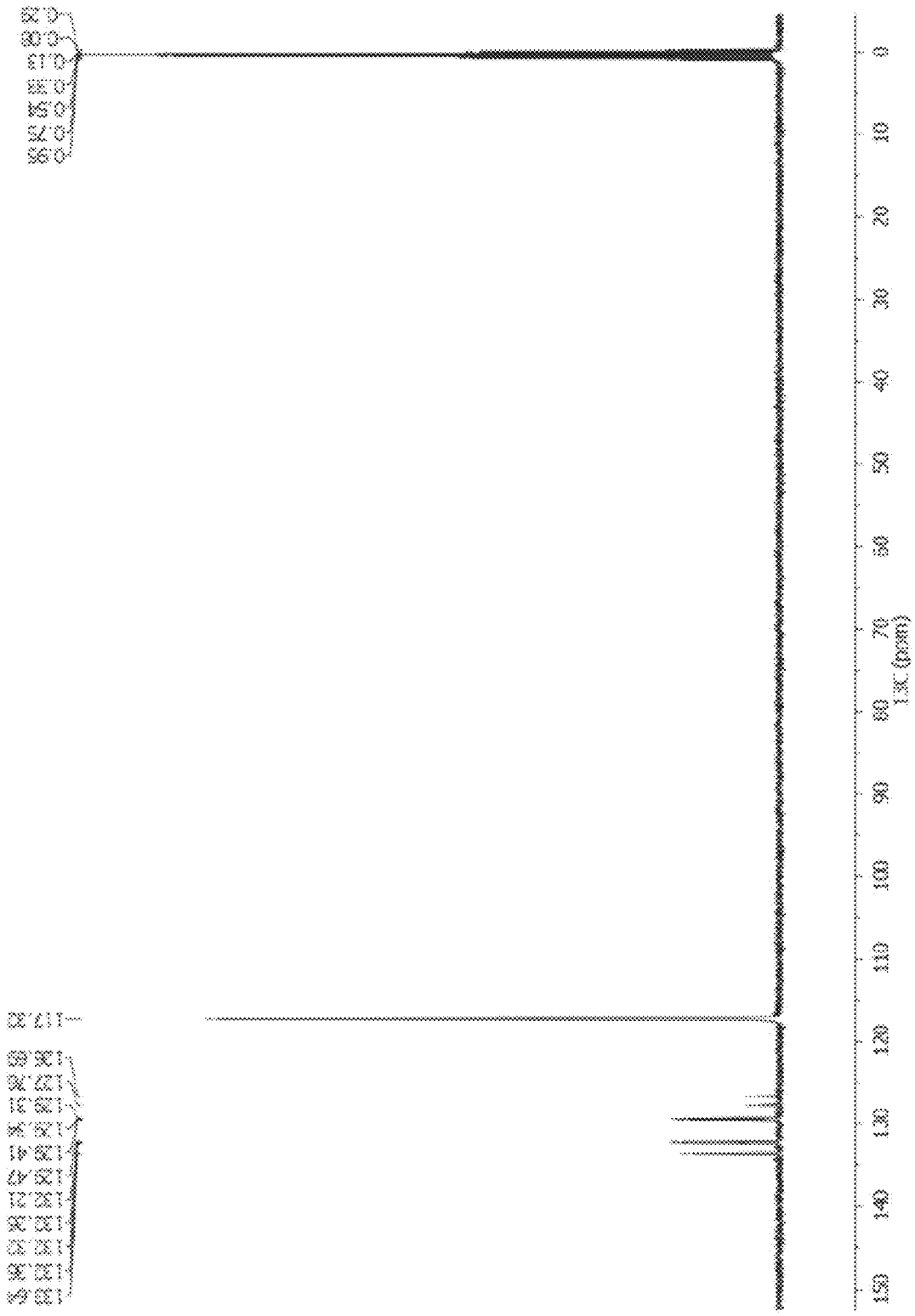
FIG. 53 shows $^{13}C$ NMR (100 MHz) of $[PPN]_4[Mo_2(P_4O_{12})_2]$ ($[PPN]_4[9]$) recorded at 23° C. in $CD_3CN$
Figure 54:
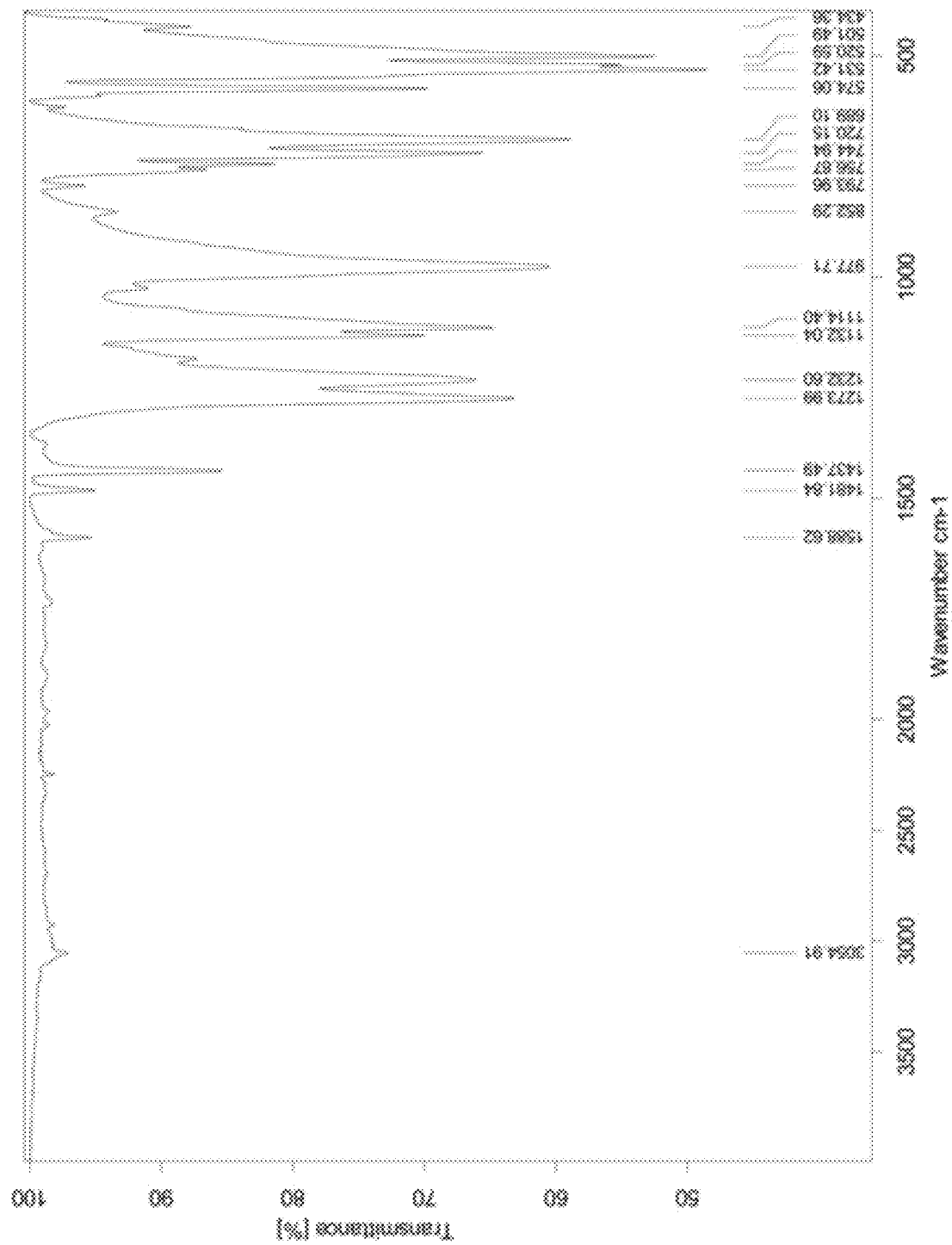
FIG. 54 shows ATR-IR spectrum of $[PPN]_4[Mo_2(P_4O_{12})_2]$ ($[PPN]_4[9]$).
Figure 55:
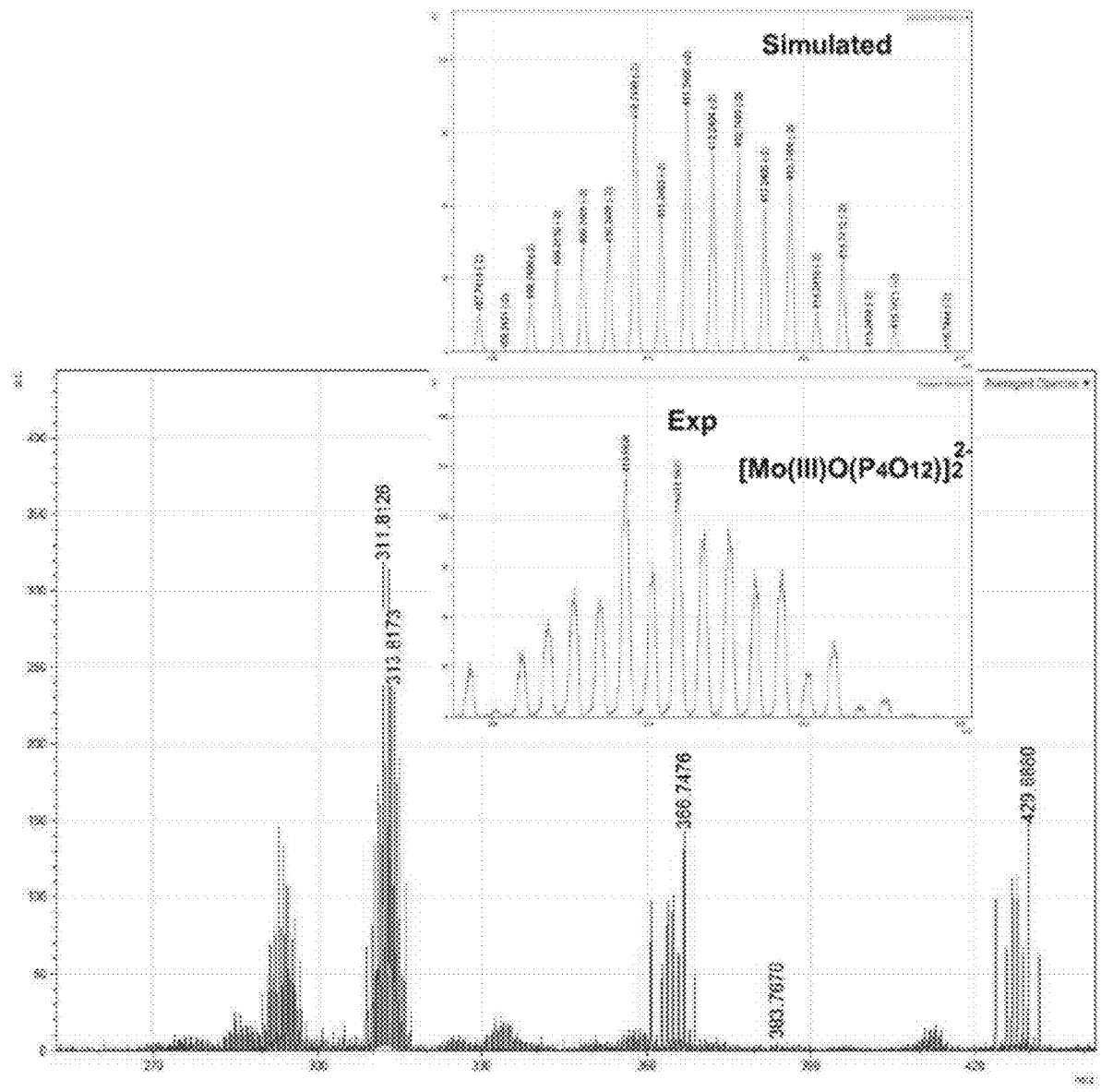
FIG. 55 shows ESI-MS(−) spectrum of $[PPN]_4[Mo_2(P_4O_{12})_2]$ ($[PPN]_4[9]$).
Figure 56:
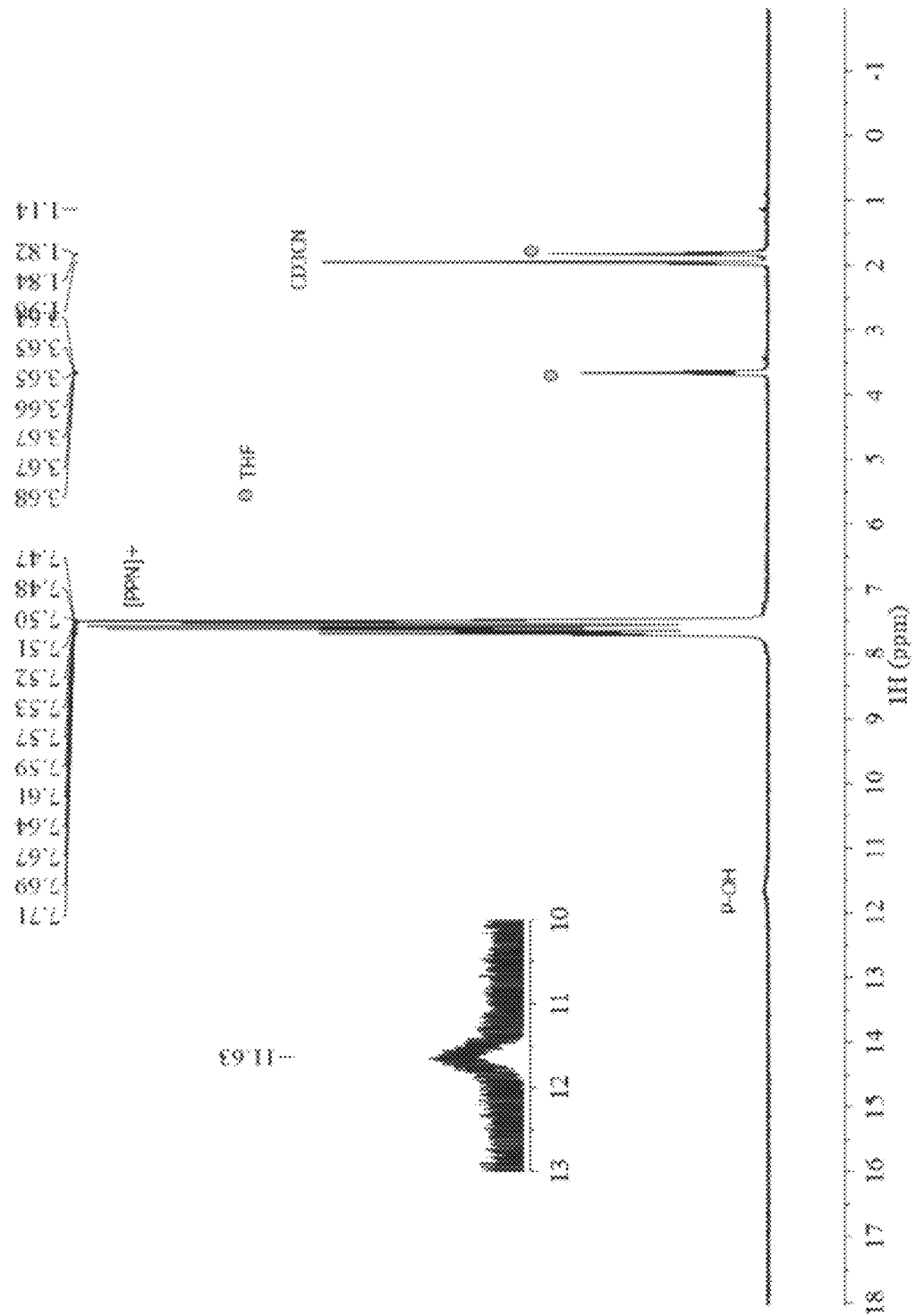
FIG. 56 shows $^1H$ NMR (400.1 MHz) of $[PPN]_2[P_3O_9H]$ ($[PPN]_2[10]$) recorded at 23° C. in $CD_3CN$.
Figure 57:
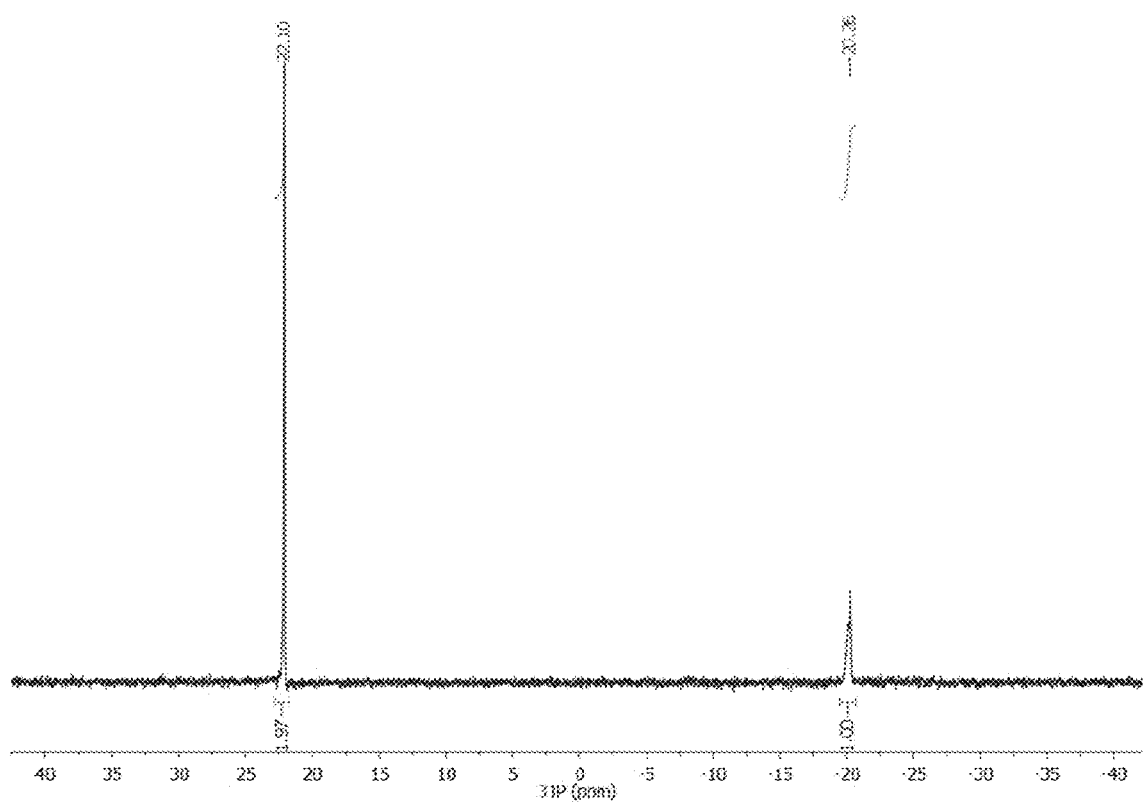
FIG. 57 shows $^{31}P\{^1H\}$ NMR (122.0 MHz) of $[PPN]_2[P_3O_9H]$ ($[PPN]_2[10]$) recorded at 23° C. in $CD_3CN$
Figure 58:
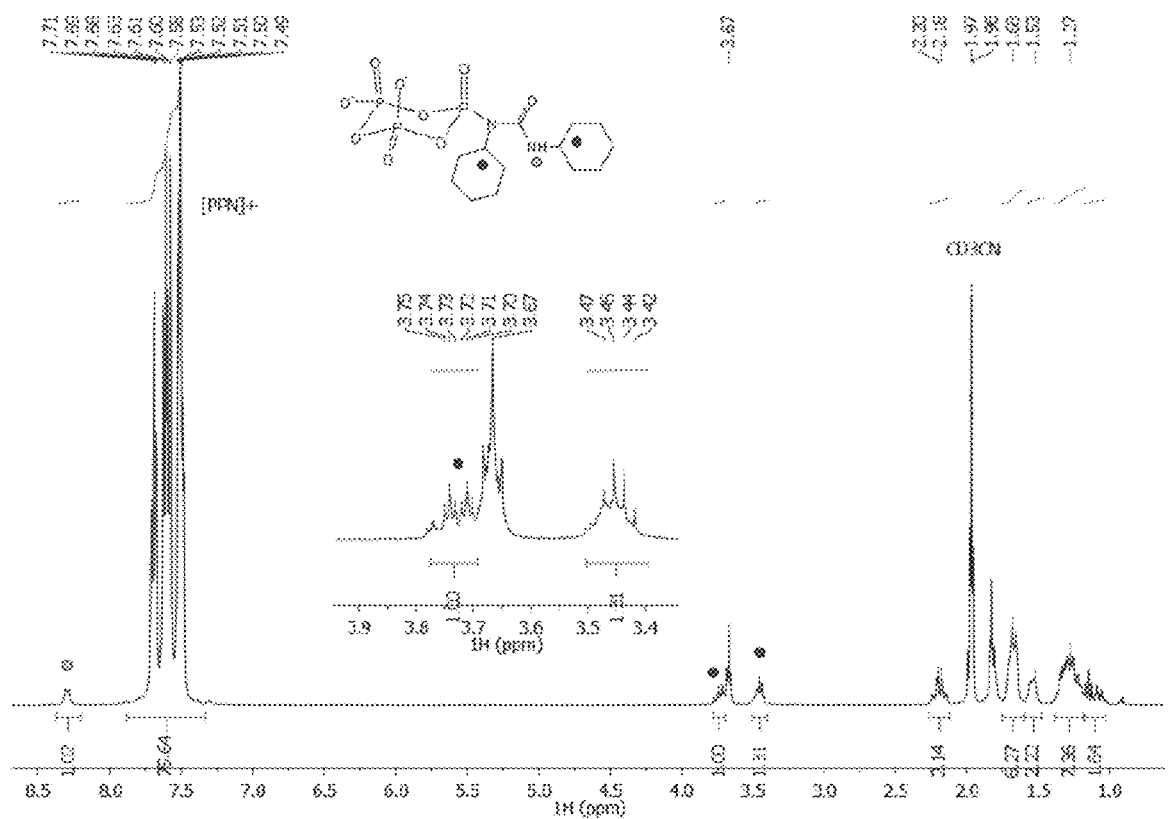
FIG. 58 shows 1H NMR (400.1 MHz) of [PPN]$_2$[P$_3$O$_8$N(Cy)CONH(Cy)]([PPN]$_2$[11]) recorded at 23° C. in CD$_3$CN.
Figure 59:
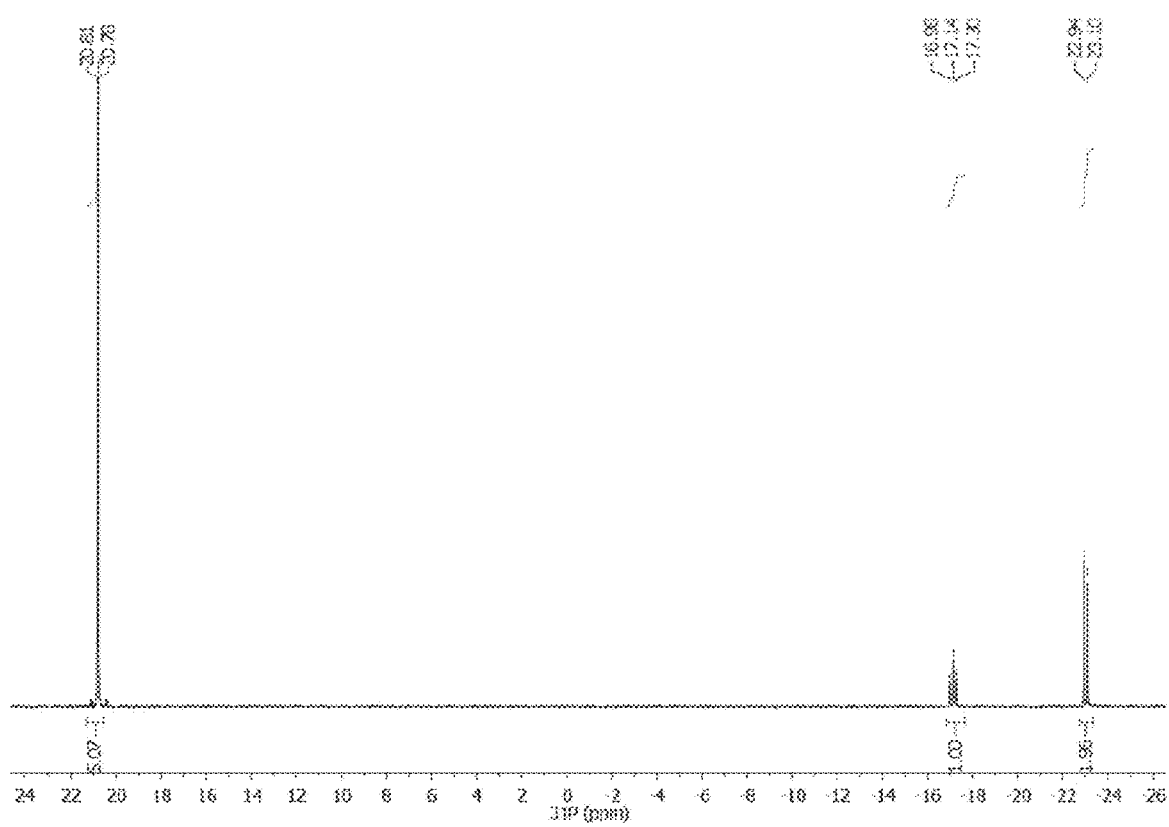
FIG. 59 shows $^{31}$P{$^1$H} NMR (161.9 MHz) of [PPN]$_2$[P$_3$O$_8$N(Cy)CONH(Cy)]([PPN]$_2$[11]) recorded at 23° C. in CD$_3$CN.
Figure 60:
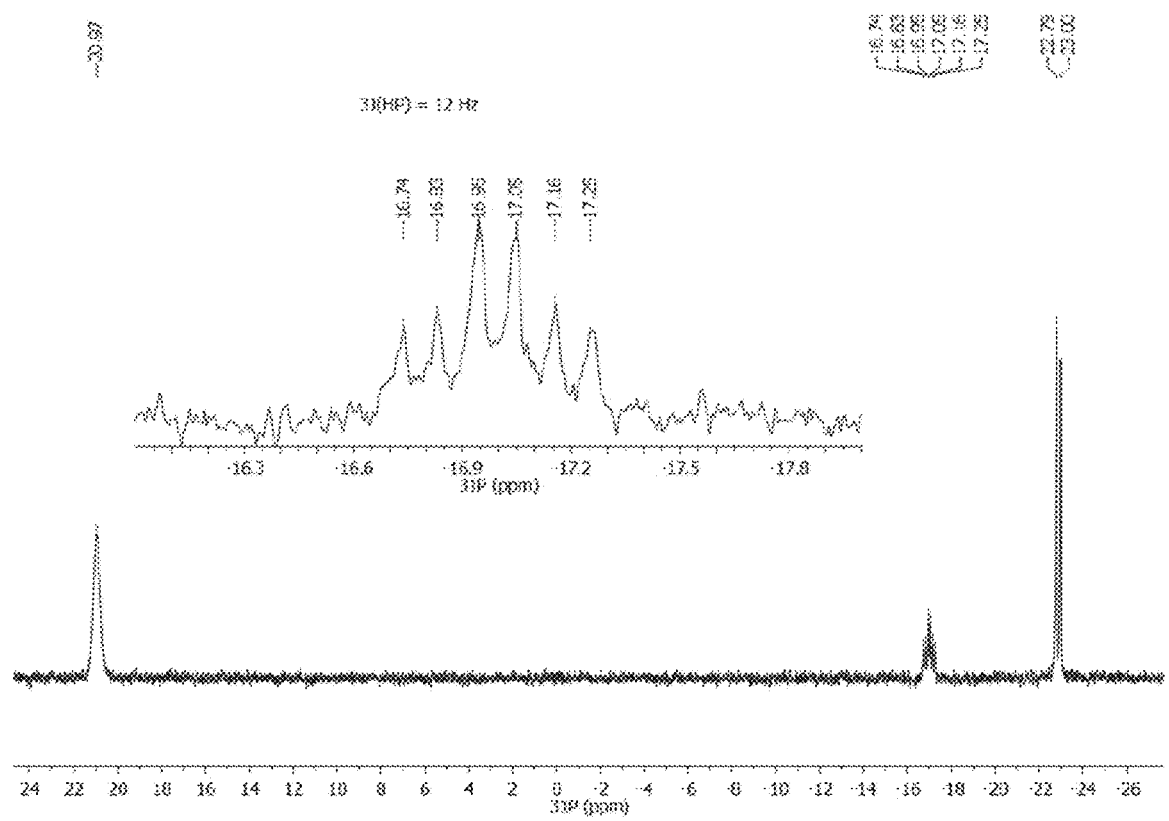
FIG. 60 shows $^{31}$P NMR (122 MHz) of [PPN]$_2$[P$_3$O$_8$N(Cy)CONH(Cy)]([PPN]$_2$[11]) recorded at 23° C. in CD$_3$CN.
Figure 61:
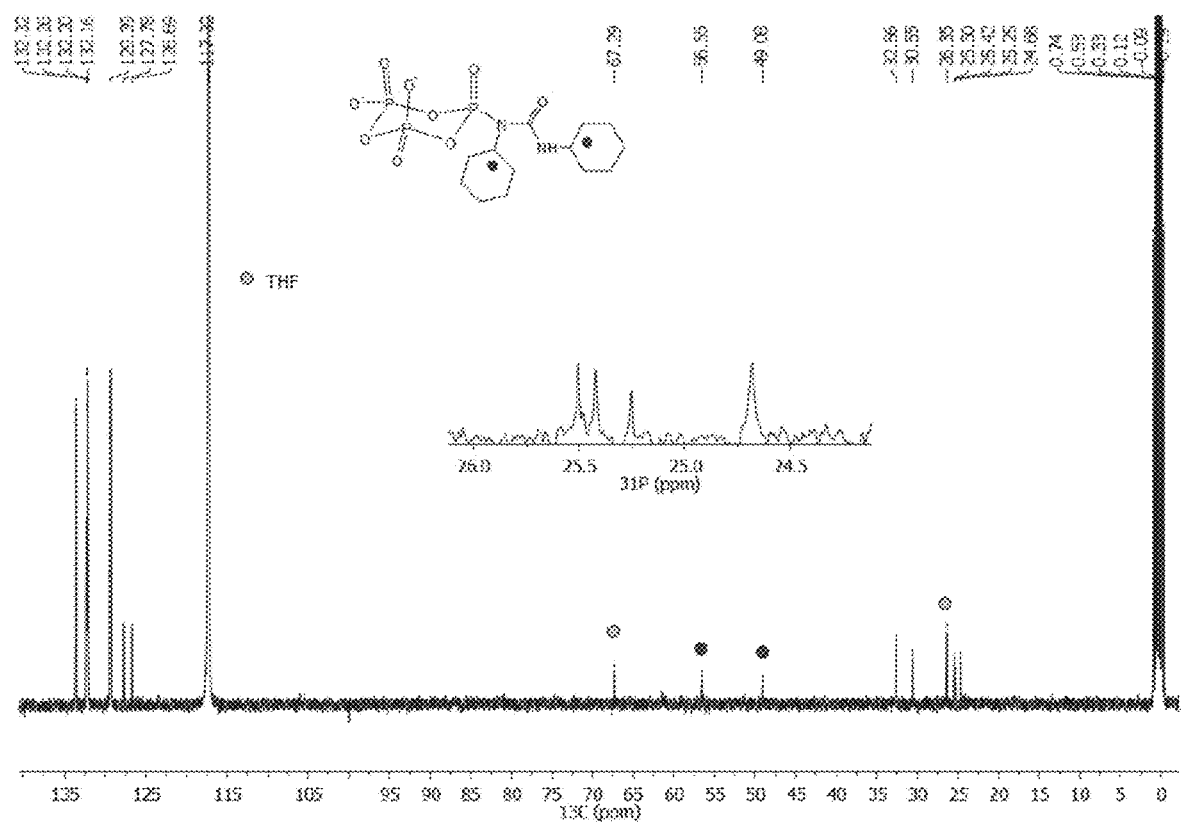
FIG. 61 shows $^{13}$C NMR (100 MHz) of [PPN]$_2$[P$_3$O$_8$N(Cy)CONH(Cy)]([PPN]$_2$[11]) recorded at 23° C. in CD$_3$CN.
Figure 62:
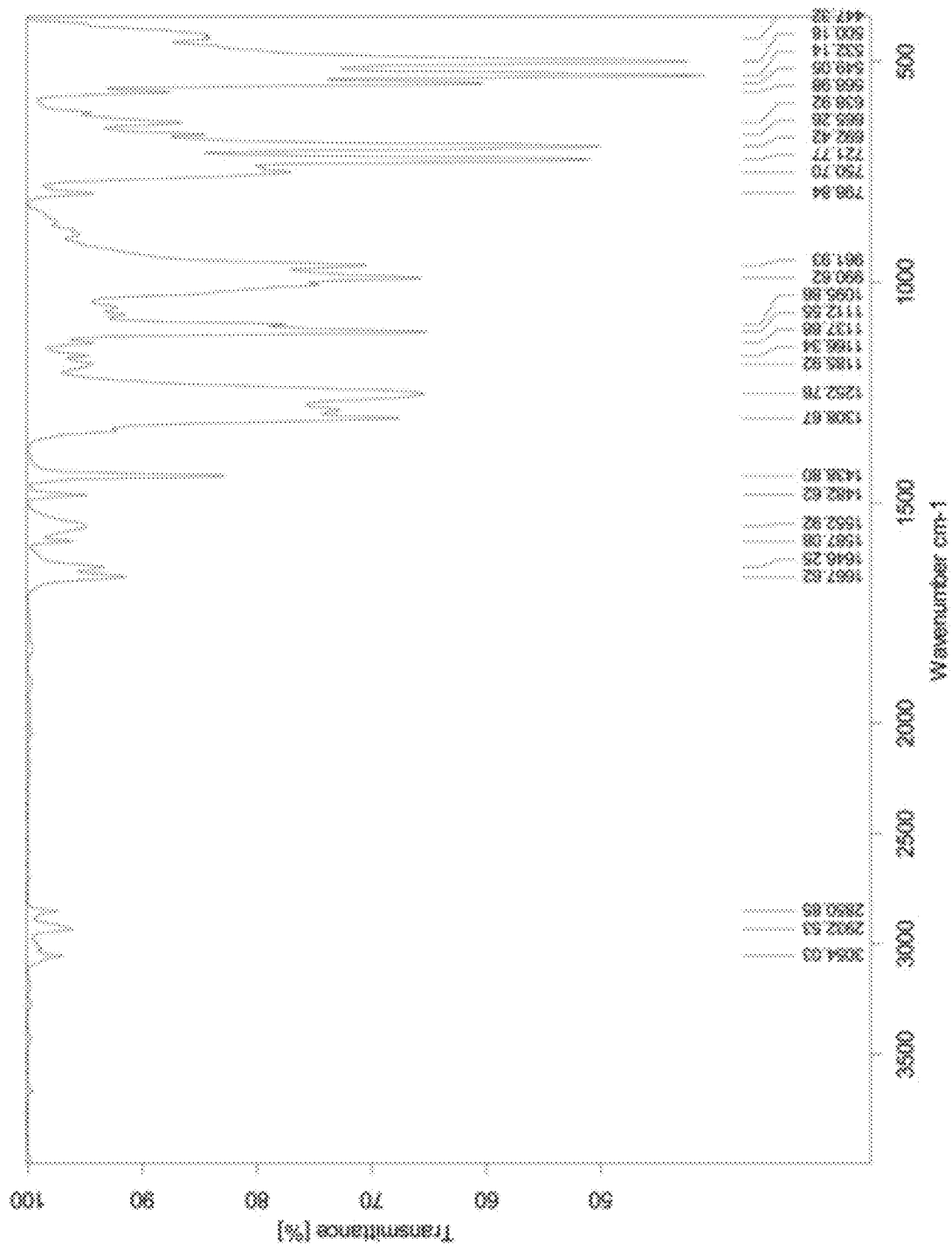
FIG. 62 shows ATR-IR spectrum of solid [PPN]$_2$[P$_3$O$_8$N(Cy)CONH(Cy)]([PPN]$_2$[11])
Figure 63:
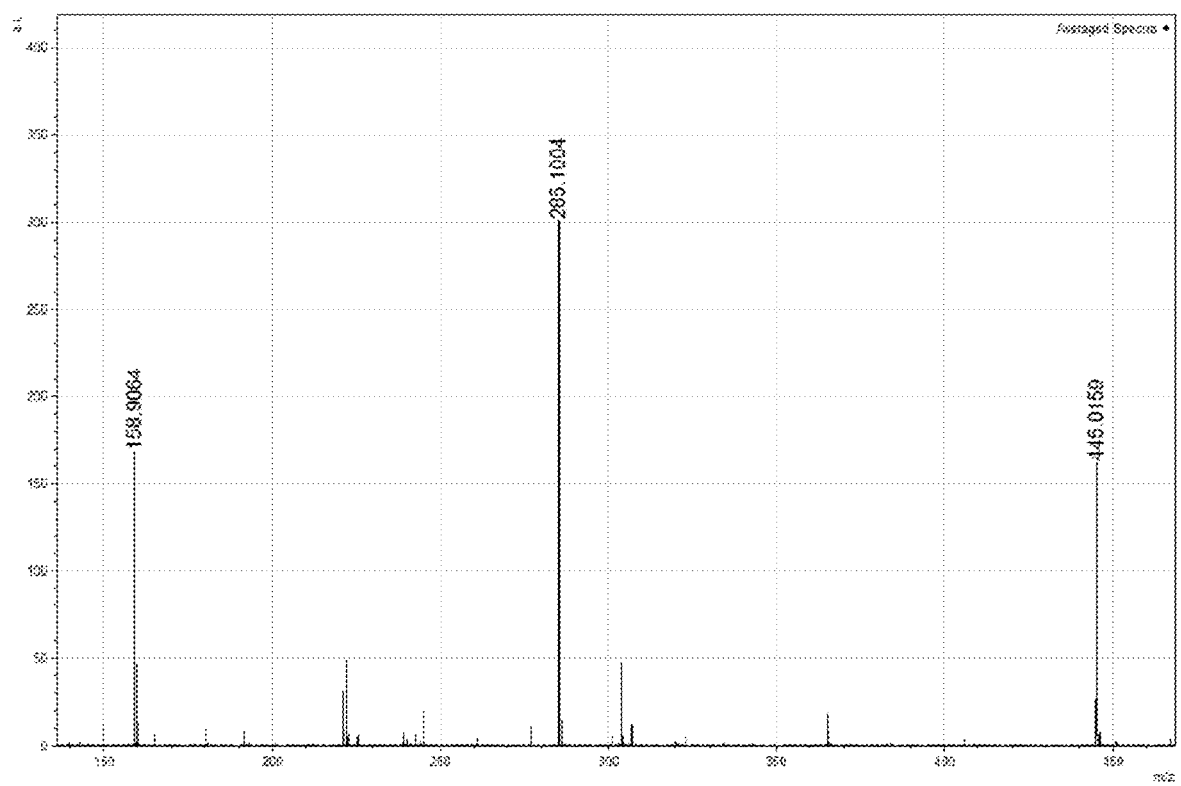
FIG. 63 shows ESI-MS(−) spectrum of [PPN]$_2$[P$_3$O$_8$N(Cy)CONH(Cy)]([PPN]$_2$[11]).
Figure 64:
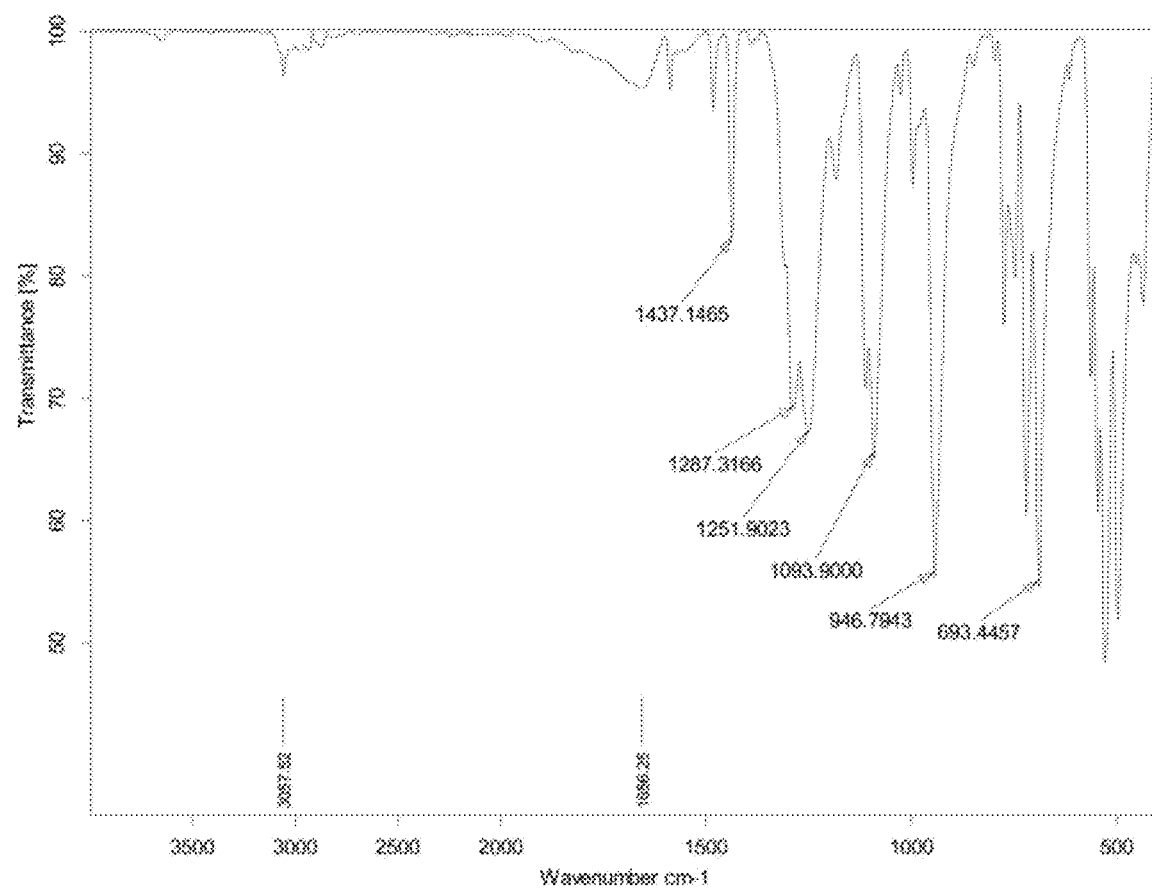
FIG. 64 shows ATR-IR spectrum of solid [PPN]$_4$[Fe(P$_3$O$_9$)$_2$] ([PPN]$_4$[12]).
Figure 65:
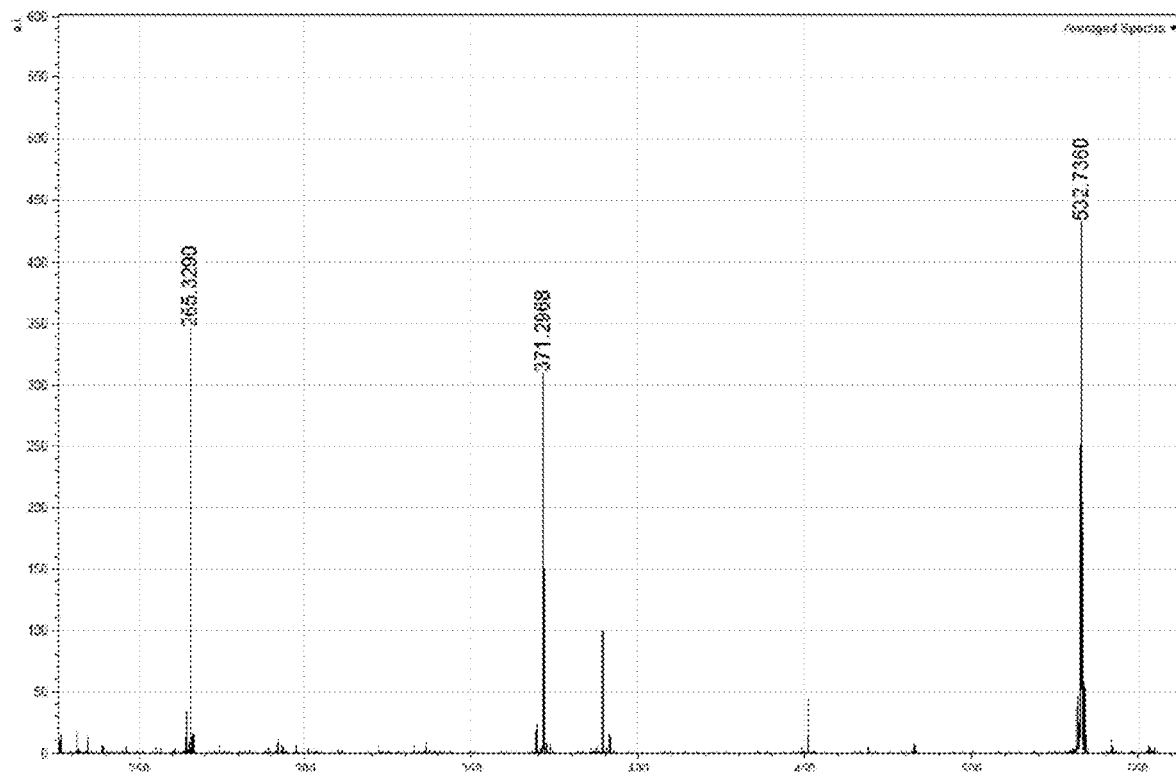
FIG. 65 shows ESI-MS(−) spectrum of [PPN]$_4$[Fe(P$_3$O$_9$)$_2$] ([PPN]$_4$[12])
Figure 66:
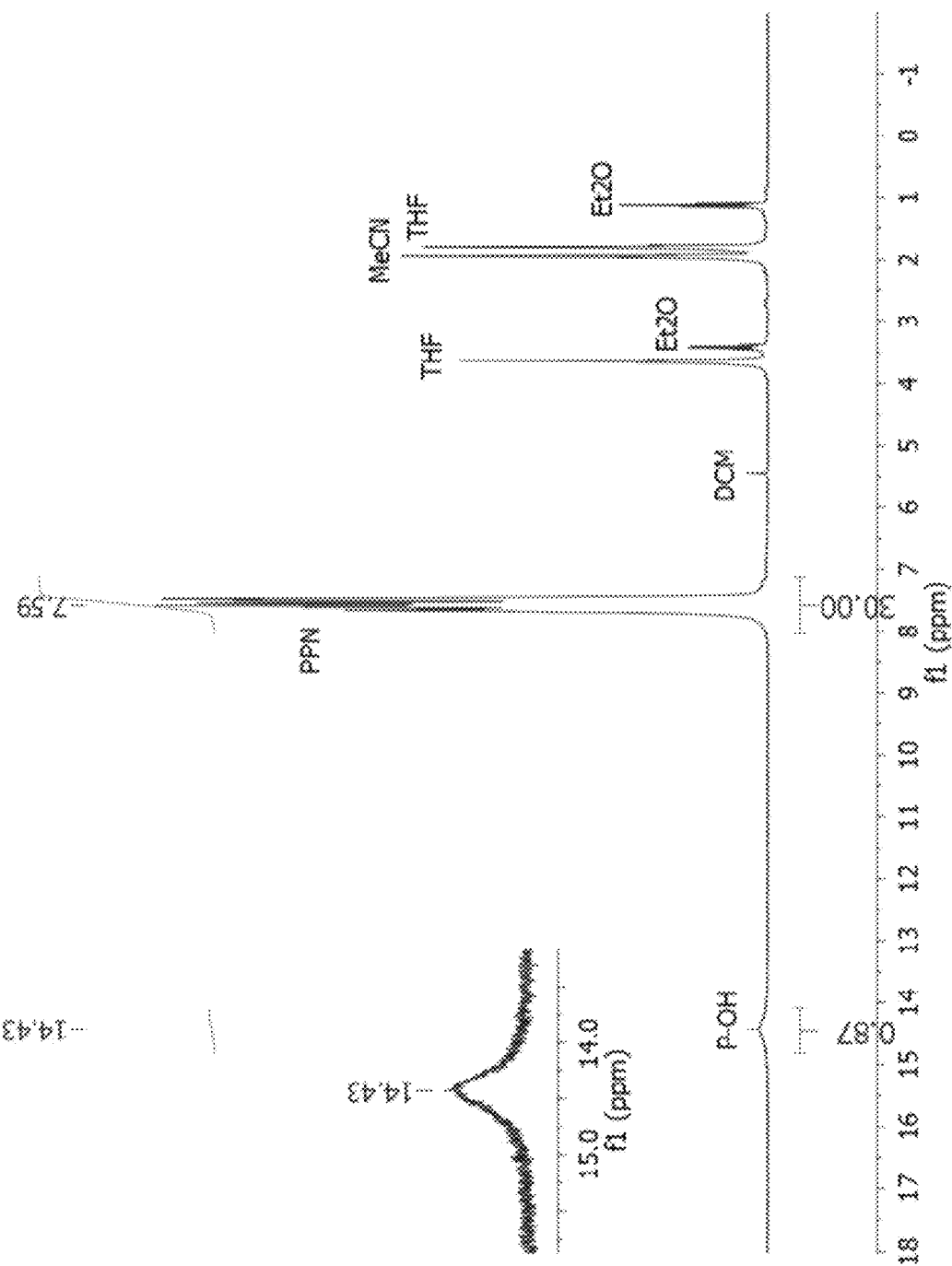
FIG. 66 shows $^1$H NMR (300.1 MHz) of [PPN][P$_3$O$_9$H$_2$] ([PPN][13]) recorded at 23° C. in CD$_3$CN.
Figure 67:
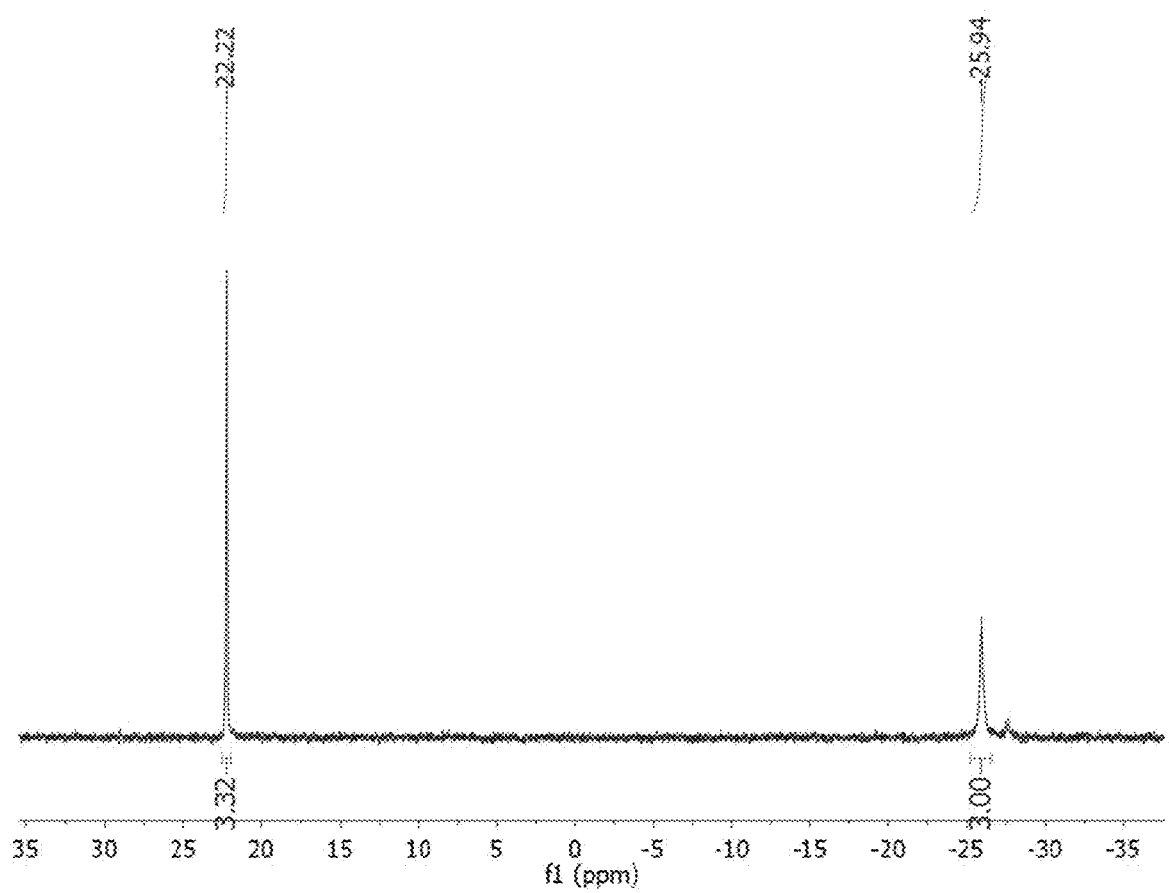
FIG. 67 shows $^{31}$P{$^1$H} NMR (122.0 MHz) of [PPN][P$_3$O$_9$H$_2$] ([PPN][13]) recorded at 23° C. in CD$_3$CN.
Figure 68:
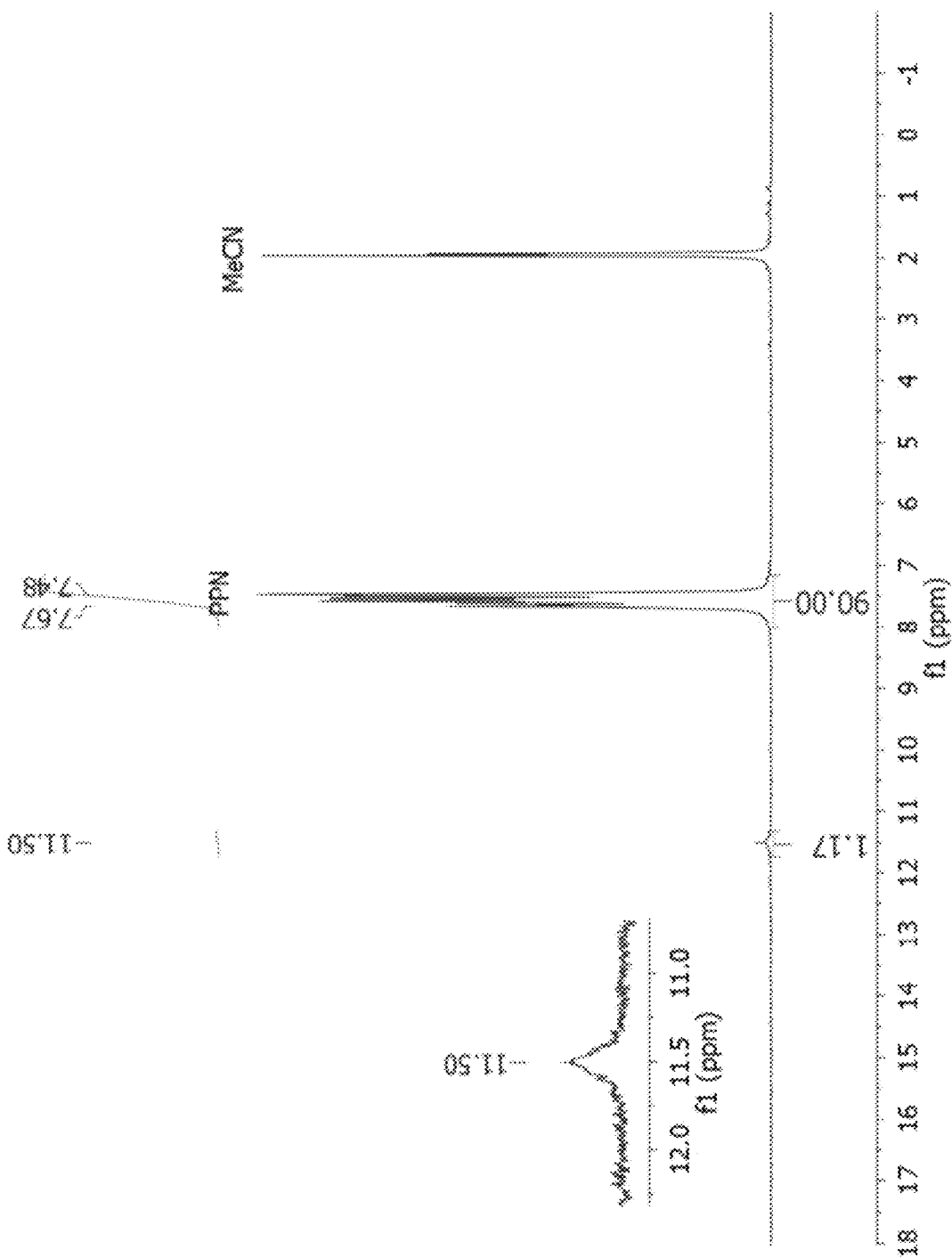
FIG. 68 shows 1H NMR (300.1 MHz) of [PPN]$_3$[P$_4$O$_{12}$H] ([PPN]$_3$[14]) recorded at 23° C. in CD$_3$CN.
Figure 69:
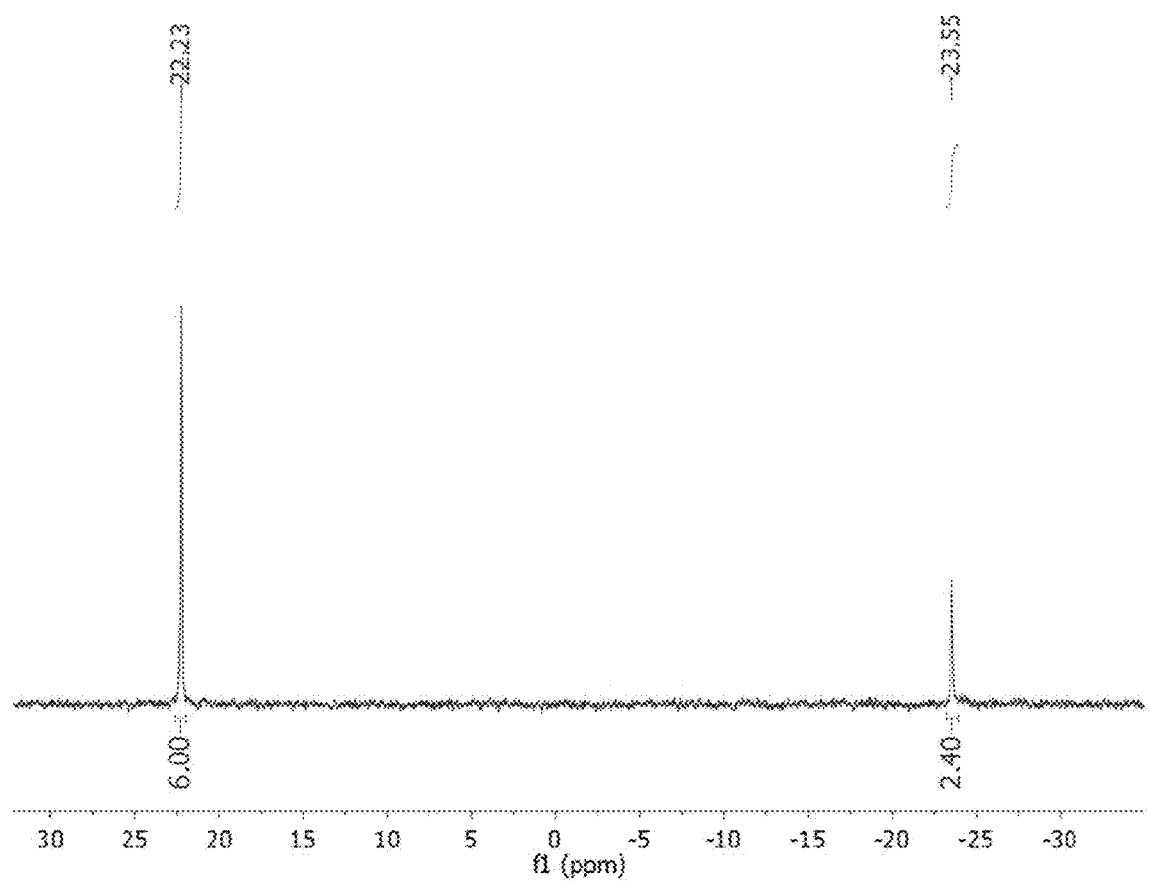
FIG. 69 shows $^{31}$P{$^1$H} NMR (122.0 MHz) of [PPN]$_3$[P$_4$O$_{12}$H] ([PPN]$_3$[14]) recorded at 23° C. in CD$_3$CN.
Figure 70:
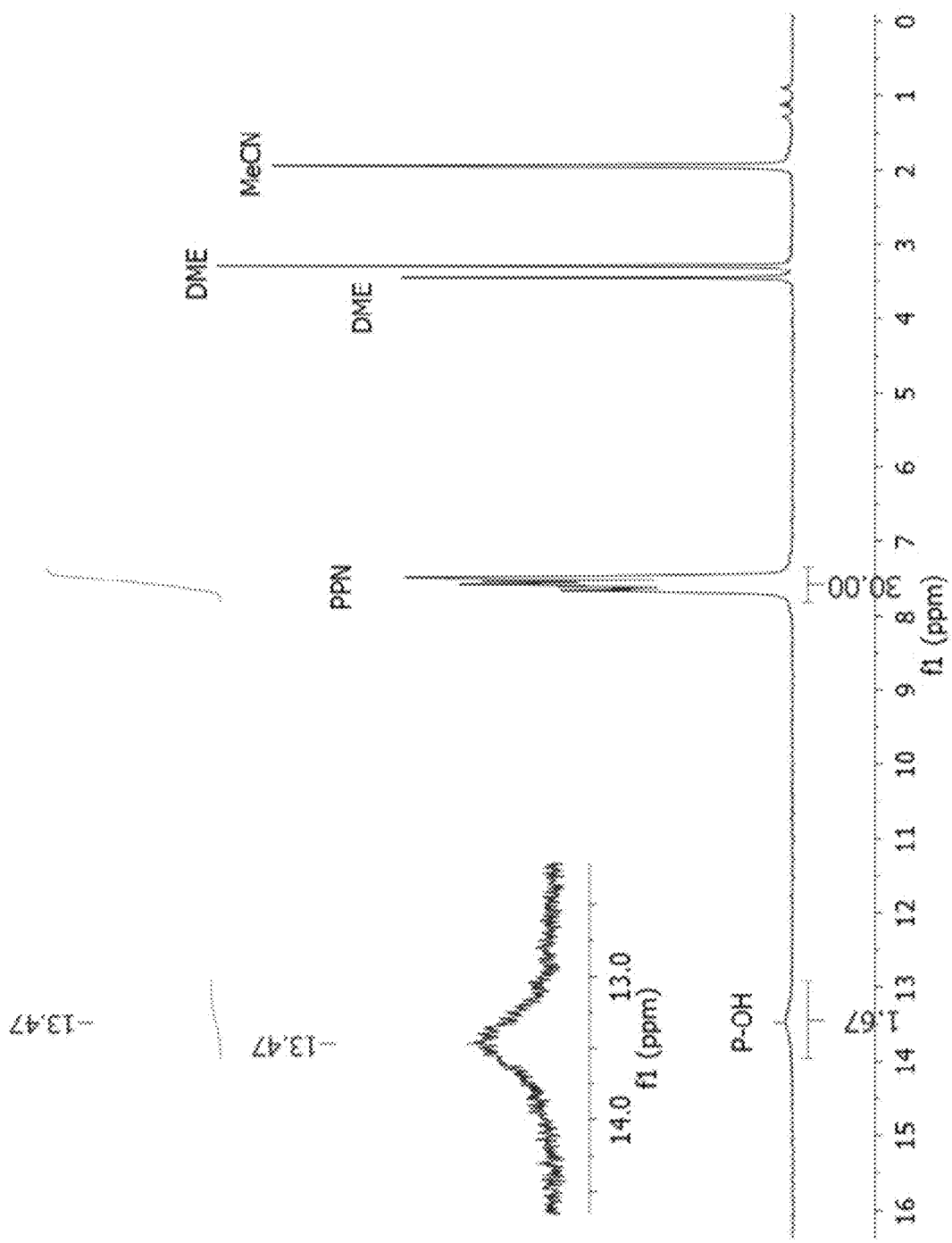
FIG. 70 shows 1H NMR (300.1 MHz) of [PPN][P$_4$O$_{12}$H$_3$] ([PPN][15]) recorded at 23° C. in CD$_3$CN.
Figure 71:
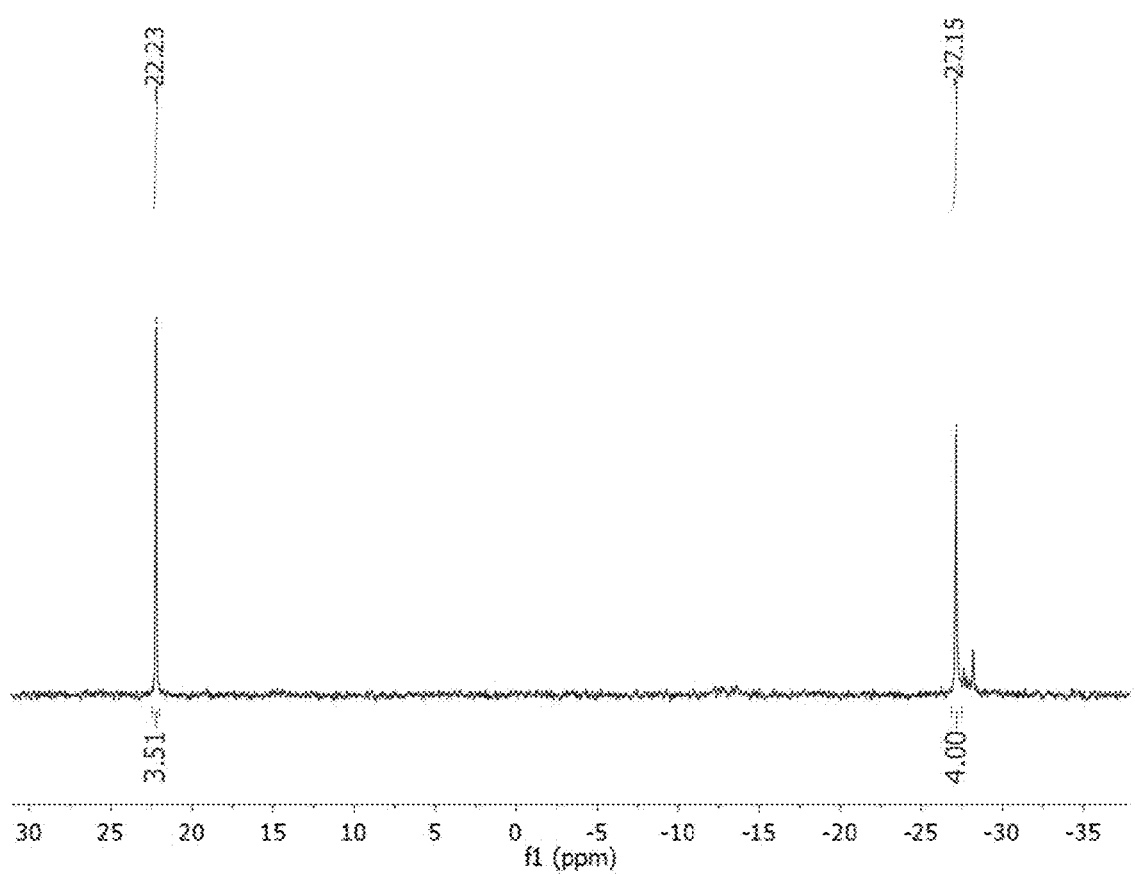
FIG. 71 shows $^{31}$P{$^1$H} NMR (122.0 MHz) of [PPN][P$_4$O$_{12}$H$_3$] ([PPN][15]) recorded at 23° C. in CD$_3$CN.
Figure 72:
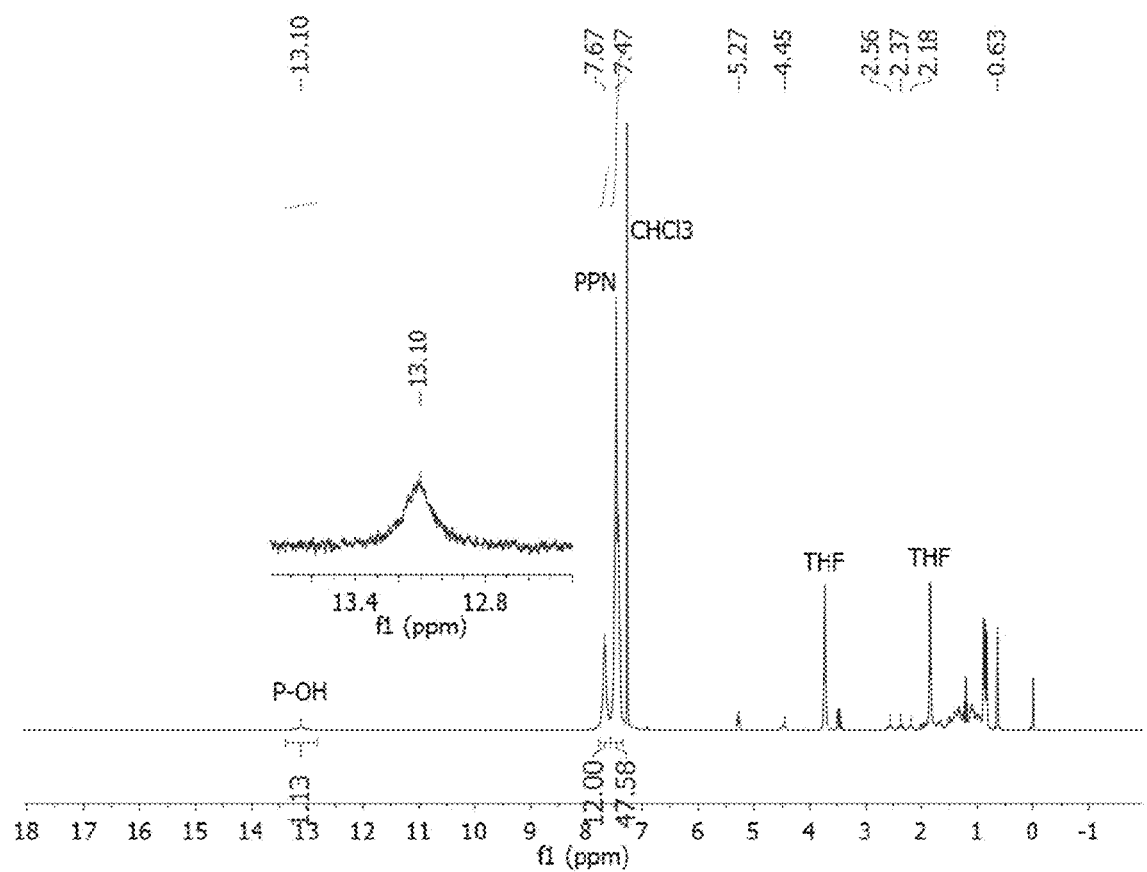
FIG. 72 shows $^1$H NMR (300.1 MHz) of [PPN]$_2$[cholesterol-P$_4$O$_{12}$H]([PPN]$_2$[16]) recorded at 23° C. in CDCl$_3$.
Figure 73:
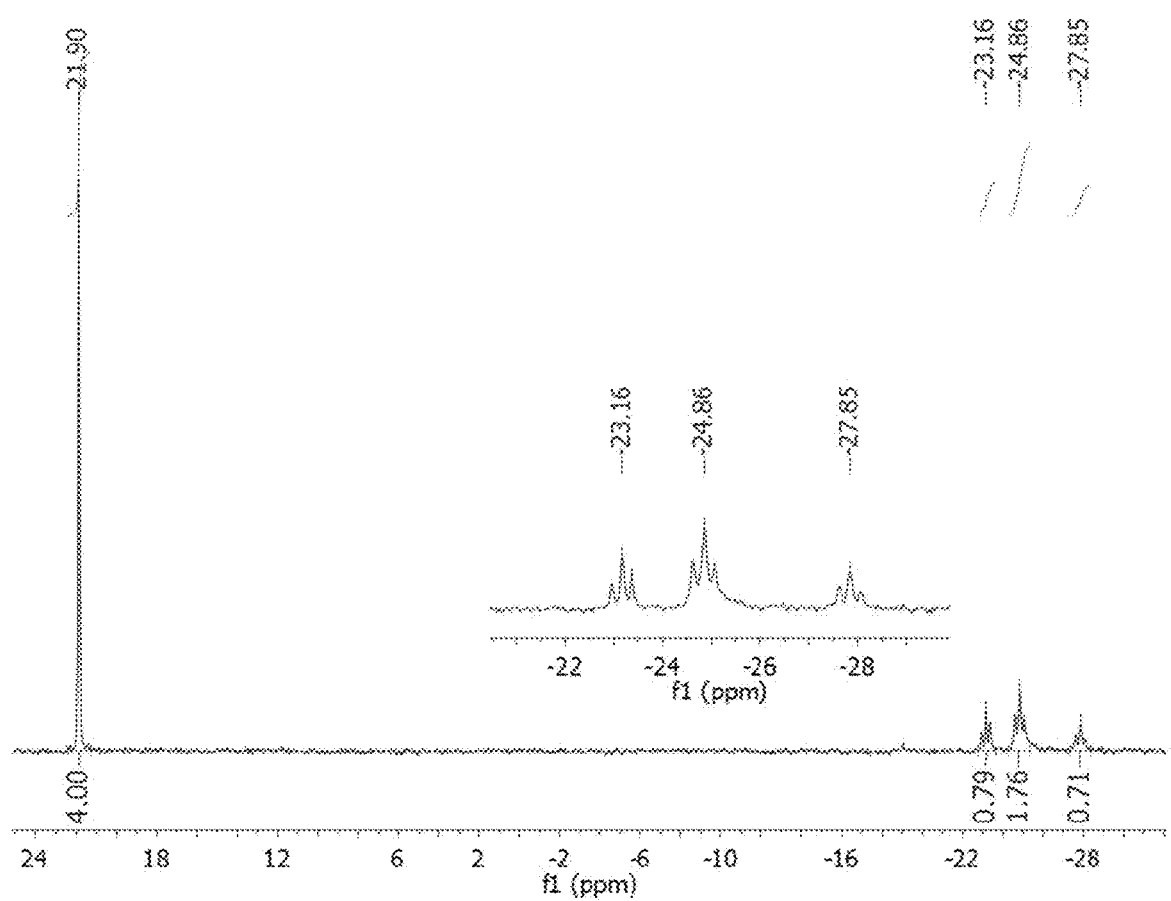
FIG. 73 shows $^{31}$P{$^1$H} NMR (122.0 MHz) of [PPN]$_2$[cholesterol-P$_4$O$_{12}$H]([PPN]$_2$[16]) recorded at 23° C. in CDCl$_3$.
Figure 74:
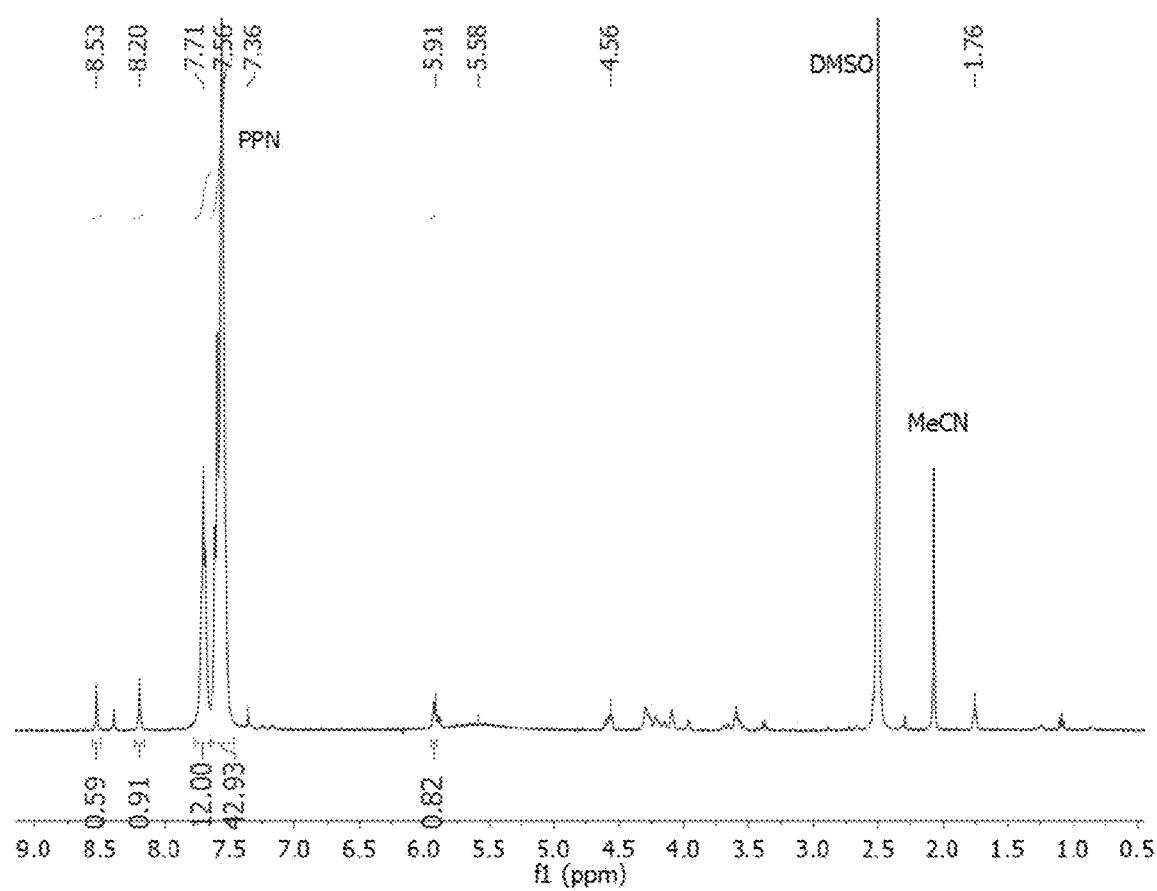
FIG. 74 shows $^1$H NMR (400.1 MHz) of [PPN]$_2$[adenosine-P$_4$O$_{12}$H] ([PPN]$_2$[17]) recorded at 23° C. in DMSO-d$_6$.
Figure 75:
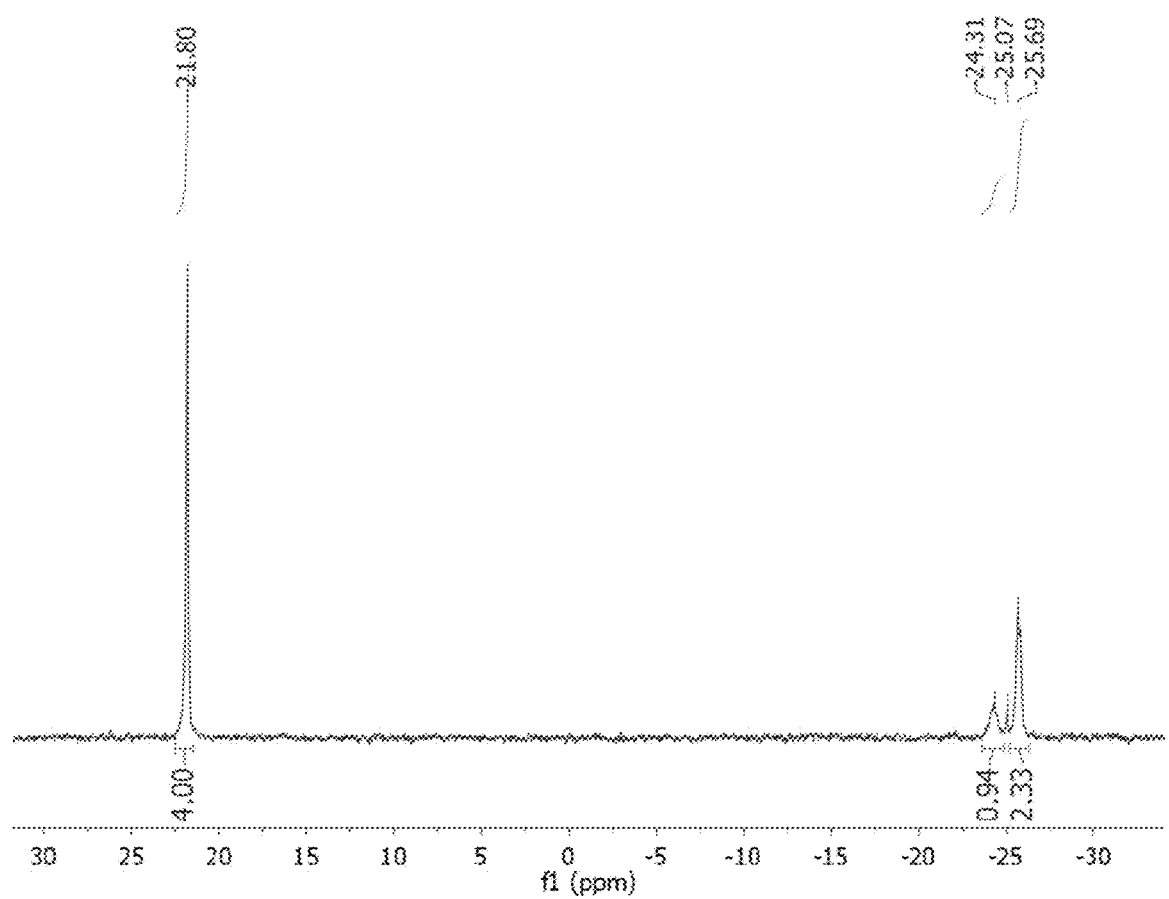
FIG. 75 shows $^{31}$P{$^1$H} NMR (122.0 MHz) of [PPN]$_2$[adenosine-P$_4$O$_{12}$H]([PPN]$_2$[17]) recorded at 23° C. in DMSO-d$_6$.
Figure 76:
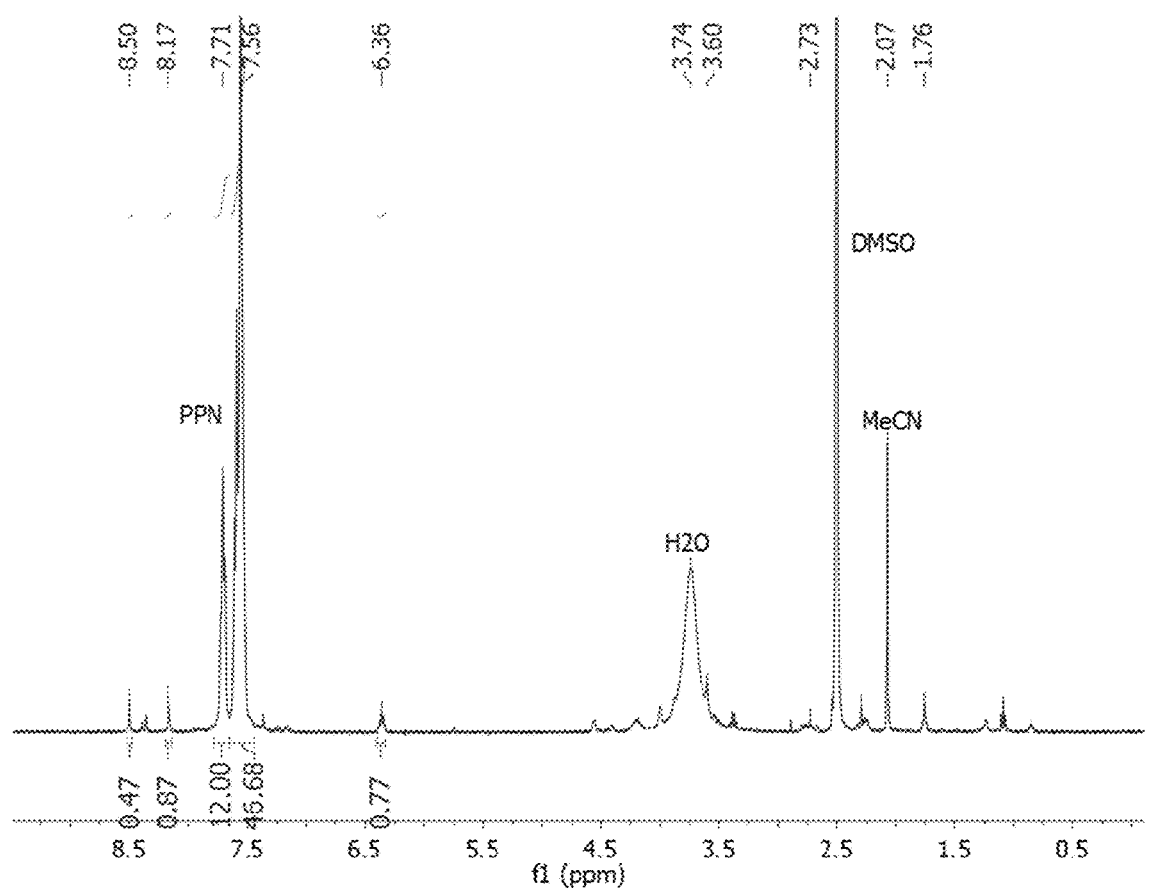
FIG. 76 shows $^1$H NMR (400.1 MHz) of [PPN]$_2$[2'-deoxyadenosine-P$_4$O$_{12}$H]([PPN]$_2$[18]) recorded at 23° C. in DMSO-d$_6$.
Figure 77:
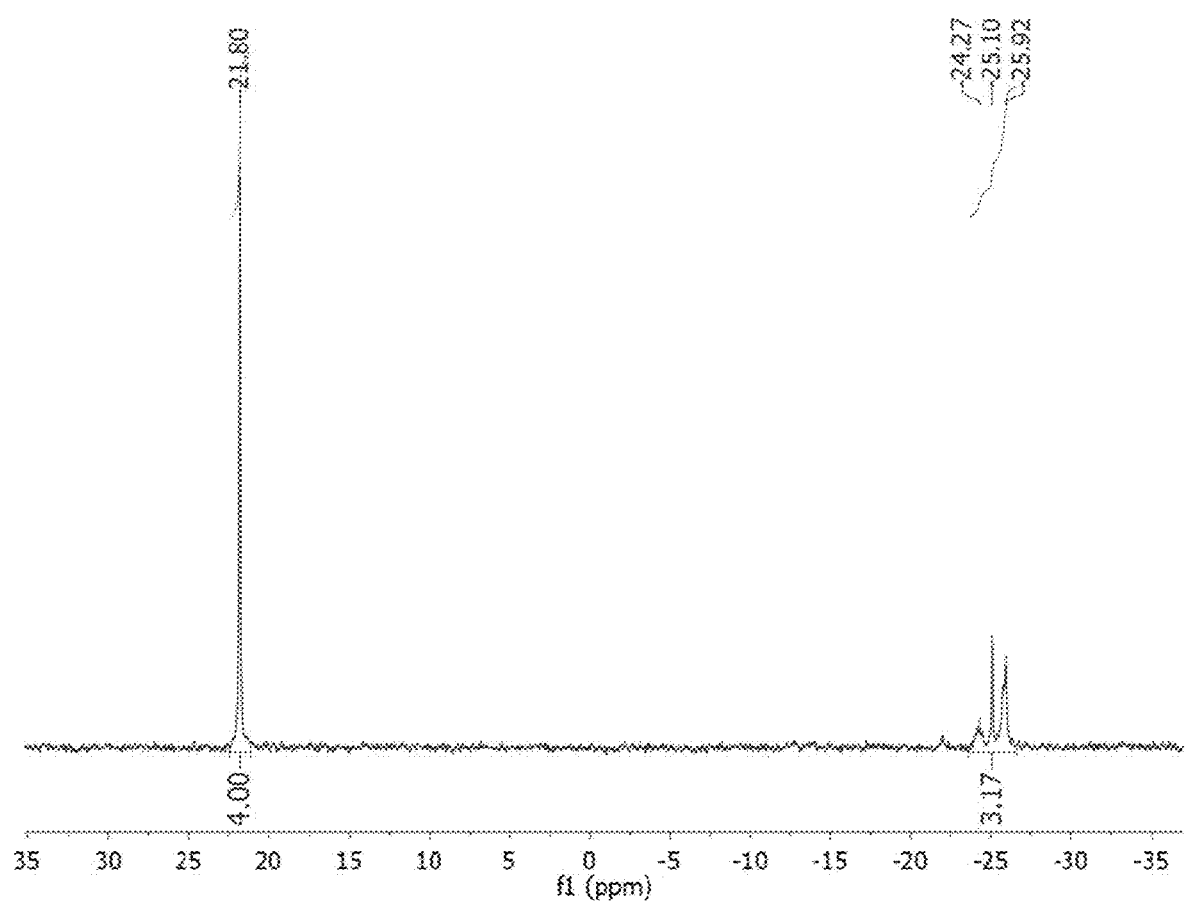
FIG. 77 shows $^{31}$P{$^1$H} NMR (122.0 MHz) of [PPN]$_2$[2'-deoxyadenosine-P$_4$O$_{12}$H] ([PPN]$_2$[18]) recorded at 23° C. in DMSO-d$_6$.
Figure 78:
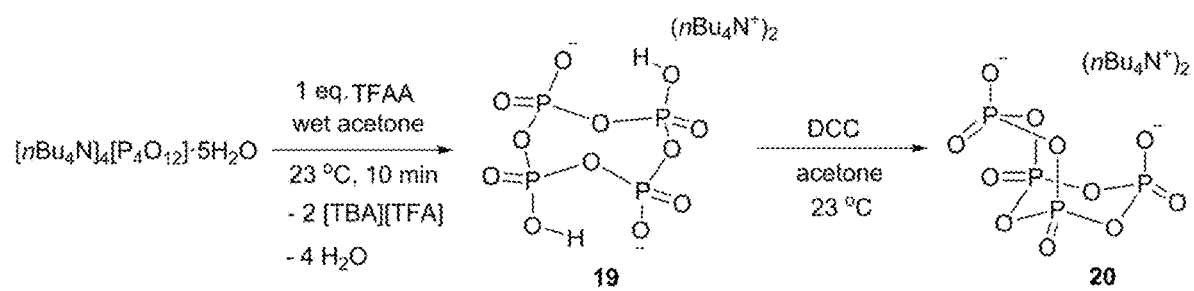
FIG. 78 shows the synthesis of TBA salt of dihydrogen tetrametaphosphate [TBA]$_2$[P$_4$O$_{12}$H$_2$] ([TBA]$_2$[19]) and tetrametaphosphate anhydride [TBA]$_2$[P$_4$O$_{11}$]([TBA]$_2$[20])
Figure 79:
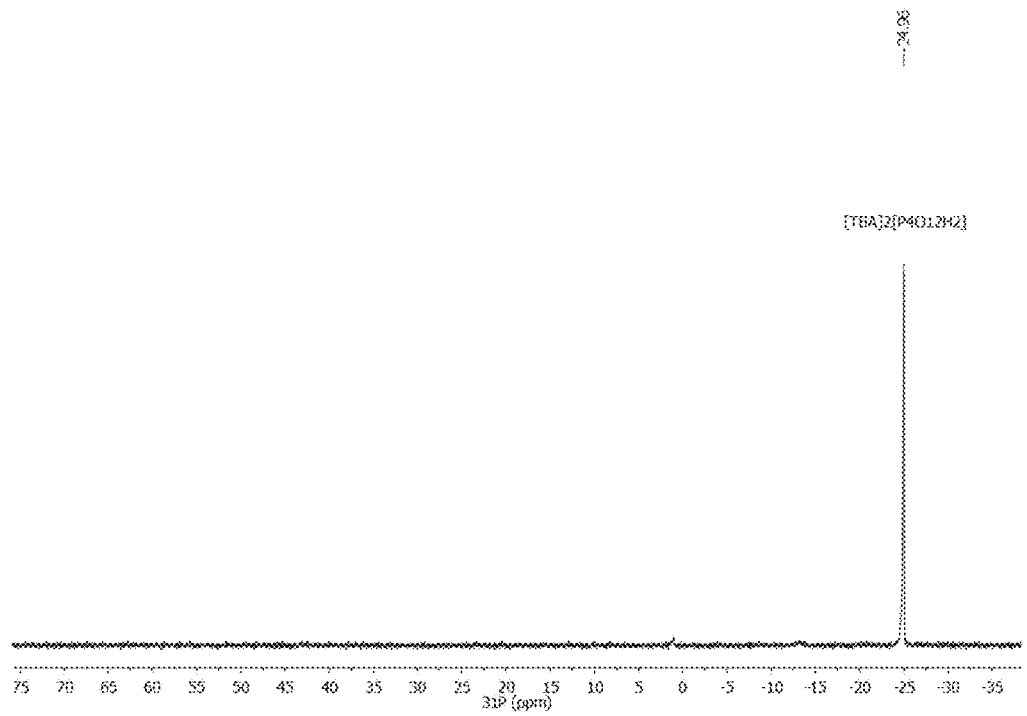
FIG. 79 shows $^{31}$P{1H} NMR (122.0 MHz) of [TBA]$_2$[P$_4$O$_{12}$H$_2$] ([TBA]$_2$[19]) recorded at 23° C. in Me$_2$CO
Figure 80:
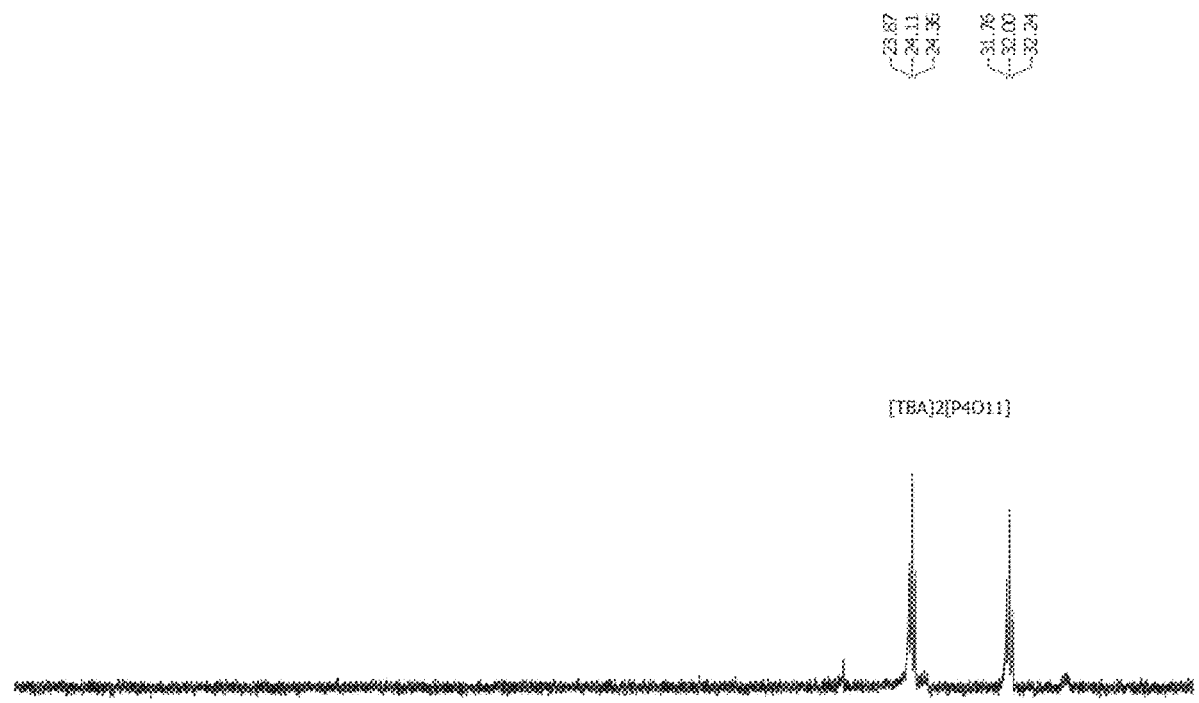
FIG. 80 shows $^{31}$P{1H} NMR (122.0 MHz) of [TBA]$_2$[P$_4$O$_{11}$] ([TBA]$_2$[20]) recorded at 23° C. in Me$_2$CO

The solid-state structure of $[PPN]_2[P_3O_9H]$ ($[PPN]_2[10]$) was established using single-crystal X-ray diffraction, as depicted in FIG. 37. The hydrogen atom was placed at calculated positions rather than located and refined. Evidently intramolecular hydrogen bond between the proton and the neighboring P—O⁻ H-bond acceptor was observed showing a short O11 . . . O21 distance of 2.611 Å. The P—OH bond length of 1.5639(18) Å is significantly longer than other external P—O distances.

The reactivity of the monohydrogen trimetaphosphate $[PPN]_2[P_3O_9H]$ was explored. Treatment of $[PPN]_2[P_3O_9H]$ with excess of DCC in acetonitrile afforded the condensation product N-trimetaphosphorylurea ($[PPN]_2[11]$), which was isolated in 80% yield and fully characterized. Moreover, the protonolysis strategy was also found to be applicable to the monoacid $[PPN]_2[P_3O_9H]$. When $[PPN]_2[P_3O_9H]$ was treated with half equivalent of $Fe(acac)_2$ a paramagentic iron(II) cyclic phosphate was formed, as indicated by the silent cyclic phosphate region in the $^{31}P\{^1H\}$ NMR spectrum. After workup the compound $[PPN]_4[Fe(P_3O_9)_2]$ ($[PPN]_4[12]$) was isolated in 65% yield and fully characterized. Single crystals suitable for an X-ray diffraction study were obtained from a mixture of acetonitrile and diethyl ether.

When $[PPN]_3[P_3O_9]\cdot H_2O$ was treated with 1 equivalent of $(CF_3SO_2)_2O$ in acetonitrile, the formation of dihydrogen trimetaphosphate $[PPN][P_3O_9H_2]$ ($[PPN][13]$) was observed. The $^{31}P\{^1H\}$ NMR spectrum revealed a broad singlet at −25.7 ppm, which is high-field shifted comparing to that of the monohydrogen trimetaphosphate $[PPN]_2[P_3O_9H]$ ($[PPN]_2[10]$).

Similar to trimetaphosphate, tetrametaphosphate was found to exist in other protonation states apart from dihydrogen tetrametaphosphate. Treatment of $[PPN]_2[P_4O_{12}H_2]$ with $[PPN]_4[(P_4O_{12})]\cdot 5H_2O$ led to a clean formation of monohydrogen tetrametaphosphate $[PPN]_3[P_4O_{12}H]$ ($[PPN]_3[14]$) as the only product. The strong acidity of $[PPN]_2[P_4O_{12}H_2]$ led to complete formation of $[PPN]_3[P_4O_{12}H]$. The acid equilibrium was not shifted back to $[PPN]_2[P_4O_{12}H_2]$ and $[PPN]_4[P_4O_{12}]$ when N,N-dicyclohexylurea was added to dehydrate $[PPN]_2[P_4O_{12}H_2]$ to $[PPN]_2[P_4O_{11}]$. The presence of acidic P—OH groups is confirmed by a broad singlet at 11.50 ppm in the 1H NMR spectrum in $CD_3CN$ at 23° C. The $^{31}P\{^1H\}$ NMR spectrum features a singlet at −23.55 ppm which appears at the chemical shift between the signal of $[PPN]_4[(P_4O_{12})]\cdot 5H_2O$ and that of $[PPN]_2[P_4O_{12}H_2]$.

Protonation of $[PPN]_2[P_4O_{12}H_2]$ by $CF_3SO_3H$ afforded trihydrogen tetrametaphosphate $[PPN][P_4O_{12}H_3]$ ($[PPN][15]$). Similar to $[PPN][P_3O_9H_2]$, $[PPN][P_4O_{12}H_3]$ could not be prepared from $CF_3COOH$ because of the stronger acidity of $[PPN][P_4O_{12}H_3]$ than that of $(CF_3CO)_2O$. When $[PPN]_4[(P_4O_{12})]\cdot 5H_2O$ was treated with 1.5 equivalents of $(CF_3SO_2)_2O$, $[PPN][P_4O_{12}H_3]$ was generated but was deprotonated by stoichiometric amount of water from $[PPN]_4[(P_4O_{12})]\cdot 5H_2O$ starting material to yield $[PPN]_2[P_4O_{12}H_2]$ during isolation. The isolation of $[PPN][P_4O_{12}H_3]$ was achieved when $[PPN]_2[P_4O_{12}H_2]$ was treated with $CF_3SO_3H$, or when one equivalent of $[PPN]_4[(P_4O_{12})]\cdot 5H_2O$ was treated with 5 equivalents of $(CF_3SO_2)_2O$ to completely consume water in the starting material (Eqn. 1). The acidic protons in P—OH groups of $[PPN][P_4O_{12}H_3]$ appears at 13.47 ppm in $^1H$ NMR spectrum recorded in $CD_3CN$ at 23° C. The signal of tetrametaphosphate appears at −27.15 ppm in $^{31}P\{^1H\}$ NMR spectrum, featuring the most upfield-shifted $^{31}P$ NMR signal of tetrametaphosphate.

$$[PPN]_4[P_4O_{12}]\cdot 5H_2O + 7[PPN]_2[P_4O_{12}H_2] + 5(CF_3SO_2)_2O \rightarrow 8[PPN][P_4O_{12}H_3] + 10[PPN][CF_3SO_3] \quad (1)$$

The methanolysis reaction of $[PPN]_2[P_4O_{11}]$ which afforded $[PPN]_2[P_4O_{10}(OH)(OMe)]$ as the product prompted us to further investigate the reactivity of $[PPN]_2[P_4O_{11}]$ toward other alcohols. In particular, $[PPN]_2[P_4O_{11}]$ could potentially be used to phosphorylate alcohols of biological importance. Phosphorylation of biological molecules such as nucleosides, amino acids, as well as steroids, would present great applications. Treatment of $[PPN]_2[P_4O_{11}]$ with cholesterol under anhydrous condition at room temperature led to the formation of $[PPN]_2[\text{cholesterol-}P_4O_{12}H]$ ($[PPN]_2[16]$) in 6 days. The alcoholysis reaction was confirmed by 3 signals in $^{31}P\{^1H\}$ NMR spectrum as a triplet at −23.16 ppm, a double of doublet at −24.86 ppm, and a triplet at −27.85 ppm. The $^{31}P$ NMR pattern was similar to that of $[PPN]_2[P_4O_{10}(OH)(OMe)]$, thus leading us to conclude that cholesterol monohydrogen tetrametaphosphate was made. The presence of acidic P—OH group is evidenced by a broad singlet at 13.10 ppm in $^1H$ NMR spectrum recorded in $CDCl_3$. The alcoholysis of $[PPN]_2[P_4O_{11}]$ by cholesterol was significantly slower than methanolysis reaction, which could be explained by steric effect of cholesterol being a secondary alcohol as opposed to methanol.

Alcoholysis of $[PPN]_2[P_4O_{11}]$ by adenosine and 2'-deoxyadenosine led to the formation of $[PPN]_2[\text{adenosine-}P_4O_{12}H]$ ($[PPN]_2[17]$) and $[PPN]_2[\text{2'-deoxyadenosine-}P_4O_{12}H]$ ($[PPN]_2[18]$) respectively The reaction was complete within 1 day under anhydrous condition at room temperature. The reaction of $[PPN]_2[P_4O_{11}]$ with nucleosides yielded a mixture of 2 products, as indicated by 2 sets of signals in $^1H$ NMR corresponding to the nucleosides. Fluxional behavior of the tetrametaphosphate was observed in $^{31}P\{^1H\}$ NMR spectra, as evidenced by broad signals. Three signals of tetrametaphosphate moiety were observed at −24.31 (b), −25.07 (s), and −25.69 (b) ppm for $[PPN]_2[\text{adenosine-}P_4O_{12}H]$, and at −24.27 (b), −25.10 (s), and −25.92 (b) ppm for $[PPN]_2[\text{2'-deoxyadenosine-}P_4O_{12}H]$.

General Methods

Unless stated otherwise, all manipulations were performed using standard Schlenk techniques or in a glove box equipped with an atmosphere of purified nitrogen. The dihydrogen tetrametaphosphate salt $[PPN]_2[P_4O_{12}H_2]$ was prepared according to reported procedure. See, for example, Kamimura, S.; Kuwata, S.; Iwasaki, M.; Ishii, Y. Inorg. Chem. 2004, 43, 399-401, which is incorporated by reference in its entirety. Aqueous solutions were prepared using reagent grade deionized water (p>18 MΩcm; Ricca Chemical Company, USA). Acetone ($H_2O$ content <0.5 w/w %) was purchased from Macron Fine Chemicals and used as received. Acetonitrile, diethyl ether, methanol, THF and pentane were purified on a Glass Contour Solvent Purification System built by SG Water USA, LLC and stored with 4 A molecular sieves. Molecular sieves (4 A) were dried at 50 mTorr overnight at a temperature above 200° C. IR spectra were recorded on a Bruker Tensor 37 Fourier transform IR (FT-IR) spectrometer. Elemental analyses were performed by Robertson Microlit Laboratories, Inc. NMR solvents were obtained from Cambridge Isotope Laboratories and dried using standard literature techniques. $^1H$, $^{13}C$ {$^1H$}, and $^{31}P${$^1H$} spectra were recorded on either a Varian Mercury-300 or a Bruker AVANCE-400 spectrometer. $^1H$ and $^{13}C$ {$^1H$} NMR chemical shifts are reported in ppm relative to tetramethylsilane (TMS) and are referenced to the solvent peaks. $^{31}P$ {$^1H$}NMR chemical shifts are reported with respect to an external reference (85% $H_3PO_4$, 8 0.0 ppm).

Preparation of Binary Dimeric Vanadyl(IV) k,[2] Tetrametaphosphate (as its PPN Salt) $[PPN]_4[(VO)_2(P_4O_{12})_2]$ ($[PPN]_4[6]$)

Crystallization from the Reaction of $[PPN]_2[P4O_{12}H_2]$ with $VO(Acac)_2$

Under open air conditions in a fume hood, $[PPN]_2[P_4O_{12}H_2]$ (57.1 mg, 0.04 mmol, 1 equiv.) was mixed in acetone (6 mL) giving a heterogeneous mixture due to the poor solubility of $[PPN]_2[P_4O_{12}H_2]$ this solvent. To the resultant mixture was added dropwise the solution of $VO(acac)_2$ (10.8 mg, 0.04 mmol, 1 equiv.) in acetone (4 mL) affording a blue slurry. The mixture was kept stirring at room temperature for 4 h affording a homogeneous blue solution implying that the starting material $[PPN]_2[P_4O_{12}H_2]$ has been completely consumed. The solution was concentrated in vacuo to ca. 2 mL. After 10 min blue crystals started to form. The solution was allowed to stand undisturbed at room temperature for 15 h, after which time a crop of blue crystals was harvested, and dried in vacuo giving $[PPN]_4[6]$ as a blue crystalline solid (Yield: 26.8 mg, 0.0085 mmol, 42%).

Precipitation from the Reaction of $[PPN]_2[P_4O_{12}H_2]$ with $VO(Acac)_2$

Under open air conditions in a fume hood, $[PPN]_2[P_4O_{12}H_2]$ (224.3 mg, 0.16 mmol, 1 equiv.) was mixed in acetone (10 mL) affording a slurry, to which was added dropwise the solution of $VO(acac)_2$ (43.2 mg, 0.16 mmol, 1 equiv.) in acetone (8 mL). The heterogeneous mixture was kept stirring vigorously at room temperature. The formation of a clear homogeneous blue solution was not obtained this time. Instead a great deal amount of blue precipitate crushed out from the mixture after 1 h. The mixture was allowed to stir at room temperature for 15 h. The blue precipitate was collected on a Frit by filtration, washed with acetone (3×3 mL) and dried in vacuo giving 1 as pale blue powder (Yield: 202.3 mg, 0.064 mmol, 80%).

Characterization of $[PPN]_4[(VO)_2(P_4O_{12})_2]$ ($[PPN_{14}[6]$)

ESI-MS(-)($CH_3CN$, m/z): 191.3253 ($[(VO)(P_4O_{12})]^{2-}$), 382.6908 ($[(V(V)O)_2(P_4O_{12})_2]^2$), 383.7183 ($[(VO)(P_4O_{12})H]^-$). IR (ATR, $cm^{-1}$): v 1284 (s, P=O), 983 (s, V=O). Anal. Calcd for $C_{144}H_{120}N_4O_{26}P_{16}V_2$, $4(C_3H_6O)$ (3152.3292): C, 59.44; H, 4.60; N, 1.78%. Found: C, 59.52; H, 4.70; N, 1.77%.

Binary Dimeric Titanyl Tetrametaphosphate $[PPN]_4[(OTi)_2(P_4O_{12})_2]$ ($[PPN]_4[7]$)

Under open air conditions in a fume hood, a 100 mL round bottom flask was charged with solid $[PPN]_2[P_4O_{12}H_2]$ (411 mg, 0.295 mmol, 1 eq) and $[TiO(acac)_2]_2$(85 mg, 0.162 mmol, 0.55 eq). Acetone (60 mL) and MeCN (20 mL) were added to the flask, and the colorless solution was stirred at room temperature for a total of 12 h, at which point the reaction mixture was filtered through a pad of Celite to remove unreacted $[TiO(acac)_2]_2$. The resulting colorless solution was then concentrated to approximately 3 mL, during which time colorless $[PPN]_4[OTiP_4O_{12}]_2$ precipitated from solution. The supernatant was removed, and the colorless solids washed with acetone (3×5 mL). The solids were then dried under reduced pressure affording $[PPN]_4[7]$ as a colorless crystalline solid (Yield: 386 mg, 0.133 mmol, 45%).

Characterization of $[PPN]_4[OTiP_4O_{12}]_2$($[PPN]_4[7]$)

ESI-MS(-) ($CH_3CN$, m/z): 189.9402 ($[(TiO)(P_4O_{12})]^{2-}$). IR (ATR, $cm^{-1}$): v 1286 (s, P=O), 969 (s, Ti—O). 1H NMR ($CD_3CN$, 400.1 MHz, ppm) δ: 7.50-7.69 (m, 72H, $[PPN]^+$). $^{31}P${$^1H$} NMR ($CD_3CN$, 122 MHz, ppm) δ: 22.20 (s, 4P, PPN), −27.61 (s, 4P).

Preparation of Dimeric Molybdenum(TT) k,[2] Tetrametaphosphate Di-Acetate (as its PPN salt) $[PPN]_2[Mo_2(P_4O_{12})(OAc)_2]$ ($[PPN]_2[8]$)

Path: $[PPN]_2[P_4O_{12}H_2]$ with $Mo_2(OAc)_4$

In a glove box, $[PPN]_2[P_4O_{12}H_2]$ (112.3 mg, 0.08 mmol, 1 equiv.) and $Mo_2(OAc)_4$ (41.6 mg, 0.097 mmol, 1.2 equiv.) were mixed in MeCN (5 inL) affording a brown slurry due to the poor solubility of $Mo_2(OAc)_4$ in this solvent. The reaction mixture was kept stirring at room temperature for 20 min. $^{31}P${$^1H$} NMR spectroscopy revealed the formation of a new metaphosphate species showing a singlet at −21.04 ppm. The mixture was filtered through a glass microfiber filter to remove the excess of $Mo_2(OAc)_4$. To the filtrate was added diethyl ether (15 mL) affording a yellow-orange slurry. After ca. 1 min. yellow crystals started to form. The suspension was allowed to stand undisturbed at room temperature for 1 h, after which time a crop of yellow crystals was harvested. The collected crystals were washed with diethyl ether (2×4 mL) and pentane (1×4 mL). dried in vacuo giving 8 as orange solids (Yield: 126.3 mg, 0.07 mmol, 88%).

Characterization of $[PPN]_2[Mo_2(P_4O_{12})(OAc)_2]$ ($[PPN]_2[8]$)

ESI-MS(−) ($CH_3CN$, m/z):311.8126, 312.8141 ($[Mo_2P4O_{12}(OAc)_2]^{2-}$). IR (ATR, $cm^{-1}$): v 1273 (P=O), 981 (P—O). $^1H$ NMR ($CD_3CN$, 400.1 MHz, ppm) t. 7.50-7.69 (m, 72H, $[PPN]^+$), 2.74 (s, 6H, $CH_3COO^-$), 1.99 (s, 9H, $CH_3CN$). $^{31}P${$^1H$} NMR ($CD_3CN$, 161.9 MHz, ppm) δ 22.00 (s, 4P, PPN), −19.69 (s, 4P). $^{13}C$ NMR ($CD_3CN$, 100 MHz, ppm) δ: 182.04 (s), 133.65 (s), 132.27 (m), 129.41 (m), 127.78 (s), 126.69 (s), 22.30 (s). Anal. Calcd for $2(C_{36}H_{30}NP_2)$, $Mo_2P_4O_{16}C_4H_6$, $3(C_2H_3N)$ (1826.2311): C, 53.93; H, 4.14; N, 3.83%. Found: C, 53.84; H, 4.58; N, 3.53%.

Preparation of Binary Dimeric Molybdenum(II) k,[2] Tetrametaphosphate (as its PPN salt) $[PPN]_4[Mo_2(P_4O_{12})_2]$ ($[PPN]_4[9]$)

Path: $[PPN]_2[P_4O_{12}H_2]$ with $Mo_2(OAc)_4$ at 80° C.

In a glove box, $Mo_2(OAc)_4$ (68.6 mg, 0.16 mmol, 1 equiv.) and $[PPN]_2[P_4O_{12}H_2]$ (558.9 mg, 0.40 mmol, 2.5 equiv.) were mixed in MeCN (10 mL) affording a brown suspension. After stirring at room temperature for 2 min, the suspension was transferred to a Young-Schlenk tube and was kept stirring at 80° C. for 15 h. $^{31}P${$^1H$} NMR spectroscopy revealed the formation of the desired product in ca. 80% in situ yield. The byproduct $[PPN]_4[Mo_2(P_4O_{12})(OAc)_2]$ was formed in ca. 20% in situ yield. The mixture was then filtrated through a glass microfiber filter and the filtrate was divided into two vials (ca. 5 mL for each stock). To each stock was layered carefully diethyl ether (15 mL) on top of the solution. After standing at room temperature for 15 h, orange crystals were formed and collected, dried in vacuo giving [PPN]$_4$[9] as orange crystalline solids (yield: 298.6 mg, 0.097 mmol, 61%).

Characterization of [PPN]$_4$[Mo$_2$(P$_4$O$_{12}$)$_2$] ([PPN$_{14}$[9])

ESI-MS(−) (CH$_3$CN, m/z):410.5626, 411.5621 ([Mo(III)$_2$P8O$_{24}$]$^{2-}$). IR (ATR, cm$^{-1}$): ν 1274, 1233 (P=O), 978 (P—O). 1H NMR (CD$_3$CN, 400.1 MHz, ppm) δ: 7.48-7.71 (m, 144H, [PPN]$^+$). $^{31}$P{$^1$H} NMR (CD$_3$CN, 161.9 MHz, ppm) δ: 22.03 (s, 8P, PPN), −17.89 (s, 8P). $^{13}$C NMR (CD$_3$CN, 100 MHz, ppm) δ: 133.64 (s), 132.26 (m), 129.41 (m), 127.76 (d), 126.69 (d). Anal. Calcd for 4(C$_{36}$H$_{30}$NP$_2$), Mo$_2$O$_{24}$P$_8$, 0.70(C$_4$H$_{10}$O), 3.3 (C$_2$H$_3$N) (3077.45): C, 59.87; H, 4.48; N, 3.32%. Found: C, 58.52; H, 4.48; N, 3.28%.

Preparation of Monohydrogen Trimetaphosphate (as its PPN Salt) [PPN]$_2$[P$_3$O$_9$H]([PPN]$_2$[10])

Path: [PPN]$_3$[P$_3$O$_9$] H$_2$O with (CF$_3$CO)$_2$O

In a glove box, [PPN]$_3$[P$_3$O$_9$].H$_2$O (4.0 g, 2.1 mmol, 1 equiv.) was dissolved in MeCN (12 mL). To the resulting solution was added dropwise the solution of (CF$_3$CO)$_2$O (148 mg, 1.05 mmol, 0.5 equiv.) in MeCN (5 mL). The mixture was kept stirring at room temperature for 10 min. $^{31}$P{$^1$H} NMR revealed the formation of monohydrogen trimetaphosphate [PPN]$_2$[P$_3$O$_9$H] showing a broad singlet at −20.9 ppm. The solution was divided into 3 stocks. To each stock was added THE (150 mL) to crush out the desired product. The formed slurry was allowed to stand at room temperature for overnight. The formed crystalline solids were isolated, washed with THF (4×5 mL), dried in vacuo affording [PPN]$_2$[10] as white solids (Yield: 1.29 g, 0.98 mmol, 47%).

Characterization of [PPN]$_2$[P$_3$O$_9$H] ([PPN]$_2$[10])

$^1$H NMR (CD$_3$CN, 400.1 MHz, ppm): 11.63 (br, 1H, OH). 7.47-7.71 (m, 60H, Ph). $^{31}$P{$^1$H} NMR (CD$_3$CN, 122 MHz, ppm) δ: 22.10 (s, 4P, [PPN]$^+$), −20.26 (s, 3P).

Preparation of N-Trimetaphosphorylurea (as its PPN Salt) [PPN]$_2$ [P$_3$O$_8$N(Cy)CONH(Cy)] ([PPN]$_2$[11])

Path: [PPN]$_2$[P$_3$O$_9$H] with DCC

In a glove box, [PPN]$_2$[P$_3$O$_9$H] (160.9 mg, 0.12 mmol, 1 equiv.) and excess of DCC (198.2 mg, 0.96 mmol, 8 equiv.) were mixed in MeCN (4 mL). The solution was kept stirring at room temperature for 40 h. $^{31}$P{$^1$H} NMR revealed the quantitative formation of a new species. The mixture was filtrated through a glass microfiber filter to remove the generated byproduct DCU. The filtrate was evaporated in vacuo, and the residue was washed with THF (4×3 mL) to remove excess of DCC. The collected solid was dried in vacuo giving [PPN]$_2$[11] as a white solid (Yield: 145.5 mg, 0.096 mmol, 80%).

Characterization of [PPN]$_2$[P$_3$O$_8$N(Cy)CONH(Cy)] ([PPN]$_2$[11])

ESI-MS(−) (CH$_3$CN, m/z): 445.0159 ([P$_3$O$_8$N(Cy)CONH(Cy)H]$^-$). IR (ATR, cm$^{-1}$): ν 1253 (s, P=O), 990 (s, P—O). 1H NMR (CD$_3$CN, 400.1 MHz, ppm) δ: 8.29 (s, 1H, NH), 7.49-7.71 (m, 60H, Ph), 3.72 (td, $^3J_{PH}$=12 Hz, $^3J_{HH}$=4 Hz, 1H, NCH), 3.44 (q, $^3J_{HH}$=4 Hz, 1H, NHCH), 1.27-2.19 (m, 20H, CH$_2$). $^{31}$P NMR (CD$_3$CN, 122 MHz, ppm) δ: 20.97 (s, 4P, [PPN]$^+$), −17.00 (td, $^2J_{PP}$=26 Hz, $^3J_{PH}$=12 Hz, 1P), −22.90 (d, $^2J_{PP}$=26 Hz, 2P). $^{13}$C NMR (CD$_3$CN, 100 MHz, ppm) δ: 133.63 (s), 132.32 (m), 129.39 (m), 127.77 (d), 126.70 (d), 67.29 (s), 56.55 (s), 49.08 (s), 32.56 (s), 30.55 (s), 26.35 (s), 25.50 (s), 25.42 (s), 25.25 (s), 24.68 (s).

Preparation of Iron(II) Bis k$^3$ Trimetaphosphate (as its PPN salt) [PPN]$_4$[Fe(P$_3$O$_9$)$_2$]([PPN]$_4$[12])

Path: [PPN]$_2$[P$_3$O$_9$H] with Fe(acac)$_2$

In a glove box, Fe(acac)$_2$ (12.7 mg, 0.05 mmol, 1 equiv.) was mixed with MeCN (2 mL) affording a red-brown slurry, to which was added dropwise the solution of [PPN]$_2$[P$_3$O$_9$H] (132 mg, 0.10 mmol, 2 equiv.) in MeCN (3 mL). After stirring at room temperature for 15 h, the color of solution turned to brown. The resultant mixture was filtered through a glass microfiber filter to remove some dark brown solids. To the filtrate was added diethyl ether (10 mL) affording a slurry. The mixture was allowed to stay at room temperature for overnight affording a pale-yellow solution with some brown residue in the bottom of the vial. The supernatant solution was separated from the brown residue and was divided into two stocks. To each stock was added diethyl ether (10 mL) giving a white slurry, which was allowed to stand at room temperature for 24 h. During this period of time colorless crystalline solids were formed and harvested, washed with pentane (3 mL), dried in vacuo affording the desired product as pale-yellow solids (Yield: 89.3 mg, 0.0326 mmol, 65%).

Characterization of [PPN]$_4$[Fe(P$_3$O$_9$)$_2$] ([PPN]$_2$[12])

ESI-MS(−)(CH$_3$CN, m/z): 532.7360 ([Fe(P$_6$O$_{18}$)H$_3$]$^-$), 256.3290 ([Fe(P$_6$O$_{18}$)H$_2$]$^{2-}$). IR (ATR, cm$^{-1}$): ν 1252 (s, P=O), 947 (s, P—O).

Preparation of Dihydrogen Trimetaphosphate (as its PPN Salt) [PPN] [P$_3$O$_9$H$_2$]([PPN]$_2$[13])

Path: [PPN]$_3$[P$_3$O$_9$] H$_2$O with (CF$_3$SO$_2$)$_2$O

In a glovebox, [PPN]$_3$[P$_3$O$_9$].H$_2$O (0.1012 g, 0.054 mmol, 1 equiv.) was dissolved in MeCN (4 mL). To the resulting solution was added dropwise the solution of (CF$_3$SO$_2$)2O (0.0150 g, 0.053 mmol, 1 equiv.) in MeCN (1 mL). The mixture was kept stirring at room temperature for 25 min. $^{31}$P1H NMR revealed the formation of dihydrogen trimetaphosphate [PPN][P$_3$O$_9$H$_2$] showing a broad singlet at −25.7 ppm. Volatiles were removed under reduced pressure, and the resulting white solid was washed with THF (3×1 mL), diethyl ether (3×1 mL), and was dried under reduced pressure, affording [PPN]$_2$[13] as white solids (Yield:).

Characterization of [PPN] [P$_3$O$_9$H$_2$] ([PPN]$_2$[13])

$^1$H NMR (CD$_3$CN, 300.1 MHz, ppm) δ: 14.43 (br, 2H, OH), 7.47-7.71 (m, 30H, Ph). $^{31}$P{$^1$H} NMR (CD$_3$CN, 122 MHz, ppm) δ: 22.22 (s, 2P, [PPN]$^+$), −25.94 (s, 3P).

Preparation of Monohydrogen Tetrametaphosphate (as its PPN Salt) [PPN]$_3$[P$_4$O$_{12}$H]([PPN]$_2$[14])

Path: [PPN]$_4$[(P$_4$O$_{12}$)].5H$_2$O with [PPN]$_2$[P$_4$O$_{12}$H$_2$]

In a glovebox, a solid mixture of [PPN]$_4$[(P$_4$O$_{12}$)].5H$_2$O (0.0546 g, 0.039 mmol, 1 equiv.) and [PPN]$_2$[P$_4$O$_{12}$H$_2$] (0.1004 g, 0.039 mmol, 1 equiv.) was dissolved in MeCN (5 mL). The reaction mixture was stirred at room temperature for 20 min. $^{31}$P $^1$H NMR revealed the formation of monohydrogen tetrametaphosphate [PPN]$_3$[P$_4$O$_{12}$H] showing a broad singlet at −23.63 ppm. Volatiles were removed under reduced pressure, affording [PPN]$_2$[14] as white solids.

Characterization of [PPN]$_3$[P$_4$O$_{12}$H] ([PPN]$_2$[14])

$^1$H NMR (CD$_3$CN, 300.1 MHz, ppm): 11.50 (br, 1H, OH), 7.47-7.71 (m, 90H, Ph). $^{31}$P{$^1$H} NMR (CD$_3$CN, 122 MHz, ppm) δ: 22.23 (s, 6P, [PPN]$^+$), −23.55 (s, 4P).

Preparation of Trihydrogen tetrametaphosphate (as its PPN salt) [PPN][P$_4$O$_{12}$H$_3$]([PPN]$_2$ [15])

Path: [PPN]$_4$[(P$_4$O$_{12}$)].5H$_2$O and [PPN]$_2$[P$_4$O$_{12}$H$_2$] with (CF$_3$SO$_2$)$_2$O In a glovebox, a solid mixture of [PPN]$_4$[(P$_4$O$_{12}$)].5H$_2$O (0.0325 g, 0.013 mmol, 1.0 equiv.) and [PPN]$_2$[P$_4$O$_{12}$H$_2$] (0.1246 g, 0.089 mmol, 7.0 equiv.) was dissolved in MeCN (10 mL). To the resulting solution was added dropwise the solution of (CF$_3$SO$_2$)$_2$O (0.0181 g, 0.064 mmol, 5.1 equiv.) in MeCN (1 mL). The mixture was kept stirring at room temperature for 40 min. Volatiles were removed under reduced pressure, resulting in white solid. The solid was dissolved in MeCN (1 mL) and dimethoxyethane (10 mL)

was added to crash out the product. The resulting white solid was washed with THF 2×2 mL) and dried under reduced pressure, affording [PPN]$_2$[15] as white solids.

Characterization of [PPN] [P$_4$O$_{12}$H$_3$] ([PPN] [15])

$^1$H NMR (CD$_3$CN, 300.1 MHz, ppm) δ: 13.47 (br, 3H, OH), 7.47-7.71 (m, 30H, Ph). $^{31}$P{$^1$H} NMR (CD$_3$CN, 122 MHz, ppm) δ: 22.23 (s, 2P, [PPN]$^+$), −27.15 (s, 4P).

Preparation of Cholesterol Monohydrogen Tetrametaphosphate (as its PPN Salt) [PPN]$_2$[Cholesterol-P$_4$O$_{12}$H] ([PPN]$_2$[16])

Path: [PPN]$_2$[P$_4$O$_{11}$] with Cholesterol

In a glovebox, a solid mixture of [PPN]$_2$[P$_4$O$_{11}$] (0.0554 g, 0.040 mmol, 1.0 equiv.) and cholesterol (0.0156 g, 0.040 mmol, 1.0 equiv.) was dissolved in methylene chloride (2 mL). The mixture was kept stirring at room temperature for 6 days. Volatiles were removed under reduced pressure, resulting in white solid. The solid was slurried in THF (2 mL) overnight to remove by-products. The solid was isolated, washed with THF (1 mL), and dried under reduced pressure, affording [PPN]$_2$[16] as white solids. (Yield: 86%).

Characterization of [PPN]$_2$[Cholesterol-P$_4$O$_{12}$H] ([PPN]$_2$[16])

$^1$H NMR (CDCl$_3$, 300.1 MHz, ppm) δ: 13.10 (br, 1H, OH), 7.40-7.80 (m, 60H, [PPN]$^+$), 5.27 (d, 1H, =CH), 4.45 (m, 1H, P—OCH), 0.60-2.70 (m, 40H, H$_{cholesterol}$). $^{31}$P{$^1$H} NMR (CDCl3, 122 MHz, ppm) δ: 21.90 (s, 4P, [PPN]$^+$), −23.16 (t, $^2$J$_{PP}$=25 Hz, 1P), −24.86 (dd, $^2$J$_{PP}$=25, 28 Hz, 2P), −27.85 (t, $^2$J$_{PP}$=28 Hz, 1P).

Preparation of Adenosine Monohydrogen Tetrametaphosphate (as its PPN Salt) [PPN]$_2$-[Adenosine-P$_4$O$_{12}$H] ([PPN]$_2$[17])

Path: [PPN]$_2$[P$_4$O$_{11}$] with Adenosine

In a glovebox, a solid mixture of [PPN]$_2$[P$_4$O$_{11}$] (0.0853 g, 0.062 mmol, 1.0 equiv.) and adenosine (0.0168 g, 0.063 mmol, 1.0 equiv.) was slurried in MeCN (3 inL). The mixture was kept stirring at room temperature for 1 day. Volatiles were removed under reduced pressure, resulting in white solid. The solid was washed with THF (3×1 mL), and dried under reduced pressure, affording [PPN]$_2$[17] as white solids. The reaction resulted in a mixture of 2 isomers of [PPN]$_2$[adenosine-P$_4$O$_{12}$H], as indicated by 2 sets of signals in $^1$H NMR.

Characterization of [PPN]$_2$[Adenosine-P$_4$O$_{12}$H] ([PPN]$_2$[17])

$^1$H NMR (DMSO-d$_6$, 400.1 MHz, ppm) δ: 8.53 (s, 1H, 2-CH), 8.20 (s, 1H, 8-CH), 5.92 (d, 1H, 1'-CH), 4.56 (t, 1H, 2'-CH). $^{31}$P{$^1$H} NMR (DMSO-d$_6$, 122 MHz, ppm) δ: 21.80 (s, 4P, [PPN]$^+$), −24.31 (b), −25.69 (b).

Preparation of 2'-Deoxyadenosine Monohydrogen Tetrametaphosphate (as its PPN Salt) [PPN]$_2$[2'-Deoxyadenosine-P$_4$O$_{12}$H] ([PPN]$_2$[18])

Path: [PPN]$_2$[P$_4$O$_{11}$] with 2'-Deoxyadenosine

In a glovebox, a solid mixture of [PPN]$_2$[P$_4$O$_{11}$] (0.0527 g, 0.038 mmol, 1.0 equiv.) and 2'-deoxyadenosine (0.0096 g, 0.038 mmol, 1.0 equiv.) was slurried in MeCN (2 mL). The mixture was kept stirring at room temperature for 1 day. Volatiles were removed under reduced pressure, affording 18 as white solids (Yield:). The reaction resulted in a mixture of 2 isomers of [PPN]$_2$[2'-deoxyadenosine-P$_4$O$_{12}$H], as indicated by 2 sets of signals in 1H NMR.

Characterization of [PPN]$_2$[2'-Deoxyadenosine-P$_4$O$_{12}$H] ([PPN]$_2$[18])

$^1$H NMR (DMSO-d$_6$, 400.1 MHz, ppm) δ: 8.50 (s, 1H, 2-CH), 8.17 (s, 1H, 8-Cfl), 6.36 (d, 1H, 1'-CH). $^{31}$P{$^1$H} NMR (DMSO-d$_6$, 122 MHz, ppm) δ: 21.80 (s, 4P, [PPN]$^+$), −24.27 (b), −25.92 (b).

Preparation of TBA Salts of Dihydrogen Tetrametaphosphate [TBA]$_2$[P$_4$O$_{12}$H$_2$] (19) and Tetrametaphosphate Anhydride [TBA]$_2$[P$_4$O$_{11}$] (20)

Other countercations besides PPN could also be employed. Treatment of the TBA (TBA=tetrabutylammonium) salt of tetrametaphosphate [TBA]$_4$[P$_4$O$_{12}$] 5H$_2$O with 1 equivalent of TFAA in wet acetone at room temperature afforded the quantitative formation of the TBA salt of dihydrogen tetrametaphosphate [TBA]$_2$[P$_4$O$_{12}$H$_2$] (19), as confirmed by $^{31}$P{$^1$H} NMR spectroscopy showing a singlet at −24.96 ppm. The constitution was further proven by the reaction of [PPN]$_2$[19] with DCC in acetone affording the TBA salt of tetrametaphosphate anhydride [TBA]$_2$[P$_4$O$_{11}$] (20), as revealed by the characteristic two triplet resonances at −24.11 and −32.00 ppm in the $^{31}$P{$^1$H} NMR spectrum.

Path: [TBA]$_4$[P$_4$O$_{12}$].5H$_2$O with (CF$_3$CO)$_2$O

Under open air condition in a fume hood, [TBA]$_4$[P$_4$O$_{12}$].5H$_2$O (100.6 mg, 0.073 mmol, 1 equiv.) was dissolved in wet acetone (3 mL). To the resulting solution was added dropwise the solution of (CF$_3$CO)$_2$O (10.4 μL, 0.73 mmol, 1 equiv.) in a solution of wet acetone (1 mL). The mixture was kept stirring at room temperature for 10 min. $^{31}$P{$^1$H}NMR revealed the quantitative formation of the TBA salt of dihydrogen tetrametaphosphate [TBA]$_2$[P$_4$O$_{12}$H$_2$] showing a singlet at −24.96 ppm. The formation of dihydrogen tetrametaphosphate [TBA]$_2$[P$_4$O$_{12}$H$_2$] was further confirmed by addition of dehydrating reagent DCC to the acetone solution resulting in the formation of the TBA salt of tetrametaphosphate anhydride [TBA]$_2$[P$_4$O$_{11}$]. The $^{31}$P{$^1$H} NMR spectrum revealed the characteristic two triplet resonances at −24.11 and −32.00 ppm.

Characterization of [TBA]$_2$[P$_4$O$_{12}$H$_2$] ([TBA]$_2$[19])

$^{31}$P{$^1$H} NMR (Me$_2$CO, 122 MHz, ppm): (5: −24.96 (s, 4P). Characterization of [TBA]$_2$[P$_4$O$_{11}$] ([TBA]$_2$[20])

$^{31}$P{$^1$H} NMR (Me$_2$CO, 122 MHz, ppm): δ: −24.11 (t, $^2$J$_{PP}$=29 Hz, 2P), −32.00 (t, $^2$J$_{PP}$=29 Hz, 2P).

The following lists possible cations.

Nitrogen-Based Cations

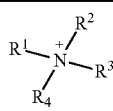

1

R$^1$ to R$^4$ are independently hydrogen; or straight or branched, saturated or unsaturated, alkyl containing 1 to 60 carbon atoms and optionally containing a linkage of the formula —O—, —S—, —NH—, —C(O)—, —C(O)O—, —OC(O)—, —C(O)NH— or —NHC(O)—, and optionally substituted with —CN, —Cl, —Br, —F, aryl, aryloxy, heterocyclic, or cyclo-C$_3$-C$_8$-alkyl; or R$^1$ to R$^4$ are independently selected from the group consisting of bicyclic, tricyclic and polycyclic alkyl, cyclo-C$_3$-C$_8$-alkyl, aryl, and heterocyclic, any of which is optionally substituted with —CN, —Cl, —Br, —F, or with phenyl, benzyl, or straight or branched, saturated

| | | |
|---|---|---|
| | | or unsaturated, alkyl or alkoxy containing up to 12 carbon atoms, the optional phenyl, benzyl, alkyl and alkoxy substituents being optionally substituted with —CN, —Cl, —Br, —F, or $C_1$-$C_6$ alkyl |
| 2 | 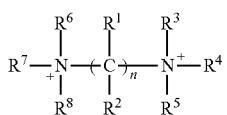 | $R^1$ to $R^8$ are the same as the R claimed in entry 1.<br>n > 0 |
| 3 | 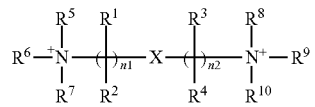 | $R^1$ to $R^{10}$ are the same as the R claimed in entry 1.<br>n1, n2 > 0<br>X = O, S, NR (R = H, alkyl, aryl) |
| 4 | 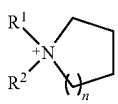 | $R^1$ to $R^2$ are the same as the R claimed in entry 1.<br>n > 0 |
| 5 | 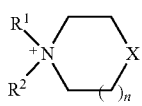 | $R^1$ to $R^2$ are the same as the R claimed in entry 1.<br>n > 0<br>X = O, S |
| 6 | 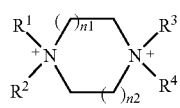 | $R^1$ to $R^4$ are the same as the R claimed in entry 1.<br>n1, n2 > 0 |
| 7 | 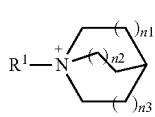 | $R^1$ is the same as the R claimed in entry 1.<br>n1, n2, n3 > 0 |
| 8 | 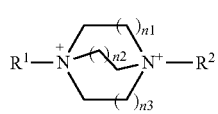 | $R^1$ to $R^2$ are the same as the R claimed in entry 1.<br>n1, n2, n3 > 0 |
| 9 | 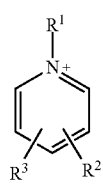 | $R^1$ to $R^3$ are the same as the R claimed in entry 1. |
| 10 | 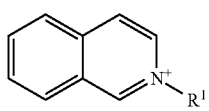 | $R^1$ is the same as the R claimed in entry 1. |
| 11 | 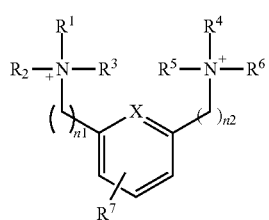 | $R^1$ to $R^7$ are the same as the R claimed in entry 1.<br>X = C, N<br>n1, n2 ≥ 0 |

| | | |
|---|---|---|
| 12 | 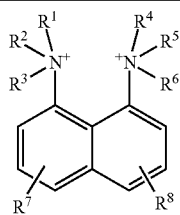 | $R^1$ to $R^8$ are the same as the R claimed in entry 1. |
| 13 | 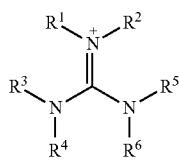 | $R^1$ to $R^6$ are the same as the R claimed in entry 1. |
| 14 | 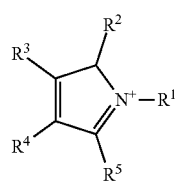 | $R^1$ to $R^5$ are the same as the R claimed in entry 1. |
| 15 | 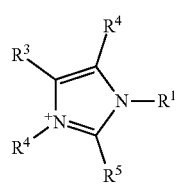 | $R^1$ to $R^5$ are the same as the R claimed in entry 1. |
| 16 | 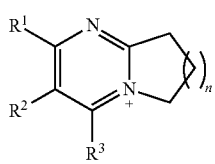 | $R^1$ to $R^3$ are the same as the R claimed in entry 1. $n > 0$ |
| 17 | 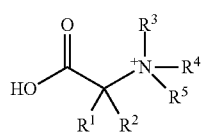 | $R^1$ to $R^5$ are the same as the R claimed in entry 1. |

Phosphorus-Based Cations

| | | |
|---|---|---|
| 18 | 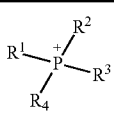 | $R^1$ to $R^4$ are the same as the R claimed in entry 1. |
| 19 | 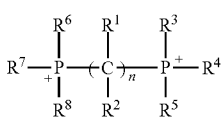 | $R^1$ to $R^8$ are the same as the R claimed in entry 1. $n > 0$ |
| 20 | 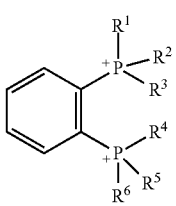 | $R^1$ to $R^6$ are the same as the R claimed in entry 1. |
| 21 | 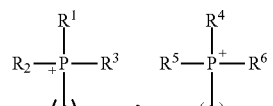 | $R^1$ to $R^7$ are the same as the R claimed in entry 1. n1, n2 > 0 |
| 22 | 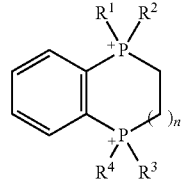 | $R^1$ to $R^4$ are the same as the R claimed in entry 1. $n > 0$ |

| | | |
|---|---|---|
| 23 | 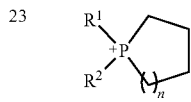 | $R^1$ to $R^2$ are the same as the R claimed in entry 1. $n > 0$ |

Alkali and Alkali-Earth Metal Cations
Na(15-crown-5)
Na(benzo-15-crown-5)
K(18-crown-6)
K(benzo-18-crown-6)
K(dibenzo-18-crown-6)
K(dicyclohexyl-18-crown-6)
K(kryptofix 222)
K(diaza-18-crown-6)
Li(12-crown-4)
Ca(kryptofix 221)
Ionic Liquid Cations
1,1-dimethyl-pyrrolidinium
1,1-dimethyl-pyrrolidinium
1-butyl-1-ethyl-pyrrolidinium
1-butyl-1-methyl-pyrrolidinium
1-ethyl-1-methyl-pyrrolidinium
1-hexyl-1-methyl-pyrrolidinium
1,3-methyl-imidazolium
1-ethyl-2-3-methyl-imidazolium
1-propyl-2-3-methyl-imidazolium
1-pentyl-3-methyl-imidazolium
1-decyl-3-methyl-imidazolium
1-dodecyl-3-methyl-imidazolium
1-benzyl-3-methyl-imidazolium
1-ethyl-3-methyl-imidazolium
1-hexyl-2-3-methyl-imidazolium
1-hexadecyl-2-3-methyl-imidazolium
1-hexadecyl-3-methyl-imidazolium
1-hexyl-3-methyl-imidazolium
1-methyl-3-(3-phenyl-propyl)-imidazolium
1-octyl-3-methyl-imidazolium
1-octadecyl-3-methyl-imidazolium
1-tetradecyl-3-methyl-imidazolium
3-methyl-imidazolium
1-ethyl-pyridinium
1-butyl-pyridinium
1-hexyl-pyridinium
4-methyl-n-butylpyridinium
1-hexyl-4-methyl-pyridinium
1-octyl-1-methyl-pyrrolidinium
1-octyl-pyridinium
4-methyl-1-octyl-pyridinium
trihexyl-tetradecyl-phosphonium
triisobutyl-methyl-phosphonium
tetrabutyl-phosphonium
benzyl-triphenyl-phosphonium
guanidinium
N,N,N,N-tetramethyl-N-ethylguanidinium
N,N,N,N,N-pentamethyl-N-propyl-guanidinium
N-butyl-isoquinolinium
O-ethyl-N,N,N,N-tetramethylisouronium
O-methyl-N,N,N,N-tetramethylisouronium
S-ethyl-N,N,N,N-tetramethylisothiouronium Other embodiments are within the scope of the following claims.

What is claimed is:

1. A compound comprising dihydrogen metaphosphate and a cation, where the cation includes an organic cation.

2. The compound of claim 1, where the cation includes a $[PPN]^+$.

3. The compound of claim 1, wherein the cation includes a $[R_4N]^+$, where R is nBu, sBu, i'Bu, nPr, i'Pr, Et, or Me.

4. The compound of claim 1, wherein the cation includes a nitrogen-based cation.

5. The compound of claim 1, wherein the cation includes a phosphorus-based cation.

6. The compound of claim 1, wherein the cation includes an alkali or an alkali-earth metal cation.

7. The compound of claim 1, wherein the cation includes an ionic liquid cation.

8. The compound of claim 1, wherein the dihydrogen metaphosphate is a dihydrogen tetrametaphosphate includes $[P_4O_{12}H_2]_{2-}$.

* * * * *